US 10,926,047 B2

(12) United States Patent
Pratt, Jr. et al.

(10) Patent No.: US 10,926,047 B2
(45) Date of Patent: Feb. 23, 2021

(54) TRANSVERSELY-ACTIVATED VALVE FOR A THERAPEUTIC VAPORIZER BAG ATTACHMENT SYSTEM

(71) Applicant: Robert Irving Pratt, Jr., El Cajon, CA (US)

(72) Inventors: Robert Irving Pratt, Jr., El Cajon, CA (US); Joshua Smith Young, La Jolla, CA (US)

(73) Assignee: Robert Irving Pratt, Jr., El Cajon, CA (US)

( * ) Notice: Subject to any disclaimer, the term of this patent is extended or adjusted under 35 U.S.C. 154(b) by 216 days.

(21) Appl. No.: 16/024,444

(22) Filed: Jun. 29, 2018

(65) Prior Publication Data

US 2018/0369523 A1    Dec. 27, 2018

Related U.S. Application Data

(63) Continuation of application No. 14/182,945, filed on Feb. 18, 2014, now abandoned, which is a
(Continued)

(51) Int. Cl.
*A61M 11/02* (2006.01)
*A61M 16/00* (2006.01)
(Continued)

(52) U.S. Cl.
CPC ........ *A61M 16/0078* (2013.01); *A61M 11/02* (2013.01); *A61M 11/042* (2014.02);
(Continued)

(58) Field of Classification Search
CPC .......... A61M 15/0093; A61M 15/0013; A61M 15/0015; A61M 15/0016; A61M 11/008
See application file for complete search history.

(56) References Cited

U.S. PATENT DOCUMENTS

| 1,968,509 A | 7/1934 | Tiffany |
| 2,057,353 A | 10/1936 | Whittemore |

(Continued)

FOREIGN PATENT DOCUMENTS

| AT | 249853 | 10/2003 |
| AT | 489981 | 12/2010 |

(Continued)

OTHER PUBLICATIONS

Office Action in Canadian Application No. 2812282, filed Mar. 21, 2013, dated Aug. 4, 2017 in 3 pages.
(Continued)

*Primary Examiner* — LaToya M Louis
(74) *Attorney, Agent, or Firm* — Knobb, Martens, Olson & Bear LLP

(57) ABSTRACT

A therapeutic vaporizer inhalation bag attachment system with an integrated valve includes a body having a lumen extending between the two openings of the body, a bag coupling, and a valve positioned within the lumen. A first end of the body may include a mouthpiece and the second end of the body may include bag coupling to attach an inhalation bag. The body may include a plurality of cooling ribs extending in parallel with the lumen along an outer surface of a sidewall of the body. The valve may be a duck-bill valve configured to move between a first position which allows flow of vapor through the lumen in a first direction extending from the first opening to the second opening, and a second position which prevents substantial flow of vapor through the lumen in a second direction from the second opening to the first opening, the valve having two flaps extending within the lumen inwardly from an inner sidewall of the body

13 Claims, 23 Drawing Sheets

Related U.S. Application Data continuation-in-part of application No. 13/823,918, filed as application No. PCT/US2011/052835 on Sep. 22, 2011, now abandoned.

(60) Provisional application No. 61/766,603, filed on Feb. 19, 2013, provisional application No. 61/385,403, filed on Sep. 22, 2010.

(51) Int. Cl.

| | | |
|---|---|---|
| *A61M 11/04* | (2006.01) | |
| *A61M 16/14* | (2006.01) | |
| *A61M 16/08* | (2006.01) | |
| *A61M 16/20* | (2006.01) | |
| *A61M 16/10* | (2006.01) | |
| *A61M 11/00* | (2006.01) | |
| *A61M 15/08* | (2006.01) | |
| *A61M 15/00* | (2006.01) | |

(52) U.S. Cl.
CPC ....... *A61M 11/003* (2014.02); *A61M 15/0021* (2014.02); *A61M 15/08* (2013.01); *A61M 16/0816* (2013.01); *A61M 16/107* (2014.02); *A61M 16/108* (2014.02); *A61M 16/14* (2013.01); *A61M 16/20* (2013.01); *A61M 2016/102* (2013.01); *A61M 2202/0233* (2013.01); *A61M 2205/07* (2013.01); *A61M 2205/3331* (2013.01); *A61M 2205/3368* (2013.01); *A61M 2205/3633* (2013.01); *A61M 2205/3653* (2013.01); *A61M 2205/502* (2013.01); *A61M 2205/583* (2013.01); *A61M 2205/587* (2013.01); *A61M 2205/8206* (2013.01); *A61M 2209/06* (2013.01); *A61M 2209/08* (2013.01)

(56) References Cited

U.S. PATENT DOCUMENTS

| | | | |
|---|---|---|---|
| 2,755,060 A | 7/1956 | Twyman | F16K 7/00 137/847 |
| D221,657 S | 8/1971 | Katzman | |
| 3,822,720 A | 7/1974 | Souza | F04B 43/08 137/846 |
| 3,859,997 A | 1/1975 | Douma et al. | |
| D237,198 S | 10/1975 | Dollen | |
| 4,027,681 A | 6/1977 | Todd | |
| 4,598,707 A | 7/1986 | Agdanowski et al. | |
| 4,968,294 A | 11/1990 | Salama | A61F 2/0009 128/DIG. 25 |
| 5,031,612 A | 7/1991 | Clementi | |
| 5,147,312 A | 9/1992 | Walker | A61M 5/142 417/477.1 |
| 5,195,514 A | 3/1993 | Liu et al. | |
| D374,922 S | 10/1996 | Moore | |
| D374,923 S | 10/1996 | Moore | |
| D421,109 S | 2/2000 | Wolfe | |
| D424,677 S | 5/2000 | Chen | |
| D425,975 S | 5/2000 | Wolfe | |
| 6,089,230 A | 7/2000 | Barker | |
| 6,095,153 A | 8/2000 | Kessler et al. | |
| 6,149,141 A | 11/2000 | Birdsell et al. | |
| 6,158,431 A | 12/2000 | Poole | |
| D443,350 S | 6/2001 | Delmenico et al. | |
| D450,116 S | 11/2001 | Dal Toso | |
| 6,413,476 B1 | 7/2002 | Barnhart | |
| 6,513,524 B1 | 2/2003 | Storz | |
| 6,708,950 B2 | 3/2004 | Christensen | A45F 3/16 220/714 |
| D510,135 S | 9/2005 | Mariotti | |
| D511,568 S | 11/2005 | Wheatley | |
| 6,990,978 B2 | 1/2006 | Shayan | |
| D535,002 S | 1/2007 | Caserta et al. | |
| 7,314,046 B2 | 1/2008 | Schroeder | |
| D576,724 S | 9/2008 | Jensen et al. | |
| D583,463 S | 12/2008 | Wood et al. | |
| D591,411 S | 4/2009 | Weisbeck | |
| 7,730,887 B2 | 6/2010 | Deane | |
| 7,840,122 B1 | 11/2010 | Hanrahan et al. | |
| D637,280 S | 5/2011 | Harvey et al. | |
| D639,414 S | 6/2011 | Berndt | |
| 7,960,673 B2 | 6/2011 | Li et al. | |
| D642,733 S | 8/2011 | Sweitzer | |
| D649,237 S | 11/2011 | Bilko et al. | |
| D680,208 S | 4/2013 | Gordon | |
| D680,684 S | 4/2013 | Enshiwat | |
| 8,474,663 B2 | 7/2013 | Westphal | |
| D698,429 S | 1/2014 | Jorgensen | |
| D700,316 S | 2/2014 | Nichols | |
| D703,300 S | 4/2014 | Lee | |
| 8,715,210 B2 | 5/2014 | Orlando | |
| 8,733,349 B2 | 5/2014 | Bath | A61M 16/0066 128/200.24 |
| D713,971 S | 9/2014 | Nichols | |
| D719,248 S | 12/2014 | Smith et al. | |
| D742,492 S | 11/2015 | Robinson | |
| D752,807 S | 3/2016 | Young | |
| 2002/0052562 A1 | 5/2002 | Lipman | |
| 2002/0158351 A1 | 10/2002 | Wohrle | |
| 2003/0009079 A1 | 1/2003 | Beaufore | A61F 2/0013 600/29 |
| 2003/0209246 A1 | 11/2003 | Schroeder et al. | |
| 2004/0099266 A1 | 5/2004 | Cross et al. | |
| 2004/0211418 A1 | 10/2004 | Shayan | |
| 2004/0241053 A1 | 12/2004 | Thompson | |
| 2005/0034723 A1 | 2/2005 | Bennett | |
| 2005/0150491 A1 | 7/2005 | Chen | |
| 2005/0169615 A1 | 8/2005 | Glucksman | |
| 2006/0121136 A1 | 6/2006 | Oka et al. | |
| 2006/0129109 A1 | 6/2006 | Shaw | A61M 39/26 604/246 |
| 2006/0283449 A1 | 12/2006 | Balch et al. | |
| 2007/0045288 A1 | 3/2007 | Nelson | |
| 2007/0101994 A1 | 5/2007 | Waters | A61M 11/06 128/205.12 |
| 2007/0125765 A1 | 6/2007 | Nelson | |
| 2007/0169776 A1 | 7/2007 | Kepler | |
| 2008/0023003 A1 | 1/2008 | Rosenthal | |
| 2008/0029099 A1 | 2/2008 | Storz | |
| 2008/0053979 A1 | 3/2008 | Toya | |
| 2008/0138051 A1 | 6/2008 | Velazquez et al. | |
| 2009/0078253 A1 | 3/2009 | Bao | |
| 2009/0110379 A1 | 4/2009 | McGhin | |
| 2009/0293892 A1 | 12/2009 | Williams | |
| 2010/0012118 A1 | 1/2010 | Storz | |
| 2010/0176213 A1 | 7/2010 | Belongia | |
| 2011/0103776 A1 | 5/2011 | Jorgensen | |
| 2011/0120482 A1 | 5/2011 | Brenneise | |
| 2011/0162647 A1 | 7/2011 | Huby | |
| 2012/0222696 A1 | 9/2012 | Nichols | |
| 2013/0174842 A1 | 7/2013 | Young et al. | |
| 2014/0158129 A1 | 6/2014 | Pratt et al. | |

FOREIGN PATENT DOCUMENTS

| | | |
|---|---|---|
| CA | 2671604 | 1/2010 |
| CN | 1400026 A | 10/2001 |
| CN | 1700924 A | 11/2005 |
| CN | 101132823 A | 2/2008 |
| CN | 101537221 A | 3/2009 |
| DE | 19546167 | 6/1997 |
| DE | 29806239 | 9/1998 |
| DE | 19803376 | 10/1999 |
| DE | 10042396 | 6/2005 |
| DE | 102006017787 | 10/2007 |
| DE | 502006008441 | 1/2011 |
| EP | 0 139 363 | 2/1985 |
| EP | 0143208 | 6/1985 |
| EP | 933093 | 9/2003 |
| EP | 1845368 | 10/2007 |

(56) References Cited

FOREIGN PATENT DOCUMENTS

| EP | 2145643 | 1/2010 |
|---|---|---|
| EP | 1884254 | 2/2011 |
| ES | 2355983 | 4/2011 |
| FR | 2271845 | 12/1975 |
| JP | 2004-531555 A | 10/2004 |
| JP | 5920940 | 4/2016 |
| WO | WO 8102982 | 10/1981 |
| WO | WO 02/094218 A2 | 11/2002 |
| WO | WO 2004098689 | 11/2004 |
| WO | WO 2005021074 | 3/2005 |
| WO | WO 2006/082571 A1 | 10/2006 |
| WO | WO 2008/015918 | 2/2008 |
| WO | WO 2008/050434 A1 | 5/2008 |
| WO | WO 2010/035581 A1 | 4/2010 |
| WO | WO 2012/038861 A1 | 3/2012 |
| WO | WO 2012/040512 A2 | 3/2013 |

OTHER PUBLICATIONS

Communication pursuant to Article 94(3) EPC dated May 24, 2017 in EP 14155540.9, which is related to the present application.

Notice of Allowance (with English translation) issued by the Japanese Patent Office (JPO) dated Mar. 22, 2016 in JP 2013-530330; which is related to the present application.

Notification to Grant Patent Right for Invention issued by the State Intellectual Property Office of China dated Jul. 4, 2016 in CN 2011800544310; which is related to the present application.

First Office Action issued by the Japanese Patent Office in JP 2013-530330, which is related to the present application.

Second Office Action dated Nov. 26, 2015 by the State Intellectual Property Office China in CN 201180054431.0.

Extended Supplementary European Search Report dated Feb. 26, 2016 in EP 11 82 7570; which is related to the present application.

Extended European Search Report (ESR) dated Apr. 6, 2014 by the European Patent Office in EP 14155540.9, which is related to the present application.

First Office Action dated Feb. 2, 2015 by the State Intellectual Property Office China in CN 201180054431.0, which is related to the present application.

International Search Report and Written Opinion in PCT Application No. PCT/US11/52835, dated Apr. 5, 2012, filed Sep. 22, 2011.

Video at http://www.youtube.com/watch?v=Zo0VS_-VFIM (posted Sep. 20, 2011); now available at http://web.archive.org/web/20111006152537/http://www.clovershield.com/about/.

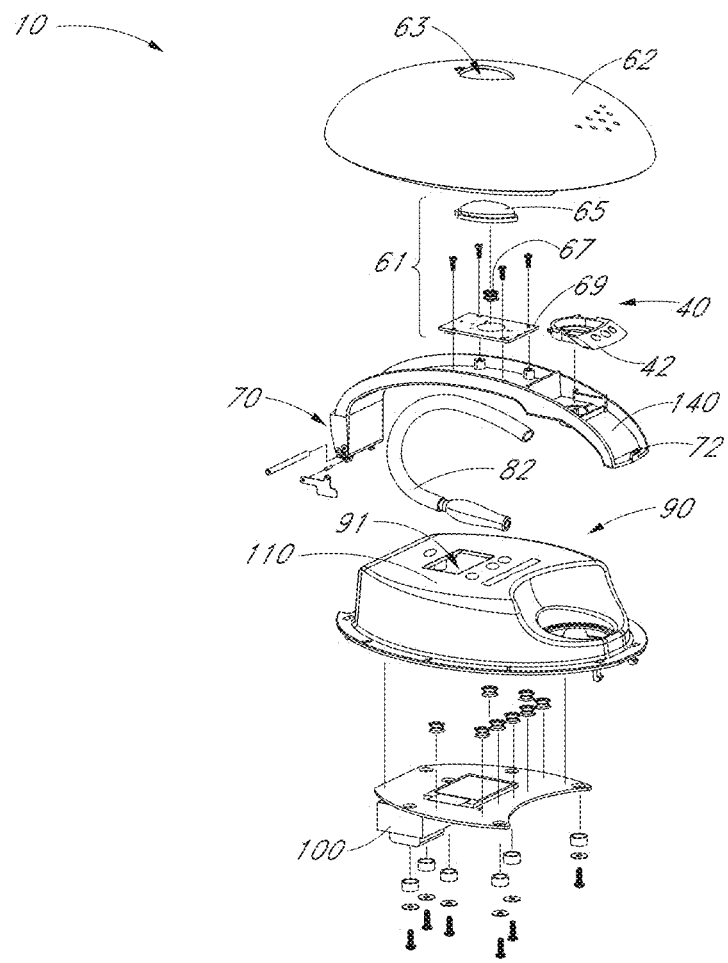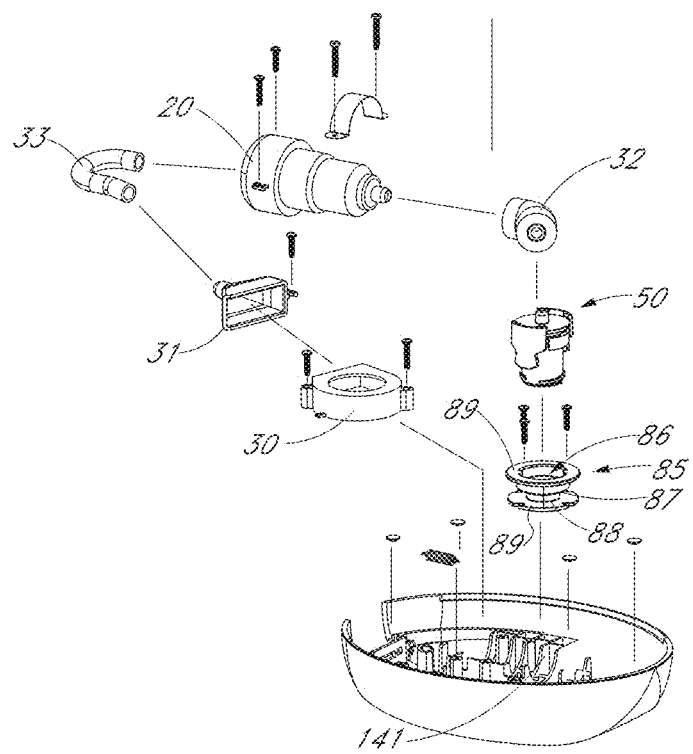
FIG. 1C

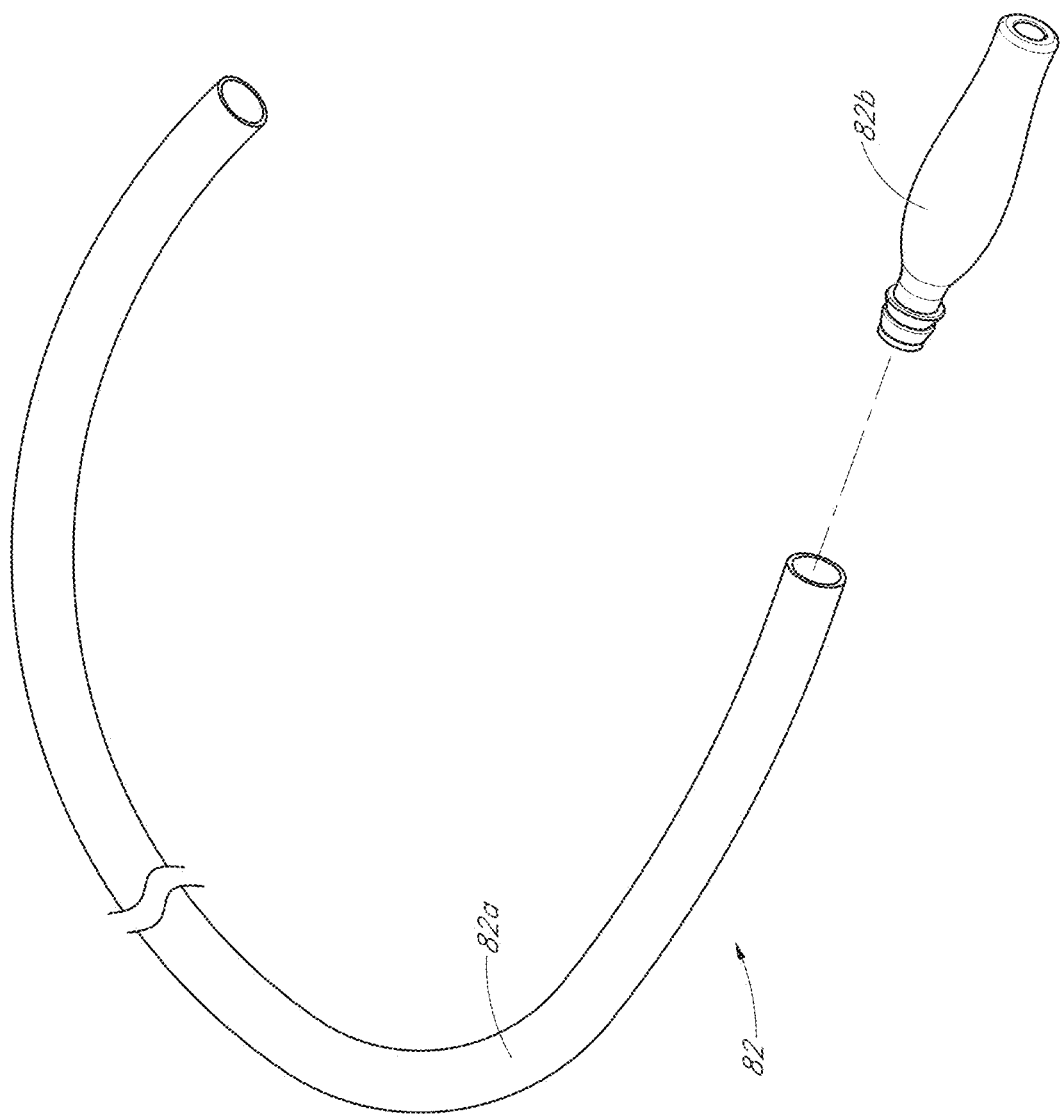

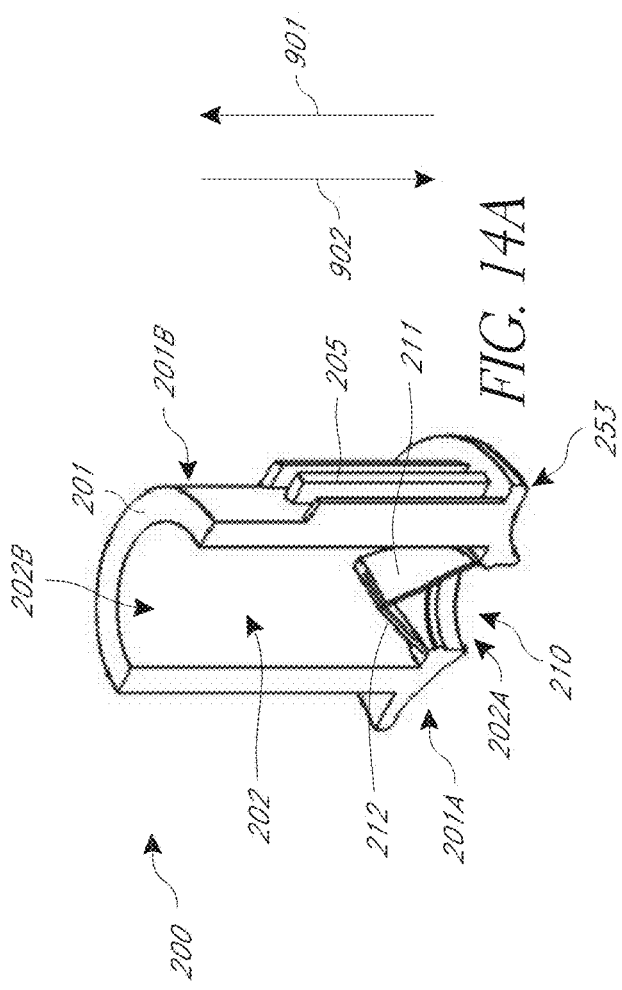
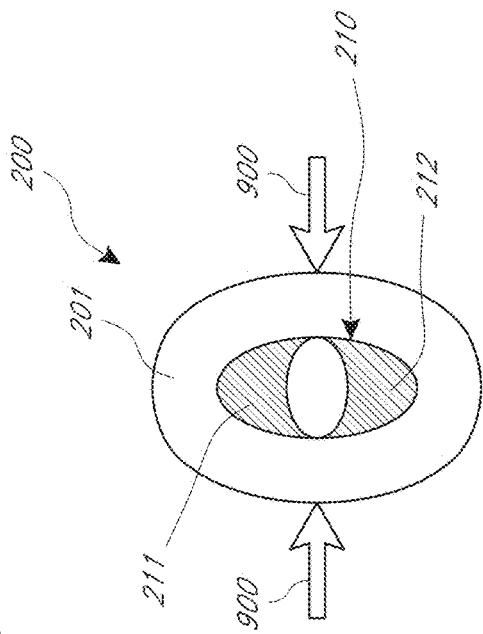
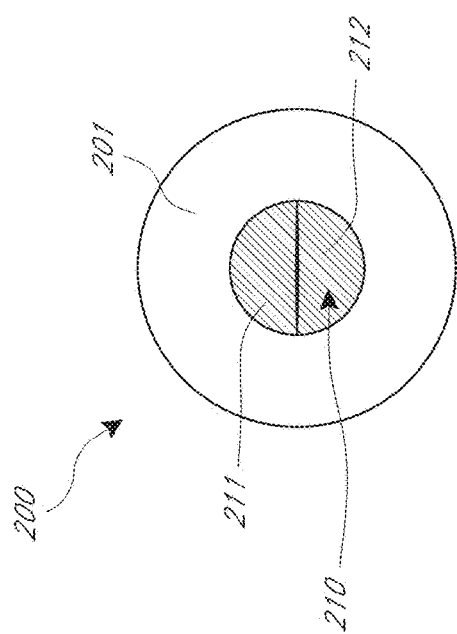
FIG. 14A
FIG. 14B
FIG. 14C

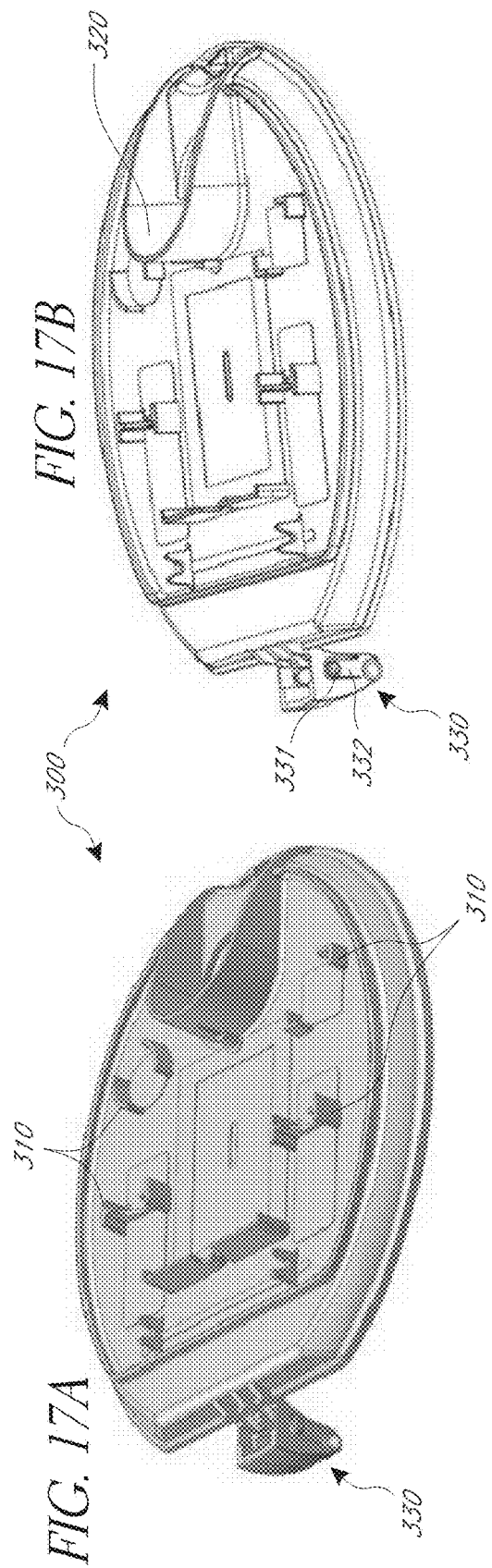
FIG. 17A
FIG. 17B
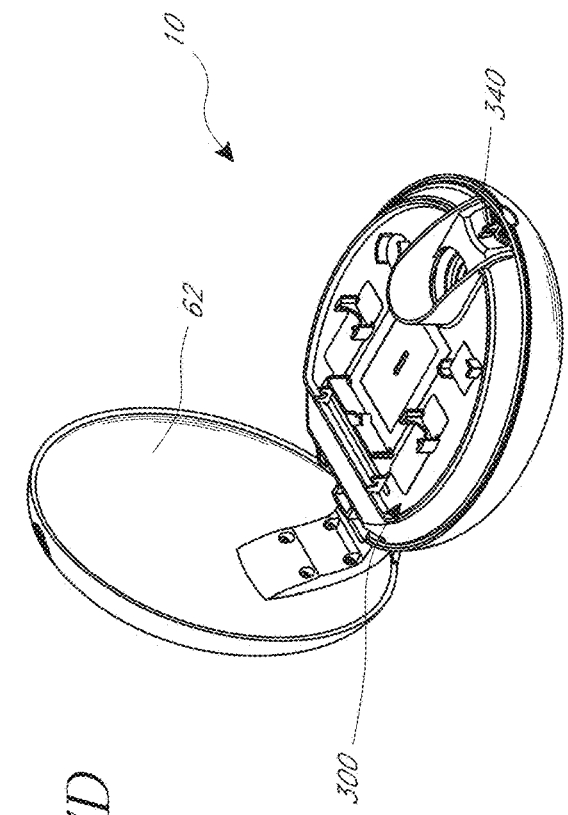
FIG. 17D
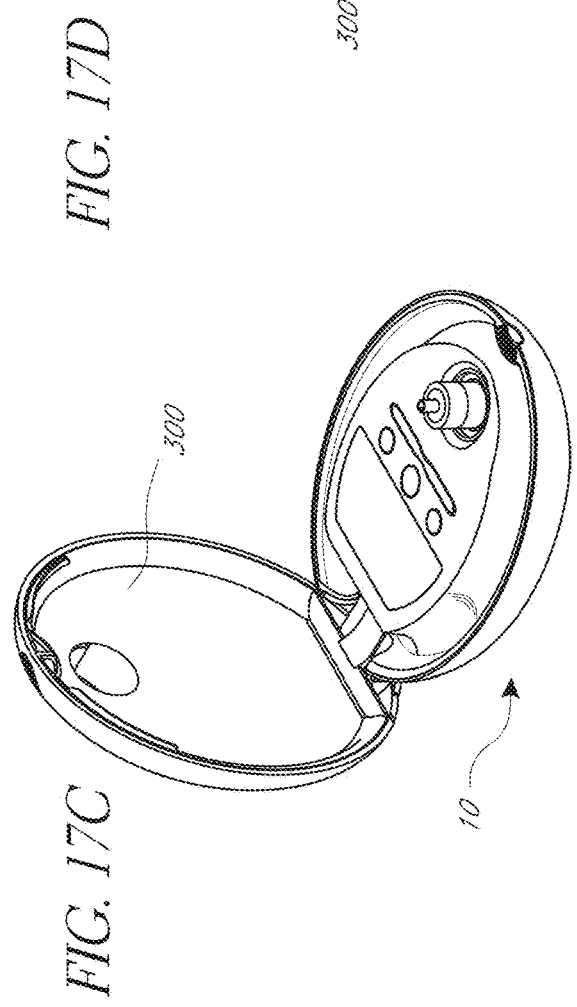
FIG. 17C

TRANSVERSELY-ACTIVATED VALVE FOR A THERAPEUTIC VAPORIZER BAG ATTACHMENT SYSTEM

CROSS-REFERENCE TO RELATED APPLICATIONS

This application is a Continuation of U.S. Non-Provisional application Ser. No. 14/182,945, filed Feb. 18, 2014, which claims priority to U.S. Provisional Patent Application No. 61/766,603, filed Feb. 19, 2013, and is a continuation-in-part of U.S. application Ser. No. 13/823,918, filed Mar. 15, 2013, which is a National Phase Application based on and claiming the benefit of PCT/US2011/052835, filed Sep. 22, 2011, which claims the benefit of U.S. Provisional Patent Application 61/385,403, filed Sep. 22, 2010, the disclosures of which are incorporated herein by reference in their entireties.

BACKGROUND OF THE INVENTION

Field

The present disclosure relates generally to an apparatus for vaporizing a therapeutic material. More specifically, the present disclosure relates to a therapeutic vaporizer inhalation bag attachment system with an integrated valve.

Description of the Related Art

Many vaporizer devices are known, and are often used as a therapeutic device to provide gaseous, vaporized medications, as an alternative to the risks associated with the intravenous or oral medications so common in Western medical practice. Therapeutic devices are growing in popularity, driven, perhaps, by the recent explosion in costs of medical care, and over 1,750 drug recalls reported by the FDA in 2009 alone.

Conventional therapeutic vaporizers typically include a heater configured to vaporize a therapeutic material and form a vaporized gas, and a tube from which a user can inhale the vaporized gas. Some vaporizers are configured to be connected to a vaporizer bag to receive vapors therefrom. Some vaporizer valves can affect flow into such a vaporizer bag. However, conventional vaporizers, vaporizer bags, and vaporizer valves suffer from any of a number of drawbacks. Notwithstanding the various efforts in the prior art, there remains a need for improved therapeutic vaporizers, bags, and valves.

SUMMARY

Some embodiments described herein generally relate to devices for vaporizing therapeutic materials. In some embodiments, the devices disclosed herein improve upon or overcome flaws and deficiencies in existing devices that have been recognized by the instant inventors. Specifically, some existing devices are unsightly, large, cumbersome, inefficient, expensive, and/or difficult to use. Furthermore, some devices also have limited control of the vaporization process, and thus produce a poor quality of therapeutic gas. Some conventional devices also include bulky accessories attached to the heater unit that can become tangled, or if detachable, lost. Some embodiments disclosed and described herein overcome the various drawbacks and deficiencies, for example, by being simpler to use, while providing a higher quality therapeutic gas. Some embodiments herein relate to a bag attachment system that captures the vaporized gas from which the user can subsequently control the release of the vaporized gas for inhalation. Some embodiments relate to a vaporizer bag attachment system with a valve to control flow of gas to and from a bag. Some embodiments relate to a vaporizer attachment system that includes a transversely-actuated duck-bill valve. The attachment system can include a unitary, monolithic, compact, rugged design that includes a mouthpiece, body and valve, in some embodiments, without additional components other than a coupling to connect the body of the system to a bag. The resulting compact, one-piece design, is comfortable, easy to use, easily cleaned, rugged, and free of additional loose parts that can be. The system can be durable, resistant to high temperature, resistant to leaking when attached to a bag, and/or simple and intuitive to operate. The attachment systems described herein can include a valve that automatically closes when removed from a therapeutic vaporizer, but without requiring additional, external components to reopen the valve and inhale vapors from a bag attached to the attachment system. The attachment systems herein include a valve that can be manually opened by a user, including a physically impaired user, without additional external components, such as an external, separate mouthpiece. The attachment systems which include some components with a simple, unitary construction, reduces production costs, prevents loss of components, reduces replacement costs, and reduces environmental impact.

In one embodiment, a therapeutic vaporizer is provided. The therapeutic vaporizer can include, for example, a housing, a heater, and at least one accessory-receiving element. The housing can include, for example, a first housing portion and a second housing portion configured to form an inner cavity. The first and second housing portions may be configured, for example, to movably engage and disengage with respect to each other between a closed and open position, respectively. At least a portion of the inner cavity may be enclosed when the first and the second housing portions are in the closed position, for example. The heater can be configured, for example, to at least partially vaporize a therapeutic material. The at least one accessory-receiving element may be positioned, for example, at least partially within the portion of the inner cavity. The accessory-receiving element can be configured, for example, to receive at least one accessory within the inner cavity when the first and second housing portions are in the closed position.

In another embodiment, a therapeutic vaporizer is provided. The therapeutic vaporizer can include, for example, a housing, a gas flow device, a heating element, and a bowl. The housing may include, for example, a first housing portion and a second housing portion configured to form an inner cavity. The first and second housing portions may be configured, for example, to movably engage and disengage with respect to each other between a closed and open position. The heating element can be configured, for example, to receive and selectively heat a gas flowed from the gas flow device. The bowl may include, for example, an inlet and an outlet in fluid communication with an inner bowl cavity. The inner bowl cavity may be configured to receive gas through the inlet from the heating element, for example. At least one of the first and second housing portions may include, for example, a housing channel configured to fluidly engage with the bowl outlet when the first and second housing portions are in a closed position. The housing channel can be configured, for example, to fluidly disengage with the bowl outlet when the first and second housing portions are in an open position.

In yet another embodiment, a therapeutic vaporizer is provided. The therapeutic vaporizer can include, for example, a housing, a gas flow device, a heater, a bowl, a first temperature sensor, a second temperature sensor, and a temperature controller. The gas flow device may be contained within the housing, for example. The heater can be contained within the housing, for example. The heater can include, for example, a chamber and a heating element configured to selectively heat a gas flowed from the gas flow device and through the chamber. The bowl may include, for example, an inner bowl cavity comprising a therapeutic material support, an inlet providing fluid communication between the inner bowl cavity and the chamber, and an outlet providing fluid communication from the inner bowl cavity. The first temperature sensor may be configured, for example, to detect a first temperature proximate to or within a portion of the heater. The second temperature sensor may be configured, for example, to detect a second temperature proximate to or within a fluid pathway formed downstream of the heater. The temperature controller can be associated, for example, with the first and the second temperature sensors and the heating element for controlling the temperature of a gas flowed through the bowl cavity.

In yet another embodiment, a method of providing a therapeutic gas is provided. The method can include, for example, providing a therapeutic vaporizer that can include, for example, a housing and a gas flow device, a heater, a first therapeutic material support and a second therapeutic material support. At least one of the first and second material supports can be positioned, for example, at least partially within the housing. The method can include, for example, forming an aromatic therapeutic gas by flowing a gas with the gas flow device through or proximate to a first therapeutic material that is supported by the first therapeutic material support. The method may include, for example, forming a vaporized therapeutic gas by one or more of: flowing a gas through the heater to form a heated gas and flowing the heated gas through or proximate to a second therapeutic material that is supported, for example, by the second therapeutic material support.

In some embodiments, a therapeutic vaporizer inhalation bag attachment system with an integrated valve is provided. The attachment system includes a body, a bag coupling, and a duck-bill valve. The body comprises a lumen extending between a first opening at a first end of the body and a second opening at a second end of the body. The bag coupling is configured to attach an inhalation bag to the second end of the body. The duck-bill valve is positioned within the lumen and configured to move between a first position which allows flow of vapor through the lumen in a first direction extending from the first opening to the second opening, and a second position which prevents substantial flow of vapor through the lumen in a second direction from the second opening to the first opening. The valve comprises two flaps extending within the lumen inwardly from an inner sidewall of the body, wherein a distal end of the flaps form a seal to prevent the substantial flow of vapor in the second flow direction.

In some embodiments, the flaps extend from the inner sidewall of the body in the first direction at a non-orthogonal angle. In some embodiments, the non-orthogonal angle comprises an angle greater than approximately 10 degrees and less than approximately 80 degrees.

In some embodiments, the valve is configured to move to the first position and allow flow in the second direction when a protrusion is extended through the first opening and through the distal end of the flaps and automatically return to the second position when the protrusion is removed from the first opening. In some embodiments, the body includes a lip seal extending from an inner wall of the body into the lumen, the lip seal configured to engage with the protrusion when the protrusion is extended through the first opening.

In some embodiments, the body and valve are configured such that the distal ends of the flaps separate and move the valve from the second position to the first position in response to an inwardly transverse force. In some embodiments, the body and valve are configured such that the distal ends of the flaps separate and move the valve from the second position to the first position in response to an inwardly transverse force of between approximately 0.5 and 10 pounds.

In some embodiments, the body and valve comprise a unitary structure and a common material.

In some embodiments, the body and valve comprise a flexible polymer.

In some embodiments, the valve consists essentially of the two flaps.

In some embodiments, the attachment system does not include a spring.

In some embodiments, the first end of the body comprises a mouthpiece. In some embodiments, the mouthpiece comprises at least one of a concavity or a flange.

In some embodiments, the attachment system further comprises the inhalation bag. In some embodiments, a capacity of the bag is between approximately ⅓ to 2 times the total average lung capacity of an adult human.

In some embodiments, at least one of the body and valve comprise a material resistant to a temperature of at least approximately 120° C. In some embodiments, at least one of the body and valve comprise a material resistant to a temperature of approximately 300° C. or less.

In some embodiments, the attachment system further comprises a magnetic attachment portion attached to the first end of the body.

In some embodiments, the attachment system further comprises a plurality of cooling ribs extending at least partially along an outer surface of a sidewall of the body.

In some embodiments, a therapeutic vaporizer is provided that comprises the attachment system. In some embodiments, the therapeutic vaporizer comprises a bowl, wherein the bowl comprises a bowl magnetic attachment portion configured to magnetically attach to a corresponding vaporizer magnetic attachment portion of the vaporizer. In some embodiments, at least one of the bowl magnetic attachment portion and the vaporizer magnetic attachment portion comprises a high-temperature magnetic material. In some embodiments, the attachment system further comprises a magnetic attachment portion attached to the first end of the body and configured to magnetically attach to the bowl, wherein magnetic force between the magnetic attachment portion of the bowl and the vaporizer magnetic attachment portion is greater than the magnetic force between the magnetic attachment portion of the attachment system and the bowl.

In some embodiments, a method of using an inhalation bag attachment system for a therapeutic vaporizer is provided. In some embodiments, the method comprises placing an inhalation bag attachment system in fluid communication with an outlet of a therapeutic vaporizer. In some embodiments, the method comprises forming a therapeutic vapor by heating therapeutic materials within the therapeutic vaporizer. In some embodiments, the method comprises flowing the therapeutic vapor through the outlet and into the inhalation bag attachment system in a first direction. In some embodiments, the method comprises removing the inhalation bag attachment system from the outlet, wherein removing comprises substantially preventing flow through an opening of the inhalation bag attachment system in a second, opposed direction with a duck-bill valve.

In some embodiments, placing the inhalation bag attachment system in fluid communication with the outlet of the therapeutic vaporizer comprises inserting a protrusion into the valve to open the valve. In some embodiments, removing comprises disengaging the protrusion from the valve to close the valve. In some embodiments, inserting the protrusion comprises engaging the protrusion with a lip seal extending from an inner wall into an inner lumen of the valve.

In some embodiments, the method further comprises applying a transverse force to the valve to open the valve and allow flow through the valve in both the first and second directions; and removing the force from the valve to automatically close the valve to prevent flow through the valve in the second direction.

In some embodiments, placing the inhalation bag attachment system in fluid communication with the outlet of the vaporizer comprises magnetically coupling the opening of the inhalation bag attachment system with the outlet of the vaporizer.

In some embodiments, flowing vapor through the outlet comprises flowing vapor through an outlet of a vaporizer bowl, further comprising magnetically coupling the bowl with the vaporizer.

In some embodiments, flowing the therapeutic vapor through the outlet into the inhalation bag attachment system comprises filling an inhalation bag with a capacity between approximately ⅓ to 2 times the total average lung capacity of an adult human In some embodiments, flowing the therapeutic vapor through the outlet into the inhalation bag attachment system comprises flowing a therapeutic vapor at a temperature of at least approximately 120° C.

In some embodiments, flowing the therapeutic vapor through the outlet into the inhalation bag attachment system comprises flowing a therapeutic vapor at a temperature of approximately 300° C. or less.

In some embodiments, the method of using an inhalation bag attachment system can further include attaching the valve to the opening of the inhalation bag, wherein attaching comprises: engaging an inner bag collar with an outer bag collar, with the bag opening positioned between the two collars to allow fluid communication from the bag opening through the two collars; and engaging the two collars with a body, wherein the valve is positioned within a lumen of the body.

In some embodiments, engaging the two collars with the body comprises inserting the body into the two collars.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the apparatuses, devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

These and other features, aspects and advantages are described herein with reference to drawings of preferred embodiments, which are intended to illustrate and not to limit the inventions.

FIG. 1C illustrates a side exploded view of an example of a non-limiting embodiment of the vaporizer shown in FIGS. 1A and 1B.

FIG. 8 is a side perspective view of an example of a non-limiting embodiment of an inhalation tube.

FIG. 14A is a cross-sectional perspective view of an embodiment of an attachment system with a valve for an inhalation bag.

FIGS. 14B-14C are bottom cross-sectional views of an embodiment of the attachment system shown in FIG. 14A.

FIGS. 17A-17D are various views of an embodiment of an upper tray for a vaporizer.

DETAILED DESCRIPTION

Figure 1B:
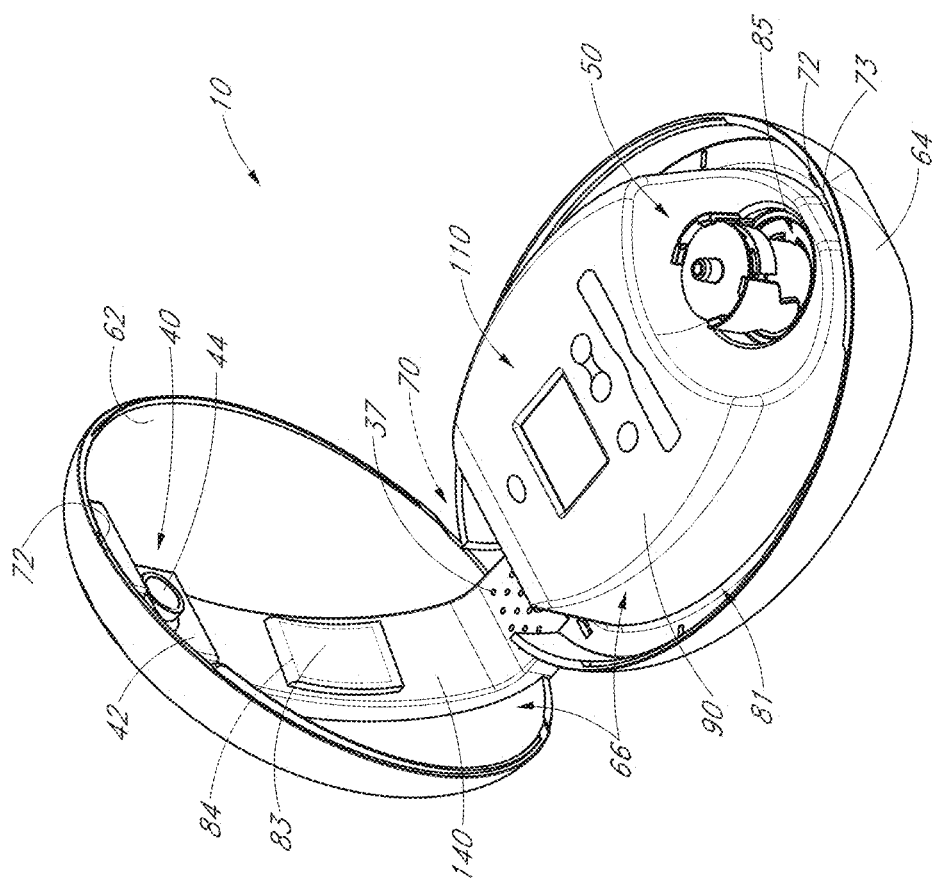
FIG. 1B illustrates a side perspective view of an example of a non-limiting embodiment of the vaporizer of FIG. 1A in an open position.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

As mentioned above, conventional vaporizers are unsightly, large, cumbersome, inefficient, expensive, and difficult to use. Conventional vaporizers also include bulky accessories attached to the heater unit that can become tangled, or if detachable, lost. Thus, conventional vaporizers, and in particular, conventional vaporizers for therapeutic vapor, have not seen widespread acceptance.

The present disclosure provides simple, easy to use vaporizers with a variety of convenient features and therapeutic benefits. Some embodiments provide a vaporizer with a heater, a gas-flow device, and one or more therapeutic material supports configured to support one or more therapeutic materials. Some embodiments provide a first material support to support an aromatic therapeutic material for aromatherapy, and a second material support to support a vaporizable therapeutic material that can be vaporized by a heated gas to provide vapor therapy. Thus, some embodiments provide both aromatherapy and vapor therapy in a single device, either simultaneously, or at substantially different times, unlike conventional therapeutic devices which provide either vapor therapy or aromatherapy, but not both.

As used herein, "vaporization" is defined as the transition of matter from a solid or liquid phase into a gaseous or vapor phase, such as the release of volatiles from a volatile substance. "Vaporization" should not be construed to mean without any additional processes; for example, "vaporization" can include some amount of combustion of matter. Thus, "vapor" is not to be construed as a vaporized gas without suspended particles or other contaminants, such as gaseous or particulate emissions from combustion or partial combustion of a material.

The vaporizer can include a housing that forms an inner cavity in which one or more accessories can be at least partially enclosed or concealed from view. For example, two or more housing portions can be provided that are movable between an open and closed position, for example, to provide selective access to at least a portion of the inner cavity. This can allow one or more vaporizer accessories to be at least partially contained or concealed within the inner cavity (for example, when the vaporizer is closed). Such accessories can include, for example, a container (for example, a bowl with a vaporizable material support to support vaporizable material), an inhalation tube, and/or an inhalation bag, any of which may be used during vaporization, as described further herein. The accessories can be at least partially removable from the vaporizer. This is a departure from conventional vaporizable devices, in which accessories generally are not removable, and/or are not capable of being stored with or within the device, and thus become separated from the device and lost. Thus, some embodiments of the vaporizers described herein provide a fully self-contained vaporizer, including one or more accessories that can provide both functionality and a desired aesthetic, neither of which are provided in unsightly and less functional conventional vaporizers.

In some embodiments, the vaporizers can include an optional controller and/or a user interface to provide additional control over various aspects of the vaporizer and its processes. For example, a user may want to control the timing, temperature, pressure, flow rate, and/or other parameters related to the vaporization and/or aromatherapy that can be provided by the device. In some embodiments, one or more sensors can be provided to provide feedback to the user (for example, through the user interface, for example, for open loop control) and/or to provide feedback to the controller (for example, to provide closed-loop control) for these various parameters of the vaporizer processes (for example, vapor therapy and/or aromatherapy). Sensors can be provided that measure, for example, the flow rate, temperature, density, pressure, etc., of vaporized or non-vaporized gas within the device, or other components of the device itself (for example, the temperature of the heater, therapeutic material support, etc.). Some embodiments provide one or more sensors that quantitatively or qualitatively analyze the constituents of the gas flowing through the vaporizer (for example, the therapeutic gas flowing from the therapeutic material support), to improve the quality of the gas and thus the therapeutic benefits of the vaporizer. In some embodiments, the vaporizers described herein can provide "metered dose delivery" to control, for example, the amount of vaporized therapeutic gas to a patient (for example, a prescribed amount of therapeutic gas). The aforementioned aspects of the vaporizers described herein are very different from conventional therapeutic devices, which provide limited to no control over such process parameters. Some control benefits of embodiments of the vaporizers described herein can include accelerated preheating (less than 30 seconds in some embodiments), and improved response time and accuracy during vaporization.

Although embodiments of the technology have been disclosed in the context of certain examples, it will be understood by those skilled in the art that the present technology may extend beyond the specifically disclosed embodiments to other alternative embodiments and/or uses of the inventions and obvious modifications and equivalents thereof. In addition, while several variations of the technology have been shown and described in detail, other modifications, which are within the scope of the technology, will be readily apparent to those of skill in the art based upon this disclosure. It is also contemplated that various combinations or sub-combinations of the specific features and aspects of the embodiments may be made and still fall within the scope of the technology. It should be understood that various features and aspects of the disclosed embodiments can be combined with or substituted for one another in order to form varying modes of the disclosed inventions. Additionally, it will be understood that variations in the shapes of the vaporizer and its components described herein can provide a similar functional result.

Figure 1A:
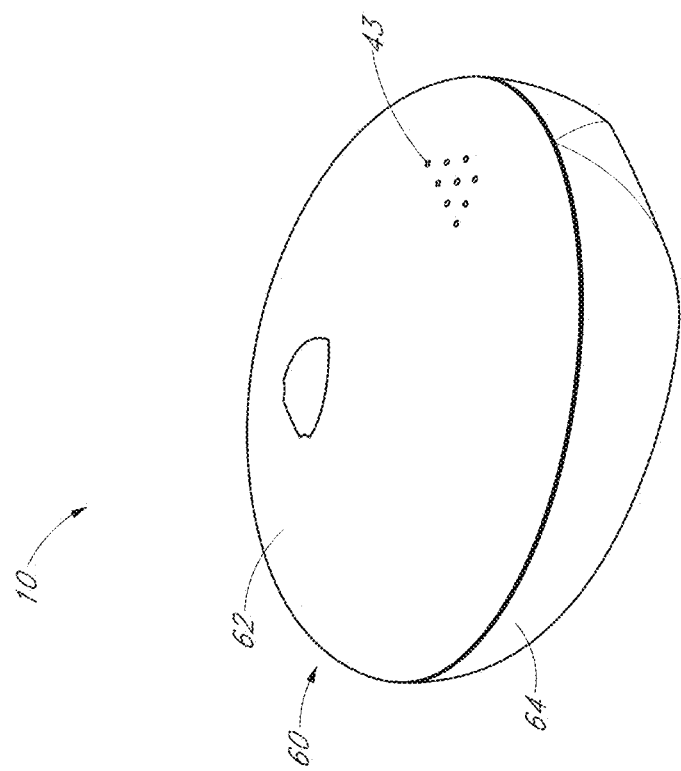
FIG. 1A illustrates a side perspective view of an example of a non-limiting embodiment of a therapeutic vaporizer in a closed position.

FIG. 1A illustrates a side perspective view of an embodiment of a therapeutic vaporizer 10 in a closed position. FIG. 1B illustrates a side perspective view of an embodiment of the vaporizer 10 of FIG. 1A in an open position. FIG. 1C illustrates a side exploded view of an embodiment of the vaporizer 10 shown in FIGS. 1A and 1B.

Referring to FIGS. 1A-1C, the exploded view of FIG. 1C shows that the vaporizer 10 can include a heater 20 and a gas-flow device 30, which can be configured to selectively heat and/or flow a gas through one or more therapeutic portions of vaporizer 10. For example, vaporizer 10 can selectively flow gas (for example, heated or non-heated) through a first therapeutic material support 40, to provide aromatherapy, and/or a second therapeutic support attached to a bowl 50, to provide vapor therapy, as will be described in further detail below. It will be understood, as used herein, "attach," "attached to," "couple," "coupled to," or similar terms can mean directly attached or coupled to, or indirectly attached or coupled to (for example, with one or more intermediary structures), unless otherwise specified. Vaporizer 10 can include an optional controller 100 and/or a user interface 110, to provide additional functionality and control over various aspects of vaporizer 10.

The vaporizer 10 can include a housing 60 configured to form an inner cavity 66. Housing 60 can include one or more portions configured to engage with each other, such as a first (for example, upper) housing portion 62 configured to engage with a second (for example, lower) housing portion 64. Housing portions 62, 64 can comprise any of a variety of structures capable of supporting and/or at least partially enclosing at least a portion of one or more components and/or accessories related to vaporizer 10 within cavity 66. Thus, housing portions 62, 64 are not limited to a shell-like structure (as depicted in the non-limiting example). For example, housing portions 62, 64 can include portions with holes, apertures, mesh, caging, or other features that may support, protect, and/or at least partially enclose one or more components of vaporizer 10 there within, or to provide other functionality.

In some embodiments, the housing portions 62, 64 can be configured to be movable between a closed position (FIG. 1A) and an open position (FIG. 1B). Such a configuration can allow at least a portion of the inner cavity 66 to be enclosed when the housing portions 62, 64 are in the closed position. As used herein, "enclosed" can mean partially or completely enclosed. "Enclosed" can mean, for example, air or vacuum sealed, or allowing (for example, freely allowing, or selectively allowing and restricting) some airflow to and from cavity 66. In some embodiments, "enclosed" can mean, for example, at least partially enclosing at least a portion of a component from view within the portion of inner cavity 66, without concealing the portion of the component (for example, if housing portions 62, 64, and/or one or more intermediary structures, comprise a substantially transparent or translucent material, or if housing portions 62, 64 comprise insufficient structure to conceal the portion of the component). In some embodiments, "enclosed" can mean, for example, at least partially concealing at least a portion of a component from view within a portion of inner cavity 66 (for example, if housing portions 62, 64 and/or one or more intermediary structures comprise a substantially opaque material with sufficient structure to conceal the portion of the component). In some embodiments, "enclosed" can mean, for example, concealing a substantial portion of a component from view such that the structure and/or purpose of the component cannot be determined by an individual viewing vaporizer 10 in the closed position.

The housing portions 62, 64 can be coupled (for example, permanently, semi-permanently, or removably coupled) to each other with one or more attachment elements, such as a latch, fastener, magnet, clip, button, snap, lock, hook, hook/loop system (for example, Velcro), press fit, and the like, or combinations thereof. In some embodiments, the one or more attachment elements used to couple housing portions 62, 64 can comprise a rotational element or rotational coupling device, such as a hub, lug, bearing, bushing, hinge, pin, ball and pinion, axle, rotational joint, and the like, or combinations thereof, that allows housing portions 62, 64 to pivot with respect to each other. In the illustrated embodiment, vaporizer 10 includes a hinge 70 that allows housing portions 62, 64 to pivot with respect to each other, and to move between an open and closed position (see also, for example, FIG. 2).

Figure 3:
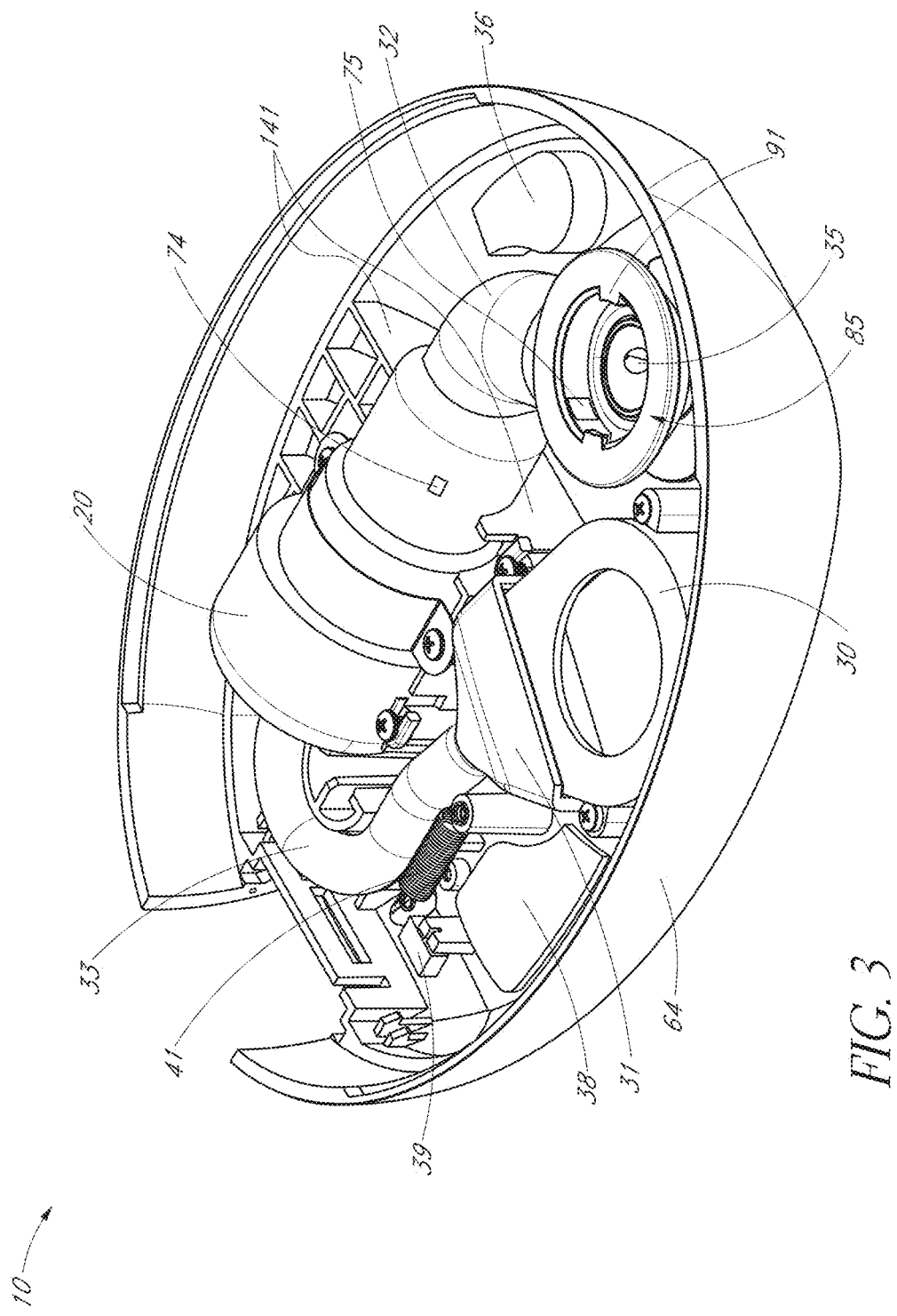
FIG. 3 is a side perspective view of an example of a non-limiting embodiment of a lower portion of a vaporizer.
Figure 4:
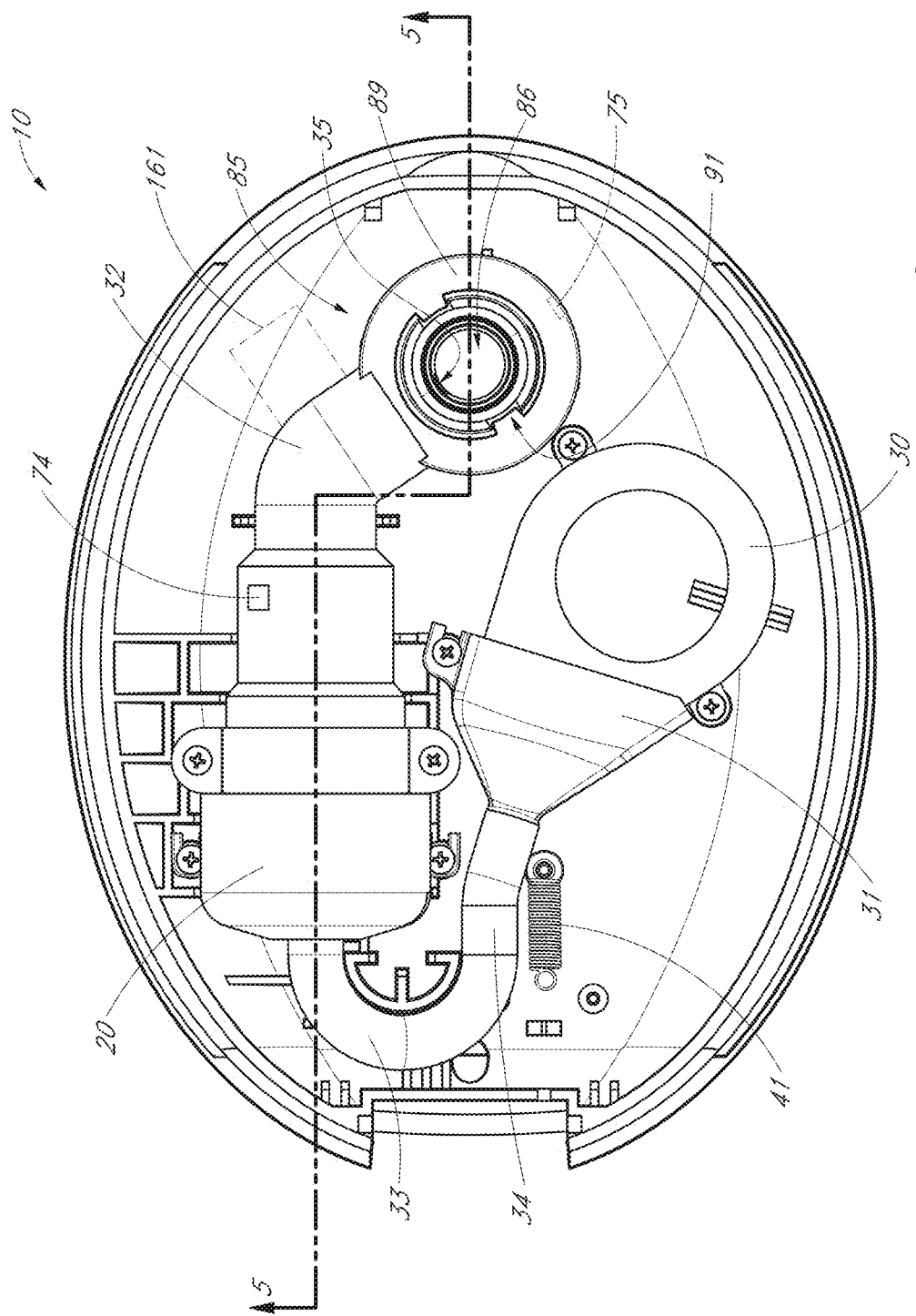
FIG. 4 is a top view of an example of a non-limiting embodiment of a lower portion of the vaporizer of FIG. 3.

In some embodiments, vaporizer 10 optionally can include a damper, shock, spring, or similar biasing mechanism 41 supported by at least one of the first and second housing portions 62, 64 (FIGS. 3-4). The biasing mechanism 41 can be configured to resist motion of the first and second housing portions 62, 64 in at least one direction when the first and second housing portions 62, 64 are pivoted about the rotatable coupling device 70 (FIGS. 1B-1C) between an open and closed position as illustrated in FIGS. 1A-1B.

Vaporizer 10 can include an attachment element to secure (for example, removably secure) housing portions 62, 64 in a closed position, such as a latching element 72 (FIG. 1B). In some embodiments, latch 72 can be a lockable latch that implements a key, keypad, or other mechanical or electronic security device to allow vaporizer 10 to be moved from a closed (for example, locked) to an open (for example, unlocked) position.

As described above, and referring to FIG. 1C, one or more optional openings, such as opening 63, can be extended through housing portions 62, 64 to provide additional functionality to vaporizer 10. Opening 63 can be configured to allow a user to view and/or operate the user interface 110 and/or control system 100 when the housing portion 62, 64 are in a closed position. In other embodiments, user interface 110 and/or control system 100 can be substantially concealed or enclosed within a portion of cavity 66 when the housing portions 62, 64 are in a closed position.

In the illustrated embodiment, for example in FIGS. 1B and 1C, opening 63 is configured to receive a portion of an optional light assembly 61. Lighting assembly 61 can comprise a simple lighting element 67, or can include an optional control circuit (for example, microchip, controller, etc.) 69 in communication with controller 100, to provide more complex functionality. Lighting assembly 61 can include an optional translucent or transparent window or lens 65 configured to prevent damage to the remainder of lighting assembly 61. In some embodiments, lens 65 seals opening 63. Light assembly 61 can be configured to provide light in a number of different wavelengths (for example, colors), patterns, frequencies, etc. Light assembly 61 can be controlled with control circuit 69 such that lighting element 67 activates and deactivates (for example, flashes) in various patterns and frequencies. Lighting assembly 61 can provide one or more of these various lighting features to vaporizer 10, either for aesthetic purposes (for example, ambient lighting during use of the vaporizer 10 in an open or closed position), or to indicate functionality of an aspect of vaporizer 10. For example, light assembly 61 may be configured to activate lighting element 67 to indicate vaporizer 10 is in use, and deactivate lighting element 67 to indicate vaporizer 10 is not in use. In some embodiments, control circuit 69 can include additional or alternative functionality to that of merely controlling light assembly 61. For example, controller 69 can include devices that provide one or more of voice control (for example, with an integrated microphone), motion activation, a touch sensor for external touch activation, and/or a wireless transmitter or transceiver, to provide additional functionality for the control of vaporizer 10.

Vaporizer 10 can comprise an optional mezzanine 90 attached to at least one of the first and second housing portions 62, 64 within a portion of inner cavity 66. The mezzanine 90 can provide support to one or more other components of vaporizer 10, such as control system 100 and/or user interface 110. In some embodiments, the mezzanine 90 can be configured to divide the interior of housing 10 into two or more cavity sections. For example, referring to FIGS. 1B, 1C, and 2, the mezzanine 90 can divide (for example, partially, or completely divide) the portion of the inner cavity 66 into a first cavity section 66a and a second cavity section 66b. The mezzanine 90 can be configured such that the second cavity section 66b is partially or completely concealed from view when the first and the second housing portions 62, 64 are in the open position as illustrated, for example, in FIG. 1B. For example, mezzanine 90 can be configured to conceal one or more components, such as the heater 20, control system 100, and/or gas flow device 30, even when the housing portions 62, 64 is in the open position. In some embodiments, the mezzanine 90 can include one or more openings 91 (FIG. 1C), to provide viewing and/or access to user interface 110 from a first side of mezzanine 90, when interface 110 is mounted on an opposed side of mezzanine 90.

Figure 2:
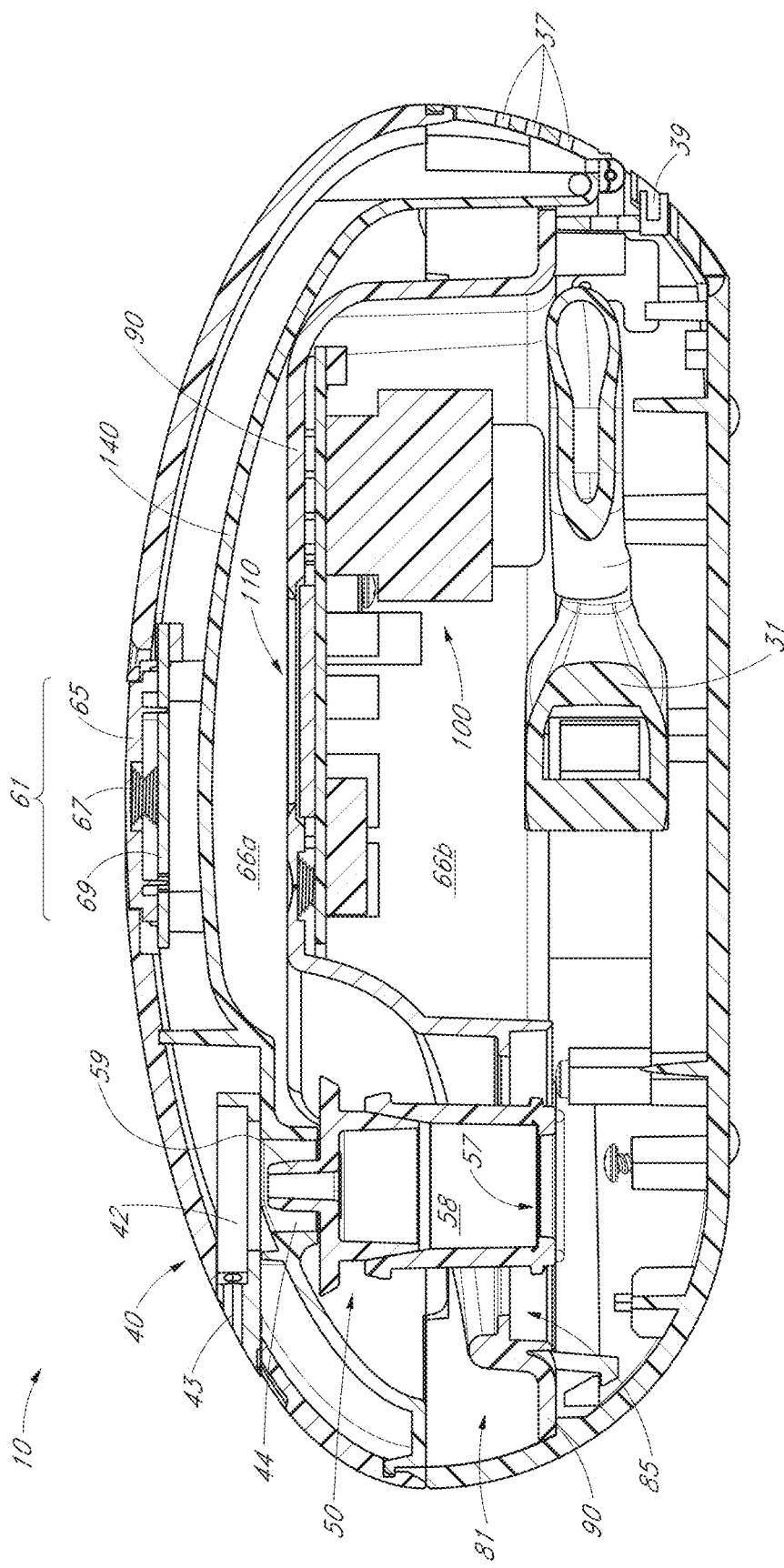
FIG. 2 is a side cross-sectional view of an example of a non-limiting embodiment of the vaporizer shown in FIGS. 1A-1C.

The mezzanine 90 is not limited to the configuration shown in FIGS. 1B, 1C and 2, and can be any planar, non-planar, symmetric, asymmetric, regular, or irregular shape suitable to provide the aforementioned at least partial support and/or at least partial concealment of one or more components of vaporizer 10. The mezzanine 90 can extend across some, most, or substantially the entirety of the length and/or width of housing portions 62, 64 and/or cavity 66, and can include similar or different thicknesses across said length and/or width.

Vaporizer 10 can include one or more accessory-receiving elements or portions, such as a tube-receiving element 81, an inhalation bag-receiving element 83, a bowl-receiving element or receptacle 85, and/or other types of accessory-receiving portions as described further herein, or known, configured to receive one or more accessories at least partially, or completely, within a portion of the inner cavity 66. As used in this context, "receive" can be defined as at least partially attach to (for example, removably or permanently) and/or can be defined as providing a space within a portion of inner cavity 66 within which an accessory can be stored, with or without partial or complete attachment of a portion of the accessory to another portion of vaporizer 10. The accessory-receiving elements described herein can comprise any of a number of different sizes and shapes configured to receive any of a number of different accessories. For example, the accessory-receiving elements can comprise any of the attachment elements described herein or known in the art for attaching housing portions 62, 64 to each other, but configured to attach an accessory to a portion of vaporizer 10. Alternatively or additionally, the accessory-receiving elements can comprise a pocket, groove, flap, or other structure that can receive and provide a defined space within cavity 66 in which an accessory can be stored. The accessory-receiving elements can be positioned anywhere within cavity 66 suitable for receiving and/or storing an accessory, and are not limited to the illustrated embodiments described herein.

Referring to FIGS. 1B, 1C and 2, in some embodiments, the accessory-receiving element can comprise an inhalation tube-receiving element 81 (FIGS. 1B and 2) configured to receive an inhalation tube 82 (FIGS. 1C and 8). Without being limited thereto, the tube-receiving element 81 as depicted is a channel, groove or space with the cavity 66, specifically around at least part of the perimeter of the cavity 66 adjacent to the edge of the mezzanine 90. Inhalation tube 82 can comprise any of a number of shapes and configurations, and generally includes a flexible tube-like conduit 82a and a mouthpiece 82b, configured to be integrally or separately formed (FIG. 8).

The tube-receiving element 81 can have other shapes and configurations. For example, the tube-receiving element 81 can include any of accessory-receiving elements described herein, or otherwise known in the art, suitable for receiving the inhalation tube 82. For example, the inhalation tube 82 can be coiled, folded, compacted, or otherwise adjusted, to be received by a number of differently-shaped tube-receiving elements. Referring again to FIGS. 1B, 1C and 2, in the illustrated embodiment, the element 81 comprises a groove extending at least partially around an inner perimeter of at least one of the first and second housing portions 62, 64. The groove 81 can extend into housing portions 62, 64; in the illustrated embodiment, the groove 81 extends between a portion of the mezzanine 90 and at least one of the first and second housing portions 62, 64 (FIGS. 1B and 2).

In some embodiments, the accessory-receiving element can comprise an inhalation bag-receiving element 83 (FIG. 1B) configured to receive an inhalation bag 84 (FIGS. 1B; 7A-7C). Again referring to FIG. 1B, the bag-receiving element 83 can include any of the aforementioned configurations of accessory-receiving elements, or otherwise known in the art, suitable for receiving the bag 84 (shown non-deployed or folded in FIG. 1B). The bag-receiving element 83 can include, for example, a clip, groove, pocket, flap, or any other suitable structure. The bag-receiving element 83 can be positioned, for example, proximate to, or attached to, an inner surface of housing portions 62, 64.

Figure 6A:
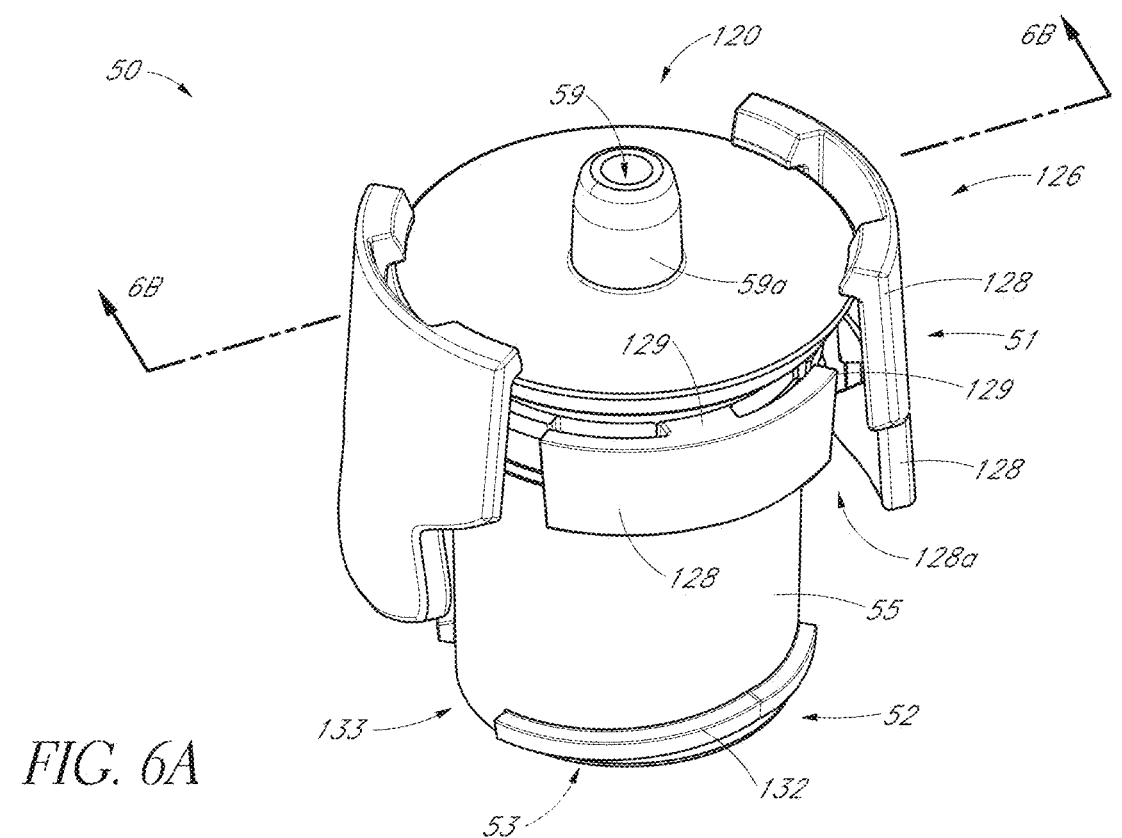
FIG. 6A is a side perspective view of an example of a non-limiting embodiment of a bowl for supporting vaporizable material.
Figure 6B:
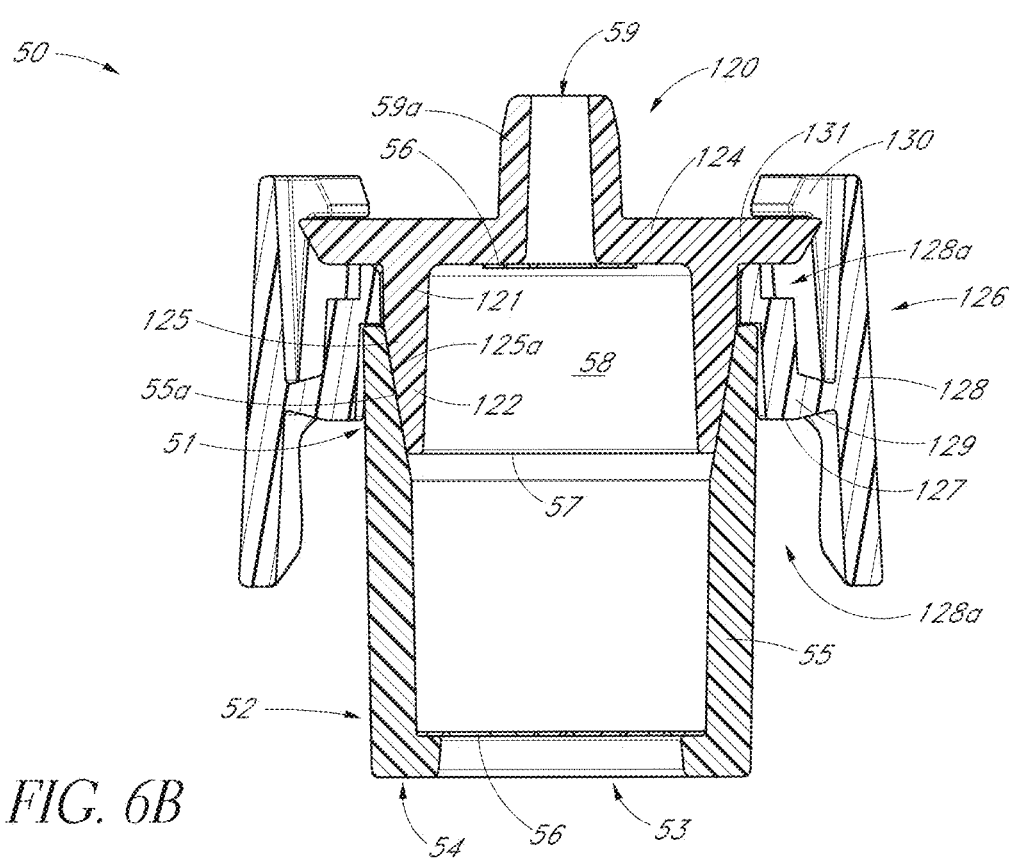
FIG. 6B is a side cross-sectional view of an example of a non-limiting embodiment of a bowl of taken along line 6B-6B of FIG. 6A.
Figure 7A:
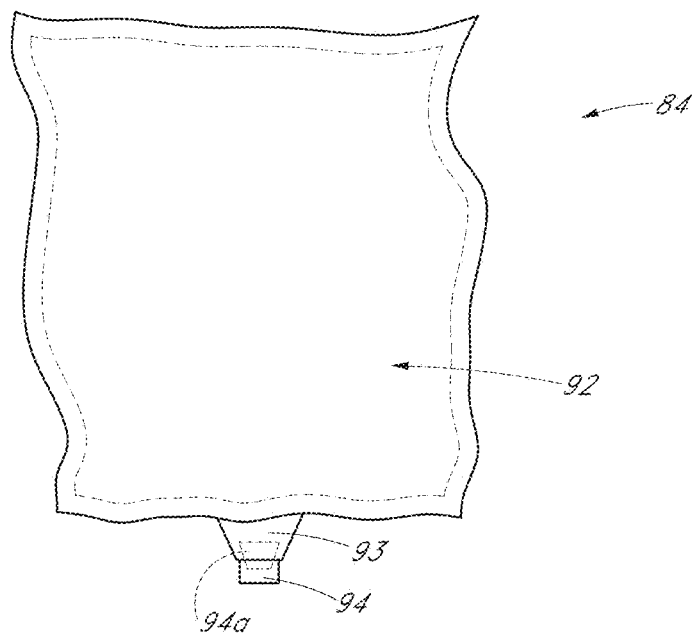
FIG. 7A is a side view of an example of a non-limiting embodiment of an inhalation bag.
Figure 7B:
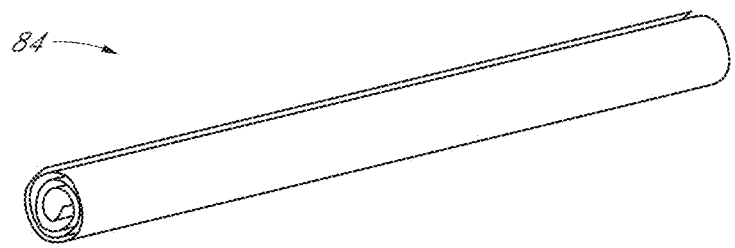
FIGS. 7B and 7C are side views of an example of a non-limiting embodiment of an inhalation bag shown in a rolled and folded position, respectively.
Figure 7C:
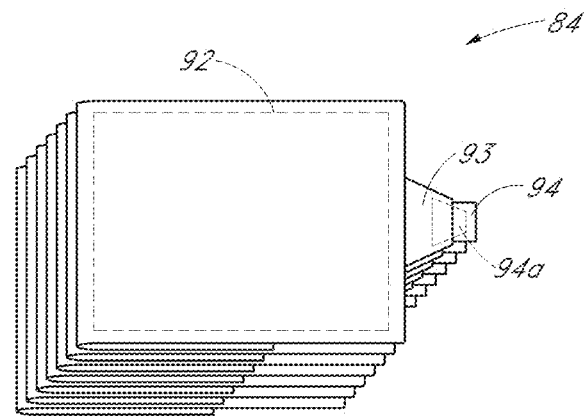

Referring briefly to FIGS. 7A-7C, the inhalation bag 84 can be folded (FIG. 7C), rolled (FIG. 7B), or otherwise compacted such that it can be more easily received by a bag-receiving element of a number of different shapes. The inhalation bag can comprise any of a number of different flexible, semi-flexible, or semi-rigid materials suitable to hold a gas with minimal leakage, including, for example, a heated gas of at least partially vaporized material. The inhalation bag 84 can be any of a variety of shapes and configurations suitable to form an inner volume 92 for containing a gas. Bag 84 can include a bag opening 93 configured to allow gas to flow into and out of volume 92. In some embodiments, a separate inlet and outlet can be employed to allow flow into and out of bag 84, respectively. Opening 93 can include an optional fitting or connector 94 configured to attach bag 84 to outlet 59 of bowl 50 (for example, FIGS. 6A, 6B), and to fluidly communicate and receive vaporized gas there from. Opening 93 and/or connector 94 can also provide a mouthpiece for a user (for example, patient) to receive (for example, inhale) vaporized gas contained within bag 84. In some embodiments, connector 94 can include a valve 94a in fluid communication with the connector 94, the valve configured to allow selective flow of gas to and/or from the volume or interior 92 of bag 84. In some embodiments, the valve 94a can be configured to freely allow gas flow into the interior of the bag 84 from the bowl 50 when the bag 84 is attached to the bowl outlet, and to restrict gas flow from the bag when the valve 94a is in a quiescent state and the bag is removed from the bowl 50. In a preferred embodiment, connector 94 can include, for example, a one way valve, or even more preferably, a duck-bill one-way valve, that allows a user to selectively control gas flow out of bag 84 in a first direction, while allowing substantially free flow of gas into bag 84 in a second direction (for example, after exceeding a cracking pressure of the valve in the second direction). In some embodiments, the valve 94a can be configured to freely allow gas flow from the bag 84 when the valve is in an activated state and the bag is removed from the bowl 50. Valve 94a can be integrally or separately formed with respect to connector 94, and can extend partially or completely into or through opening 93, or can be positioned on either side of opening 93 (for example, within an interior 92, or exterior to bag 84).

In some embodiments, the accessory-receiving element can be configured as or can comprise a bowl-receiving element, such as a bowl receptacle 85 configured to receive the bowl 50. To more fully understand bowl receptacle 85, bowl 50 will be described presently.

Referring to FIGS. 6A and 6B, a container, receptacle, basin, or as used herein, "bowl" 50, is depicted, which can be used to receive heated gas and vaporize a therapeutic material supported or contained therein. The bowl 50 can include or be any of many shapes and materials capable of receiving, supporting, and/or vaporizing a therapeutic material. Bowl 50 can comprise one or more sidewalls, illustrated here as a sidewall 55, extending between an upper end 51 and a lower end 52 of bowl 50. At least one of upper end 51 and lower end 52 can be closed (for example, with a separate (for example, removable) or integral cover, cap or lid, such as a lid 120), to form an internal volume or plenum 58 within bowl 50. In the illustrative embodiment, the lower end 52 of bowl 50 can include a base 54. Base 54 can be positioned anywhere within an inner perimeter of sidewall 55 that forms an internal volume within bowl 50. Upper end 51 and/or lower end 52 can be open or can be closed. In the illustrated embodiment, lower end 52 is open, and comprises an opening or inlet 53, to facilitate the flow of gas into the internal volume of bowl 50. Inlet 53 can extend through base 54, as shown for illustrative purposes only, or can extend through another portion of bowl 50. Inlet 53 can comprise a single opening, or a plurality of apertures that allow gas to flow there through.

Inlet 53 can be positioned anywhere on bowl 50, such as through any portion of sidewall 55, base 54, upper end 51 or lower end 52. In some embodiments, an inlet can be provided that extends through a portion of lid 120.

Bowl 50 can include an outlet 59 to facilitate flow of gas from inner volume or plenum 58. Outlet 59 can be configured and positioned similar to that described herein for inlet 53. Preferably, outlet 59 is positioned on bowl 50, spaced from inlet 53, to allow gas to flow and mix within bowl 50. In the illustrated embodiment, outlet 59 can extend through lid 120. Outlet 59 can include a nipple, quick connect, barb, lure, or other type of fitting 59a, to allow inhalation bag 84, inhalation tube 82, and or an alternative or intermediary structure, to be connected (for example, removably) thereto. Outlet 59 can include a flow-control device, such as a fixed orifice or other flow restriction, to restrict flow from bowl 50, as described elsewhere herein.

Bowl 50 can include or have, for example, any of many different cross-sectional shapes, such as an approximately rectangular, elliptical, trapezoidal, circular, or any other regular or irregular shape that forms a hollowed, inner volume when extended longitudinally, to form an inner volume. The inner volume of bowl 50 can be the same or a different shape relative to the overall outer shape formed by the outer surfaces of bowl 50. The vertical longitudinal cross-section of the bowl 50 can have approximately straight and parallel sides, or substantially non-parallel or tapered portion, for example, to receive a portion of lid 120. The longitudinal cross-section of bowl 50 can comprise one or more portions along its longitudinal length with different widths or diameters.

Bowl 50 can be, for example, at least partially a rigid, semi-rigid, or semi-flexible material suitable to hold a therapeutic material and withstand the temperatures of a vaporization process (such as a process for vaporizing therapeutic materials), such as metal, glass, ceramic, or plastic. Bowl 50 can include, for example, an opaque, translucent, or transparent material. It will be understood that bowl 50 at least partially can comprise any combination of, and/or can be coated with, one or more of the aforementioned materials.

Lid 120 of bowl 50 can comprise an upper portion 121, lower portion 122, and sidewalls 125 that can be similar in size, shape, and/or function as upper portion 51, lower portion 52, and sidewalls 55 of bowl 50. Lid 120 can include a cover 124 from which sidewalls 125 extend. The inlet 53 and/or outlet 59 can extend through a portion of lid 120, such as upper portion 121, lower portion 122, sidewalls 125, or cover 124. A portion of lid 120 can be configured to engage (for example, removably) with the remainder of bowl 50, to form a substantially enclosed vaporization plenum 58. In the illustrated embodiment (for example, in FIG. 6B), lower portion 122 of lid 120 can engage with upper portion 51 to form plenum 58. Such engagement can be provided with any of a number of attachment mechanisms, such as threads, press fit, or other attachment mechanisms known or described herein. In the illustrated embodiment, the sidewalls 125 and 55 can include, for example, optionally tapered sections 125a and 55a, respectively, to provide some engagement there between.

Bowl 50 can include one or more handling members, including various surface textures, contoured shapes, and/or insulative structure to facilitate the handling of bowl 50. In the illustrated embodiment, bowl 50 includes one or more handling portions 126 configured to assist in the handling of bowl 50. Handling portion 126 can include an attachment portion 127 configured to attach to another portion of bowl 50, such as one or more of sidewalls 55, 125. One or more handles 128 can extend along an outer portion of bowl 50, such as one or more of an outer surface of sidewalls 55, 125, base 54, or lid 120. In the illustrated embodiment, handles 128 can extend along an outer surface of sidewalls 55 and 125, to allow a user to grasp an outer portion of bowl 50. Handles 128 can be separated from one or more of sidewalls 55, 125, base 54, and/or lid 120 with a strut 129 or similar structure, to form one or more gaps 128a between. Gaps 128a can provide increased cooling flow to handles 128 (for example, an inner surface facing sidewalls 55, 125), decreasing the temperature of handling portion 126. The temperature of handling portion(s) 126 can also be reduced because they are insulated from the heat flow from the bowl, due to the increased thermal path length through one or more of the attachment portion 127, strut 129, and/or handles 128, any one or more of which can be constructed of a material with low thermal conductivity. Such features can allow a user to grasp and use bowl 50 during or shortly after vaporization within plenum 58, without discomfort or injury.

In some embodiments, handling portion 126 can include one or more optional attachment elements 130 configured to attach lid 120 to the remainder of bowl 50. In the illustrated embodiment, elements 130 can comprise a tab configured to extend over and engage with a portion of cover 124 of lid 120. In some embodiments, cover 124 can include an optional outwardly-extending flange 131 to facilitate said engagement.

Referring to FIG. 6B, the bowl 50 can include a material support 57 with any of a number of different shapes and configurations suitable to support a therapeutic material within vaporization plenum 58. Material support 57 can at least partially extend from or at least partially be attached to sidewall 52, base 54, cover 124, sidewalls 125, and/or can be formed separately or with unitary construction with respect to these components. Material support 57 can be at least partially solid, and/or can include one or more apertures, to allow gas to flow there through. Material support 57 can be configured such that gas flows through or proximate to a therapeutic material supported by support 57. When such a gas is sufficiently heated by heater 20 (FIGS. 1A-5), the therapeutic material supported by support 57 can be vaporized, as described further herein.

Referring to FIG. 6B, bowl 50 optionally can include one or more filters 56 configured to filter gas flowing into plenum 58 (for example, through inlet 53), and/or gas flowing from plenum 58 (for example, from outlet 59). The filters 56 can comprise a rigid or semi-rigid screen or mesh-like structure, and/or other filter elements known in the art that can filter gas and withstand the vaporization temperatures within bowl 50. The filters 56 can be integrally formed with one or more components of bowl 50, such as cover 124, base 54, and/or sidewalls 55, 125, or can be a separate (for example, removable/replaceable) component.

Referring to FIGS. 1B-5, the therapeutic vaporizer 10 includes a bowl receptacle 85, which for example, can receive or support the bowl 50 within the vaporizer apparatus 10. The bowl receptacle 85 can include any of the accessory-receiving elements described herein, or otherwise known in the art, suitable for receiving the bowl 50. Bowl receptacle 85 can engage with or attach to (for example, removably) bowl 50 using any of the attachment elements known or described herein. The bowl receptacle 85 can be a similar or different shape than the bowl 50 described elsewhere herein.

Figure 5:
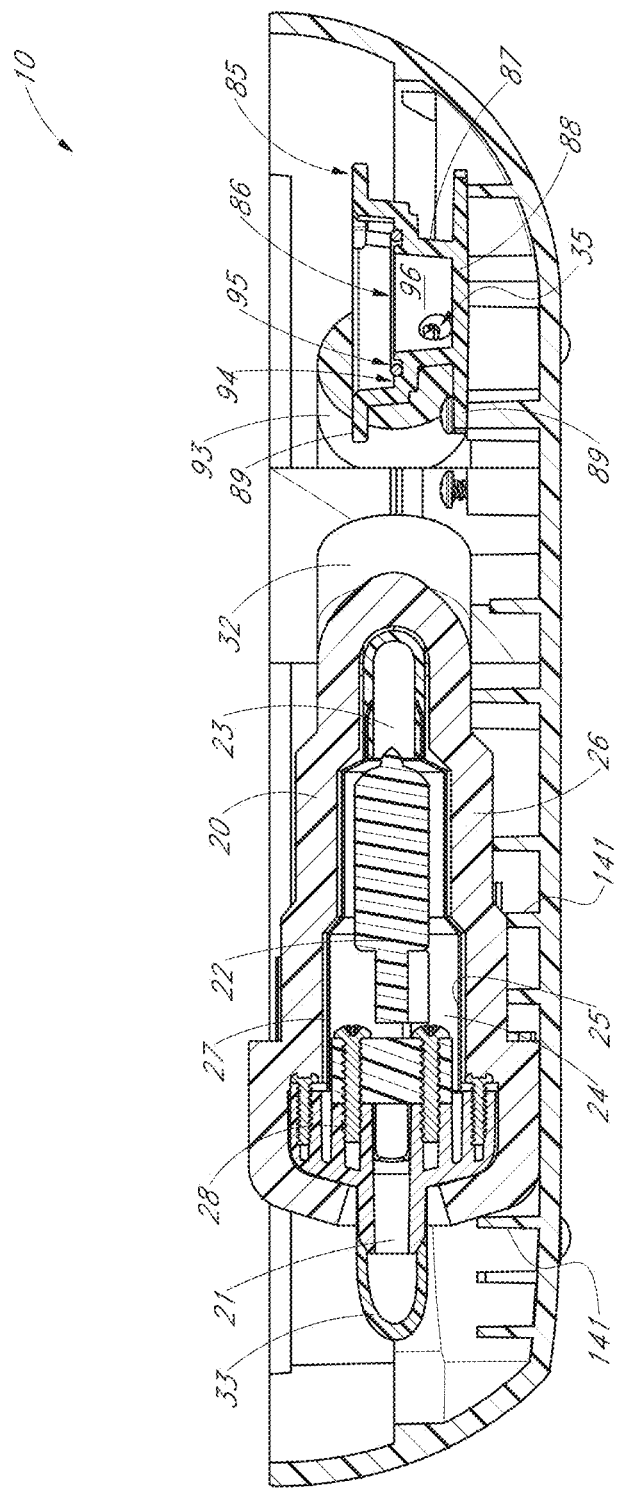
FIG. 5 is a side-cross sectional view of an example of a non-limiting embodiment of a lower portion of the vaporizer shown in FIGS. 3-4 taken along line 5-5 of FIG. 4.

In the illustrated embodiment, the bowl receptacle 85 comprises an opening 86 configured to receive and engage with a portion of bowl 50 (for example, lower portion 52). Opening 86 can comprise an opening formed by one or more sidewalls 87 extending longitudinally from the opening to a base 88. Bowl receptacle 85 can engage with bowl 50, for example, with threads or other engagement elements configured on the inner surface of sidewalls 87 and if desired a corresponding outer surface of sidewalls 55 of bowl 50. Referring to FIG. 5, in some embodiments, sidewalls 87 can comprise a ledge or shoulder 94, on which bowl 50 can rest when engaged with receptacle 85, forming a lower cavity 96 within receptacle 85. An o-ring or other sealing element 95 can be positioned between bowl 50 and receptacle 85, to provide sealing there between.

Referring to FIG. 6A, bowl 50 can include a protrusion, such as a thread or rib 132, that extends partially or completely around the lower portion 52 of the bowl 50. Rib 132 can be configured to engage with a corresponding slot or groove in a corresponding portion of bowl receptacle 85. In some embodiments, the rib 132 can include a gap 133 in its perimeter around bowl 52, wherein the gap 133 is configured to engage with a corresponding tab 91 (FIGS. 3 and 4) on bowl receptacle 85. Gap 133 and tab 91 can facilitate the alignment of bowl 50 with respect to bowl receptacle 85 during the attachment thereto or removal there from.

Base 88 (FIG. 5) can be configured to attach the bowl receptacle 85 to at least one of housing portions 62, 64 (or an intermediate structure) in a variety of ways. In some embodiments, bowl receptacle 85 can include optional flanges 89 extending from a portion of base 88 and/or sidewalls 87 to facilitate said attachment to housing portions 62, 64.

It will be understood that other types of accessory-receiving elements can be provided with embodiments of the vaporizers described herein. For example, the vaporizers can include an accessory-receiving element, such as a pocket, cavity, compartment, etc., to receive and store a personal item unrelated to the vaporizer, such as a credit card, keys, and the like. In some embodiments, the accessory-receiving element can be configured as a pocket, cavity, compartment, etc., that can seal and be held under a pressure or vacuum with a gas-flow device, such as those known or described herein. For example, a compartment may be to store one or more therapeutic materials that are not being supported by the therapeutic support elements, and such a therapeutic material storage compartment can be held under vacuum to maintain the freshness or shelf life of the material.

Referring to FIGS. 1B, 1C, 2 and 3, vaporizer 10 can include one or more optional ribs, fins, cells, arms, and/or other support members, extending through or along some, most, or substantially the entirety of their length or width of housing portions 62, 64, to provide additional support to housing portions 62, 64, or components supported by housing portions 62, 64. For example, upper housing portion 62 can include a rib 140 extending longitudinally along its inner surface (FIGS. 1B-2). Rib 140 can provide support, for example, to housing portion 62, and some optional components attached thereto, such as light assembly 61 and/or inhalation bag-receiving element 83. For example, lower housing portion 64 can include one or more fins 141 to support heater 20 (FIGS. 1C; 3). Alternatively or additionally, one or more of such support members, such as rib 140 or fins 141, can be configured to provide increased heat-transfer, insulative, or cooling properties. Fins 141 can provide an increased surface area and, thus increased heat transfer, from the heater 20 (FIGS. 1C; 3).

Embodiments of the vaporizers described herein can include one or more valves or other flow control device (for example, flow regulators, pressure regulators, etc.) to control the flow of gas. For example, inlet 53 and/or outlet 59 of bowl 50 can include a flow controller to control flow from the heater 20 into the bowl 50, for example, to limit demand on the heater 20 and/or provide a metered dose of vapor. Additionally or alternatively, the inlet and outlet of the heater(s), gas analysis system(s), inhalation tube(s) or bag(s), or other vaporizer components known or described herein can include one or more flow control devices. Such flow control devices can be formed separately or integrally with the vaporizer components with which they control flow.

As mentioned above, vaporizer 10 can selectively flow gas (for example, heated or non-heated) through the first therapeutic material support 40 (see, for example, FIGS. 1B and 2), to provide aromatherapy, and/or the second therapeutic support 57 (see, for example, FIGS. 2 and 6B) attached to a bowl 50, to provide vapor therapy. Referring to FIGS. 1C-5, an example of the fluid flow through the vaporizer 10 can be as follows:

Gas flow device 30 can comprise any of a variety of devices suitable to receive a gas, and increase its pressure and/or flow velocity, such as a heater, pump, fan, blower, and the like. Gas flow device 30 can receive gas from a cartridge, or other gas source, or from ambient gas internal to or external to the vaporizer 10. In the illustrated embodiment, gas flow device 10 receives gas through optional inlet ports 37 extending through a portion of housing 60 (FIGS. 1B and 2).

Referring again to one or more of FIGS. 1C-5, an optional shroud or manifold 31 can reduce the cross sectional flow area from gas flow device 30, to accelerate flow velocity and/or increase pressure towards heater 20. Gas flow device 30 can be directly attached to heater 20. Preferably, gas flow device 30 can be in fluid communication with heater 20 through indirect attachment, with one or more intermediary components, to decrease the detrimental effects on gas flow device 30 that can be caused by heat produced by heater 20. In some embodiments, an intermediate conduit 33 can provide fluid communication between flow device 30 (for example, shroud 31) and an inlet 21 of heater 20, to reduce the heat received by gas flow device 30 (for example, through backflow of gas and/or conductive/radiant heat from heater 20). In some embodiments, an additional, one or more optional valves 34 can be configured between gas flow device 30 and heater 20 (for example, within conduit 33, and/or mounted to a portion of heater 20 and/or gas flow device 30), to provide further temperature isolation between gas flow device 30 and heater 20. Valve 34 can be closed, for example, when gas flow device 30 is not flowing gas, to prevent backflow of heated gas from heater 20 into gas flow device 30. Any of a number of types of valves 34 can be implemented, although as one non-limiting example a butterfly valve can provide the benefit of selective temperature isolation without reducing the flow provided by gas flow device 30 when the butterfly valve is open.

Gas can flow through the inlet 21 (see, for example, FIG. 5) of heater 20, through, across, and/or proximate to a heating element 22 (see, for example, FIG. 5) of heater 20, and from an outlet 23. The gas flowing through heater 20 can be selectively heated, depending on the operation of heating element 22. For example, the gas flowing from gas flow device 30 through heater 20 can be heated during vapor therapy, during a preheating step or during aromatherapy. In some embodiments, the gas flowing from gas flow device 30 through heater 20 can be not heated during aromatherapy, as described further herein.

The outlet 23 of heater 20 can be in fluid communication with the bowl 50, either directly (for example, into the inlet 53 of bowl 50), or through one or more intermediate structures. In the illustrative embodiment, the bowl receptacle 85 is in fluid communication with the outlet 23 of heater 20 and the bowl 50. For example, an optional inlet 35 (FIGS. 3-5) can extend through a portion of the bowl receptacle 85, such as sidewall 87 or base 88, to receive gas from the heater 20. The bowl receptacle 85 can receive gas directly from outlet 23 of heater 20, or indirectly, through an intermediary conduit 32 positioned between heater 20 and receptacle 85.

In some embodiments, an optional bypass, Tee, valve, or other suitable gas flow diversion or control device, such as diverter 161 (FIG. 4) can be employed to divert some, most, or substantially the entirety of the flow from the heater 20 around bowl 50. Diverter 161 can be employed to allow flow of gas through and from heater 20 (for example, from outlet 23) while restricting or eliminating flow through bowl 50. Such embodiments can allow cooling flow through heater 20 while reducing vaporization of therapeutic material in bowl 50, and thus reducing costs.

Bowl receptacle 85 can be in fluid communication with bowl 50, when bowl 50 is engaged or attached thereto. In the illustrated embodiment, gas can be received into bowl receptacle 85 (for example, within lower cavity 96; FIG. 5), which can fluidly communicate with bowl 50 through inlet 53 (FIGS. 6A; 6B). As described above, gas can flow through bowl 50 from inlet 53 to outlet 59.

The aforementioned gas flow (with the exception of the operation of heating element 22 to provide heated or unheated gas) can be used regardless of whether device 10 is being used during vapor therapy or during aromatherapy. Some non-limiting operational differences according to some embodiments between vapor and aromatherapy will be described presently:

In some embodiments during vapor therapy, a first (for example, vaporizable) therapeutic material can be supported within bowl 50, and heated gas can flow through or proximate to the therapeutic material, causing the material to at least partially vaporize, and providing a vaporized gas of therapeutic material from outlet 59. The vaporized gas can flow from outlet 59 into the lungs of a user (for example, through the inhalation tube 82), or can flow into the inhalation bag 83, which can later be removed from outlet 59, from which a user can receive vapor therapy. During vapor therapy, the housing portions 62, 64 preferably can be in an open position, to provide access to outlet 59 and bowl 50. A variety of vaporizable therapeutic materials can be used during vapor therapy, such as any of a variety of herbal remedies (for example, leaves, roots, bark, buds, etc.), synthetic, natural, or other remedies, or combinations thereof. For example, a vaporizable therapeutic material might combine a natural material with a synthetic material to provide a desirable therapeutic result. Such remedies can be provided in a variety of forms, including oils, liquids, gels, solids, powders, in the like, or any combination thereof. Some non-limiting examples of therapeutic materials that can be used during vapor therapy can include, for example, materials derived from sage, clover, mint, rosemary, mallow, mugwort, chamomile, tobacco, willow bark, and combinations of the same.

At least one of housing portions 62, 64 can include one or more apertures or housing channels 43 extending there through (for example, FIGS. 1A and 2), and configured to fluidly engage and disengage with the bowl outlet 59. For example, the therapeutic support 40 can include one or more openings, fittings, sleeves, or similar structure, such as a connector 44, configured to engage and disengage with bowl outlet 59, and provide fluid communication between bowl 50 and housing channel 43. Connector 44 and housing channel 43 can be separately or unitarily formed. In some non-limiting embodiments, connector 44 (and thus channel 43) can be engaged (for example, in fluid communication) with bowl outlet 59, when housings 62, 64 are in a closed position (for example, FIGS. 1A and 2). In some non-limiting embodiments, connector 44 (and thus channel 43) can be disengaged (and thus not in fluid communication) with bowl outlet 59, when housings 62, 64 are in an opened position (for example, FIG. 1B). Thus, in some embodiments, when housings 62, 64 are in a closed position, fluid can flow from bowl 50, and through or proximate to a second (for example, aromatic) therapeutic material supported by the second material support 40, to provide aromatherapy. A variety of aromatic therapeutic materials can be used during aromatherapy, such as any of a variety of herbal materials (for example, leaves, roots, bark, buds, etc.), synthetic, natural, or other materials, or combinations thereof. For example, a vaporizable aromatic material might combine a natural material with a synthetic material to provide a desirable aromatic result. Such aromatic materials can be provided in a variety of forms, including oils, liquids, gels, solids, powders, in the like. Some aromatic materials that can be used during aromatherapy can include essential oils, incense, perfumes, or combinations thereof, such as, for example, materials derived from lavender, chamomile, firs (for example, fir needles), rosemary, cypress, cedarwood, geranium, sage, thyme, oregano, clove, cinnamon, citrus, and the like.

Second material support 40 can comprise any of a number of different structures, such as a tray, basin, receptacle, or other container suitable to hold an oil, liquid, gel, solid or semi-solid material, or combinations thereof. In some embodiments, material support 40 can include a portion configured to absorb or hold a material (for example, a liquid) in suspension, such as a sponge, cotton pad, and the like. Similar structure can be implemented with first material support 57 within bowl 50, described above. In some embodiments, material support 40 can comprise an optional movable portion, such as a movable plate or tray 42 (FIGS. 1B; 2) that can move between a load/unload position, to facilitate access to the tray 42 during loading and unloading of therapeutic material, and a process position, in which gas can pass proximate to or through therapeutic material supported on material support 40. A movable material support 40 can move or extend either to and from an external portion (for example, surface) of one or more housing portions 62, 64, to allow for external unloading/loading of a therapeutic material, or can move or extend to and from an internal portion (for example, surface) of housing portions 62, 64. Second material support 40 can be attached to an inner surface of at least one of housing portions 62, 64, such that support 40 is enclosed within inner cavity 66 when the first and second housing portions are in a closed position.

Some embodiments of the vaporizers described herein can be configured to facilitate simultaneous, or separate, vapor therapy and aromatherapy. Additionally, while the embodiments described herein disclose a common flow path from the gas flow device through the heater and bowl to provide both aromatherapy and vapor therapy, one or more components of the vaporizers described herein can be separate to form a partially or completely separate flow path and/or control and operation of the aromatherapy and vapor therapy.

Referring to FIG. 5, the heater 20 can comprise a number of different configurations suitable to heat a gas flowing there through, to facilitate vaporization of a therapeutic material in bowl 50. The heater 20 includes the inlet 21 to receive gas into an internal heater plenum or chamber 24. Gas can flow through the heater chamber 24, proximate to (for example, around) the heating element 22, and from the heater 20 through the outlet 23. The heater 20 can include any of a number of different configurations to its heating element(s), sidewall(s), inlet(s), outlet(s), or other components known or described herein, to provide radiant, convective and/or conductive heat transfer, to improve the efficiency of the energy transfer from the heating element(s) to a gas flowing through chamber 24.

The heating element 22 can include any of a number of different configurations suitable to provide energy to a gas flowing through chamber 24. For example, the heating element 22 can comprise a resistive wire, lamp or other thermal lighting element (for example halogen bulb, infrared lamp, glow plug), butane, fixed-aim laser, scanning laser, and the like. In some embodiments, the heating element 22 can include, for example, a halogen bulb ranging between 5 W and 250 W, such as a 50 W or 100 W halogen bulb. A laser heater can be used in low-power configurations, such as in portable application, because of its increased efficiency.

Figure 13A:
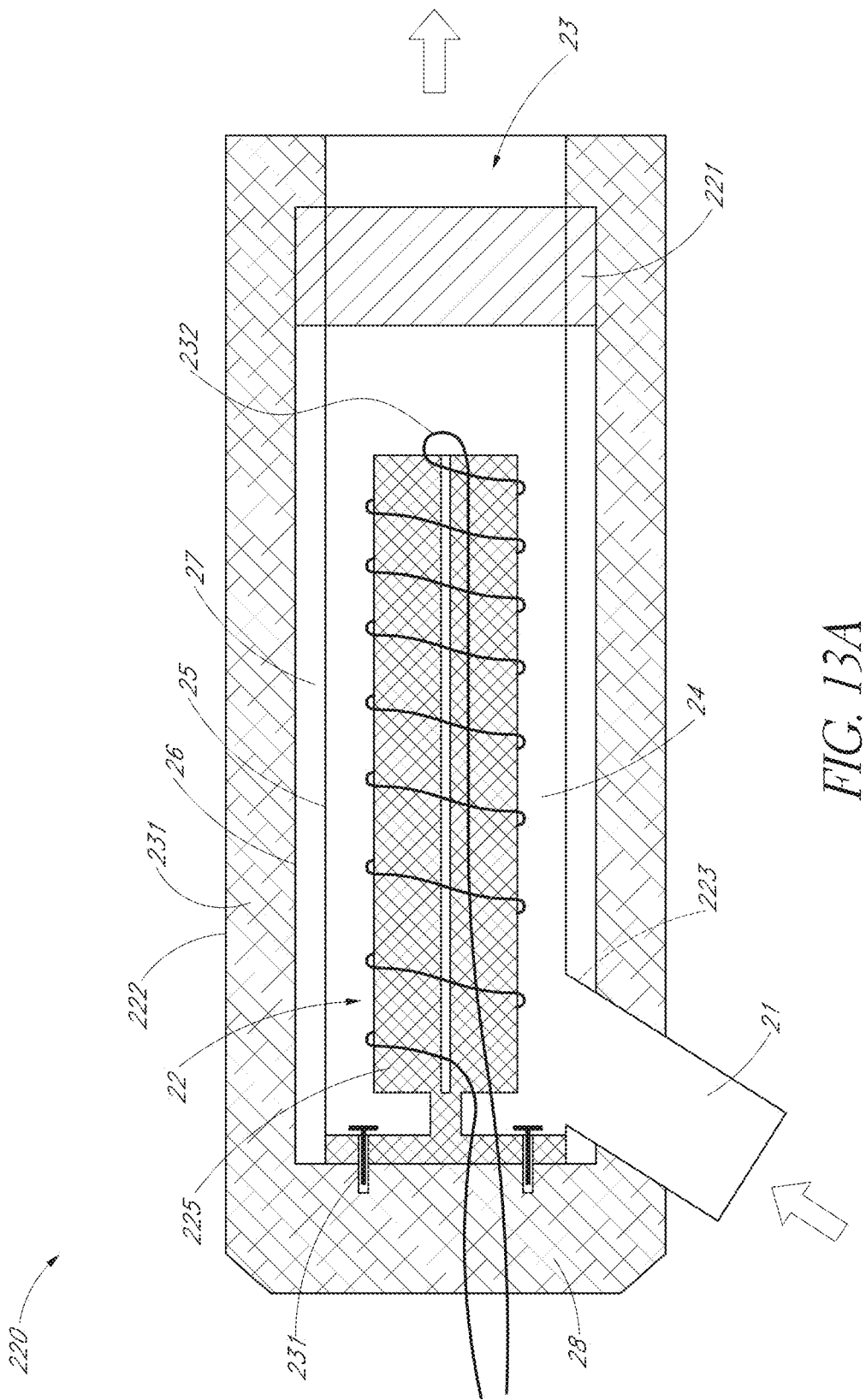
FIG. 13A is a side cross-sectional view of an example of a non-limiting embodiment of a heater.
Figure 13C:
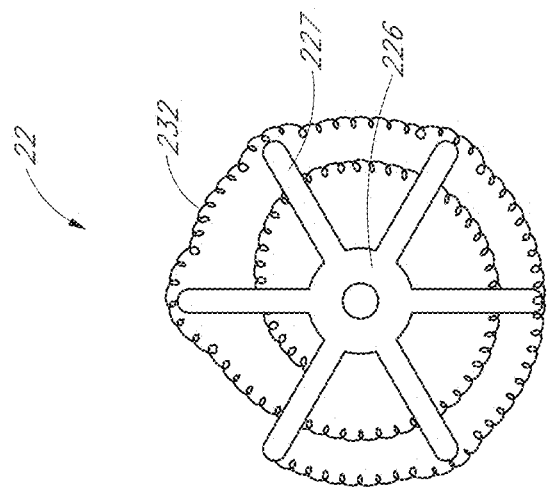
FIGS. 13B and 13C are side perspective and end views respectively, of an example of a non-limiting embodiment of a resistive wire heating element.
Figure 13B:
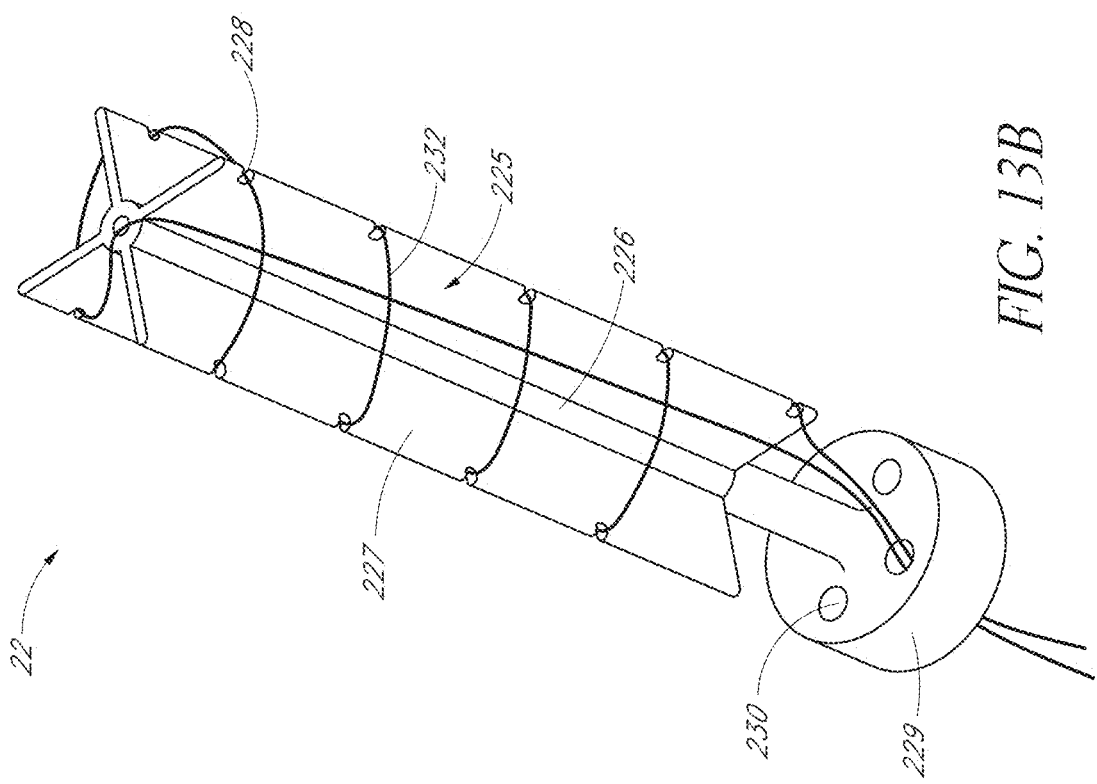

Referring briefly to FIGS. 13A-13C, in some embodiments, the heating element can include, for example, a resistive wire 232 comprising, for example, NiCr, or a similar, suitable resistive heating material. In some embodiments, the heating element 22 may include a coiled resistive wire. In some embodiments, resistive wire heating elements can be configured to provide power within a range, for example, of approximately zero up to approximately 2,000 watts, or more narrowly, approximately 50 watts to approximately 1500 watts, or more narrowly, approximately 100 watts to approximately 500 watts. In some embodiments the resistive wire heating elements can provide increased speed or amount of heat transfer, through decreased wire diameter, increased number of coils, and/or increased wire length than known resistive wire heating elements. For example, some known resistive wire heating elements simply use a small diameter, short, wire, with low power capabilities. Other known resistive wire heating elements use thicker diameter wires, with higher power capabilities, but have corresponding long response times.

In some embodiments, the resistive wire 232 can be, wound around an electrically insulating and thermally conducting core 225, such as ceramic or porcelain. The thermally conductive core 225 can include one or more supporting structure(s), such as fins 227 extending laterally (for example, radially) from a strut or other support member 226. The resistive wire 232 can be attached to core 225 and/or fins 227 in any of a number of different ways, such as with one or more of the attachment elements described herein or known. In some non-limiting embodiments, one or more notches 228 can extend into a portion of fins 227, allowing wire 232 to be wrapped or coiled around core 225, and supported with the notches 228. The heating element 22 can be supported within chamber 24 in any of a number of different ways; in the illustrated embodiments, heating element 22 includes a base 229 attached to a sidewall, end cap 28 (FIG. 13A; FIG. 5), or other structure of heater 20, allowing the heating element 22 (for example, support member 226 and/or fins 227) to extend within chamber 24. Base 229 can be attached to cap 28 with any of the attachment elements described herein; in the illustrated embodiment base 229 includes apertures 230 configured to receive fasteners 231 therethrough. Apertures 230 can also allow passage of the resistive wire through base 229, and/or through additional apertures extending through another portion of the heater 22, such as cap 28.

Fins 227 can be configured with a shape that can direct gas flow within chamber 24, for example, to increase turbulence in the gas and increase convective heat transfer. Fins 227 can be substantially straight, or can be a substantial curvilinear shape (for example, to create additional turbulence, such as a vortex). Fins 227 can include one or more attachment elements, such as notches 229, to facilitate the attachment of wire 232 to core 225.

In some embodiments, the heating element 22 can be coated or enclosed by a conductive shroud, such as aluminum, to enhance the heat transfer from heating element 22 into chamber 24.

In some aspects, a potential challenge in designing a heater 20 within a vaporizer housing, is the heater should be able to sufficiently heat the gas flowing there through, to a temperature sufficient for vaporization (for example, downstream, in bowl 50), without transferring an amount of heat from the external portions of heater 20 that can damage adjacent components (for example, gas flow device 30, controller 100, etc.).

In some embodiments, the heater 20 can comprise one or more sidewalls configured to form the heater chamber 24. In some embodiments, the heater 20 can comprise two or more nested or layered sidewalls, or sidewall portions, to form a double-walled design (or triple-walled, quadruple-walled, etc.; see also FIG. 12). In embodiments with two or more sidewalls, said sidewalls can comprise similar or different materials, with similar or different material properties. For example, the material of one or more sidewalls may be selected for thermally insulative, conductive, or heat transfer characteristics, whereas the material of the same sidewall, and/or one or more additional sidewalls may be selected for strength or rigidity. The sidewalls can comprise, for example, metal, plastic, glass, ceramic, liquid, gas, gel or other suitable materials known or described herein. In some embodiments, the sidewalls (for example, an inner or outer surface) can be coated with a material. For example, a coating of material may be selected for its thermal properties, and/or for being inert to particular vaporizable materials used in device 10. In a preferred embodiment, a heat-absorbing material is used on the inner surface of chamber 24 is implemented to improve uniformity of heat transfer there within. Even more preferably, the heat absorbing material comprises anodized aluminum, such as black-anodized aluminum.

Figure 12:
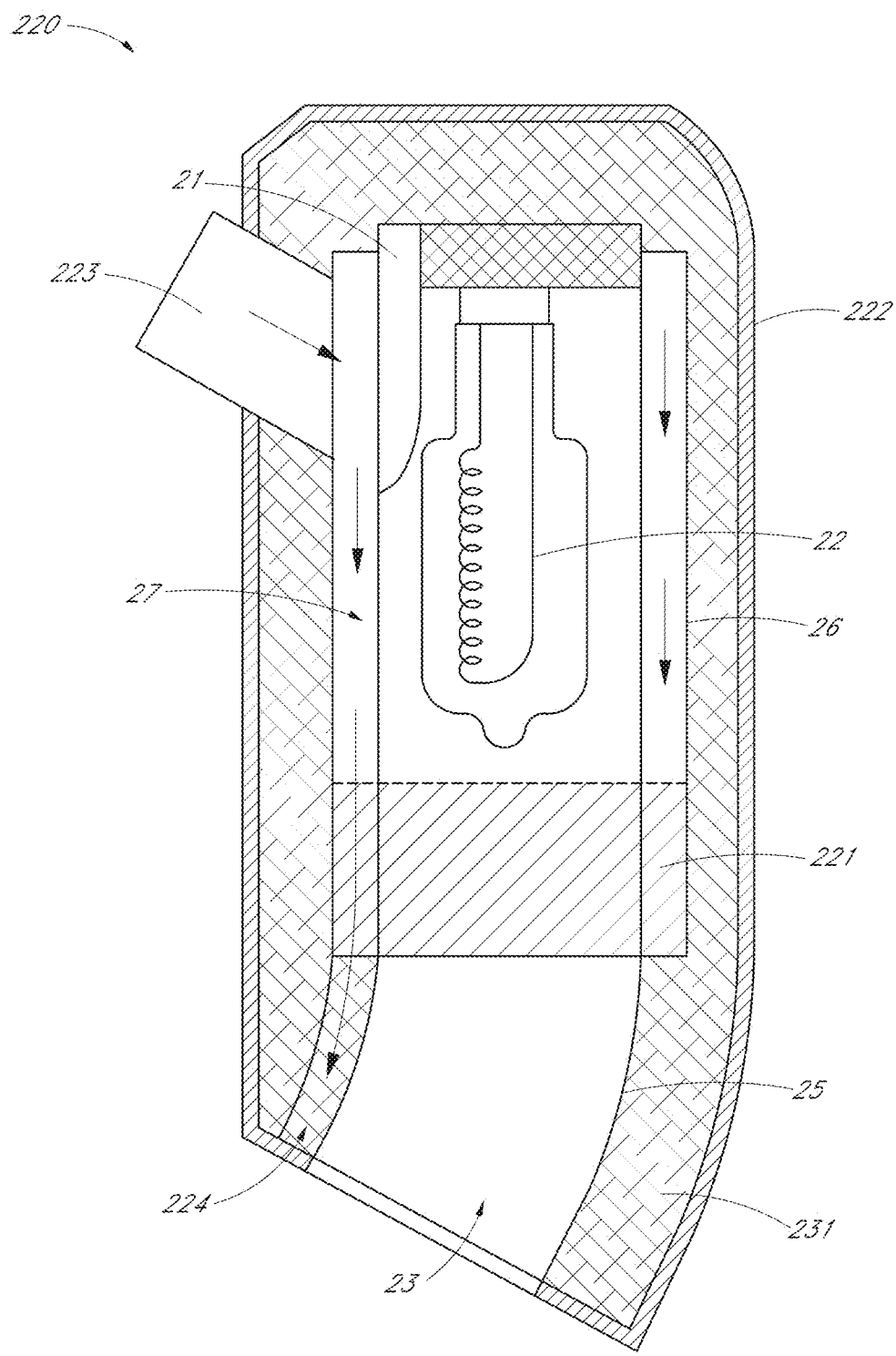
FIG. 12 is a side cross-sectional view of an example of a non-limiting embodiment of a heater.

The one or more sidewalls are not limited to a circular cross-section or tubular design, and can be any shape suitable to form an inner chamber or volume, such as those described herein for bowl 50. Additionally, embodiments with two or more sidewalls may be contacting each other, to provide heat transfer (for example, conductive) there between, or may be configured with a gap extending at least partially between portions of two adjacent sidewalls, to provide insulative properties. In the illustrated embodiment, the heater 20 comprises a first (for example inner) sidewall 25, and a second (for example, outer) sidewall 26, with an insulating gap 27 extending between at least some portions of sidewalls 25, 26. Gap 27 can be filled with air, or various gases, under pressure, or under vacuum, to vary the thermal insulative and/or heat transfer properties between walls 25, 26. Gap 27 can form an enclosed volume between walls 25, 26 (for example, FIG. 5). In some embodiments, gas, liquid, powder, or another flowable medium can be flowed between the sidewalls, to provide heat transfer (for example, cooling flow) there between, as described further below (FIGS. 12-13C). Walls 25, 26 can comprise any of the materials described generally for the heater sidewalls; in the illustrated embodiment, inner wall 25 comprises a thermally conductive metal, such as aluminum, and outer wall 26 comprises a thermally insulative material, such as glass. An additional shroud, shell, or wall, support members, or other structures, can surround outer wall 26, to provide additional support and prevent damage thereto (for example, in embodiments wherein outer wall 26 comprises a fragile material such as glass).

The one or more sidewalls of heater 20 can include one or more structures extending from, into, through, or along a portion thereof, to provide increased heat transfer from various portions of heater 20. For example, as described above, additional cooling elements or fins 141 can be in contact with a portion (for example, outer surface) of one or more sidewalls of heater 20, to provide heat transfer there from. In some embodiments, gas can be flowed over the cooling fins 141, to expedite the heat transfer over cooling fins 141. Such positive cooling flow can be provided, for example, by diverting a portion of the gas flow from gas flow device 30, and/or through the use of an optional, second, auxiliary gas flow device 35 (for example, FIG. 3).

FIG. 12 is a side cross-sectional view of an embodiment of a heater 220, which can be substantially similar to heater 20. Either heater 20 or 220 can be employed with any of the embodiments of the vaporizers described herein, or known in the art. Heater 220 can comprise an optional inlet 223 configured to provide cooling flow into, around, and/or through the gap 27 between sidewalls 25, 26, and exit the heater assembly 220 from an outlet opening 224. Such cooling flow can be provided, for example, by diverting a portion of the gas flow from gas flow device 30, and/or through the use of an optional, second, auxiliary gas flow device 36 (for example, FIG. 3). Outlet opening 224 is optional; in some embodiments, cooling flow can both enter and exit gap 27 from inlet 223 (FIG. 13A). Additionally, inlet 223 to the gap 27 and inlet 21 to the heater cavity 24 can be configured with a common flow path into the heater 20 (for example, FIG. 13A), or a separate flow path into the heater (for example, FIG. 12).

Optional additional layers or sidewalls can provide additional functionality to heater 20. For example, as a flexible silica, fiber wrap, or other suitable insulation, or a resilient material can surround and/or enclose a portion, or substantially the entirety of one or more of the sidewalls of heater 220 (for example, sidewalls 25, 26). In the illustrated embodiment, a resilient sidewall or layer 221 can provide insulative properties and/or can comprise a resilient material that can absorb expansion of sidewall 25 and/or 26, and thus prevent damage thereto. In the illustrated embodiment, an optional additional insulative sidewall or layer 231 surrounds one or more of sidewalls 25, 26. An additional, optional shroud, clamshell, or sidewall 222, can surround or enclose sidewalls 25, 26 and the layer 231. In the illustrative embodiment, sidewall 222 comprises a high temperature plastic, but can comprise any of the materials described generally herein for heater sidewalls.

As described above, vaporizer 10 can include the optional controller 100 and/or the user interface 110, to provide additional functionality and/or control over various aspects of vaporizer 10. Controller 100 can include a memory portion, for example, to save user profiles (recipes) for various vaporization and/or aromatherapy sequences, temperatures, therapeutic materials, and other vaporization preferences. Controller 100 and/or user interface 110, and any other components of vaporizer 10 that consumer power, can receive such power from an external or internal power supply, such as a battery 38 (FIG. 3). Battery 38 can be disposable or rechargeable, such as lithium-ion or other known batteries in the art. Battery 38 and/or controller 100 can be in communication with an external power source, computer system, handheld device, etc., through a port 39 (FIGS. 2-3). In some embodiments, vaporizer 10 can include an internal or external power supply capable of providing power sufficient to supply power to a NiCr wire or other heating element up to 1500 Watts, to provide increased heating response, as described elsewhere herein. Port 39 can provide a power connection, a communication connection, or both (such as FireWire or USB). The control systems and other electronic components of the vaporizers described herein can also be configured to communicate wirelessly.

In some embodiments, vaporizer 10 can include one or more sensors to detect various parameters that measure, for example, the position, flow rate, temperature, density, pressure, etc., of vaporized or non-vaporized gas within the device, or other components of the device itself (for example, the temperature of the heater, therapeutic material support, etc.). These sensors can be configured to provide feedback to the user (for example, through the user interface 110, for example, for open loop control) and/or can provide feedback to the optional controller 100 (for example, to provide closed-loop control) for these various parameters of the vaporizer processes.

For example, vaporizer 10 can include an optional position sensor 73 (FIG. 1B) configured to detect whether the first and the second housing portions are in the open or closed position. Position sensor 73 can comprise a proximity switch (for example, optical), encoder, inductive (for example, non-contact), Hall effect sensor, and other such devices. Position sensor 73 can be positioned anywhere within cavity 66 or attached to various portions of housing 60. In the illustrated embodiment, position sensor 73 is positioned on a portion of housing portions 62, 64 proximate to latch 72. The control system 100 can be associated with the position sensor 73 and can be configured to control the operation of one or more of the gas flow device 30 and the heater 20 in response to an output provided by the sensor 73. For example, the control system 100 can be configured to stop operation of at least one of the gas flow device 30 and the heater 20 in response to an output from the sensor 73 indicating that the first and second housings 62, 64 are in the closed position. In some embodiments, the control system 100 can include an optional timer configured to stop operation of the at least one of the gas flow device 30 and the heater 20 after a preselected time period.

In some embodiments, vaporizer 10 can include one or more temperature sensors to detect one or more temperatures on, within, or proximate to a portion of vaporizer 10. For example, vaporizer can include a first temperature sensor 74 configured to detect a first temperature proximate to or within a portion of the heater 20 and/or a second temperature sensor 75 configured to detect a second temperature proximate to or within a fluid pathway formed downstream of the heater (FIGS. 3 and 4). Temperature sensors 74, 75 can comprise a contact (for example, thermocouple, RTD, and the like) or non-contact (for example, pyrometer) type of sensor, or other temperature sensing devices known in the art.

The controller 100 can comprise a temperature controller portion associated with the first and the second temperature sensors 74, 75, and the heating element 22 within heater 20 for controlling the temperature of a gas flowed through the bowl 50 (for example, through, across, or proximate to material support 57). For example, the controller 100 can be configured to control the operation of the heating element 22 (for example, activate and deactivate) in response to an output signal received from at least one of the first and second temperature sensors 74, 75. In some embodiments, the temperature controller 100 can be configured to control the operation of the heating element 22 in response to an output signal received from both the first and the second temperature sensors. In some embodiments, the temperature controller 100 can be configured to control the operation of the heating element 22 in response to an output received from only one of temperature sensors 74, 75, and in some embodiments, only from temperature sensor 75.

Embodiments of the temperature sensors and control system described herein can allow for increased precision in the control of the temperature at the target temperature of the therapeutic gas (for example, proximate to the point of use; for example, proximate to or within the bowl and/or therapeutic material support). The embodiments can allow flow control of the heat reserve upstream of the point of use to bring the point of use to a desired temperature rapidly. The embodiments can provide dual temperature zones (for example, proximate to each of the temperature sensors) to facilitate additional temperature control. The heater can be preheated to a safe level (for example prior to therapy) and maintained for a predetermined time when the vaporizer is not vaporizing the vaporizable material (for example, the vaporizer is idle). In embodiments which measure and control a single temperature set point at the bowl, the heater can deactivate, while gas flow continues through the heater and bowl, and continue to vaporize a therapeutic material, until the temperature proximate to the therapeutic material drops below a threshold (for example, below the vaporization temperature of the material). In some embodiments, a standby mode can be employed, in which temperature is decreased to reduce consumption (for example vaporization) of the material while not being used (for example, inhaled). Algorithms can be produced that can estimate demand and adjust the heater power accordingly. For example, if there is a large draw on the heater, the temperature of the bowl may increase rapidly while reducing the temperature in the heater. In such a scenario, the power of the heater can be activated or increased for a time period to minimize the potential temperature decrease, and catch up with temperature demand if the draw continues. The inverse can also be true; if the bowl temperature is rising, but the heater temperature is substantially constant (or increasing), the power to the heater can be deactivated or reduced if necessary, to decrease bowl temperature.

Sensors 74, 75 can be attached to a variety of portions of vaporizer 10. Sensor 74 can be attached on or proximate to a surface (for example, internal or external) of heater 20. Sensor 75 can be attached on or proximate to a fluid pathway extending through the bowl 50, or through bowl receptacle 85.

Figure 9:
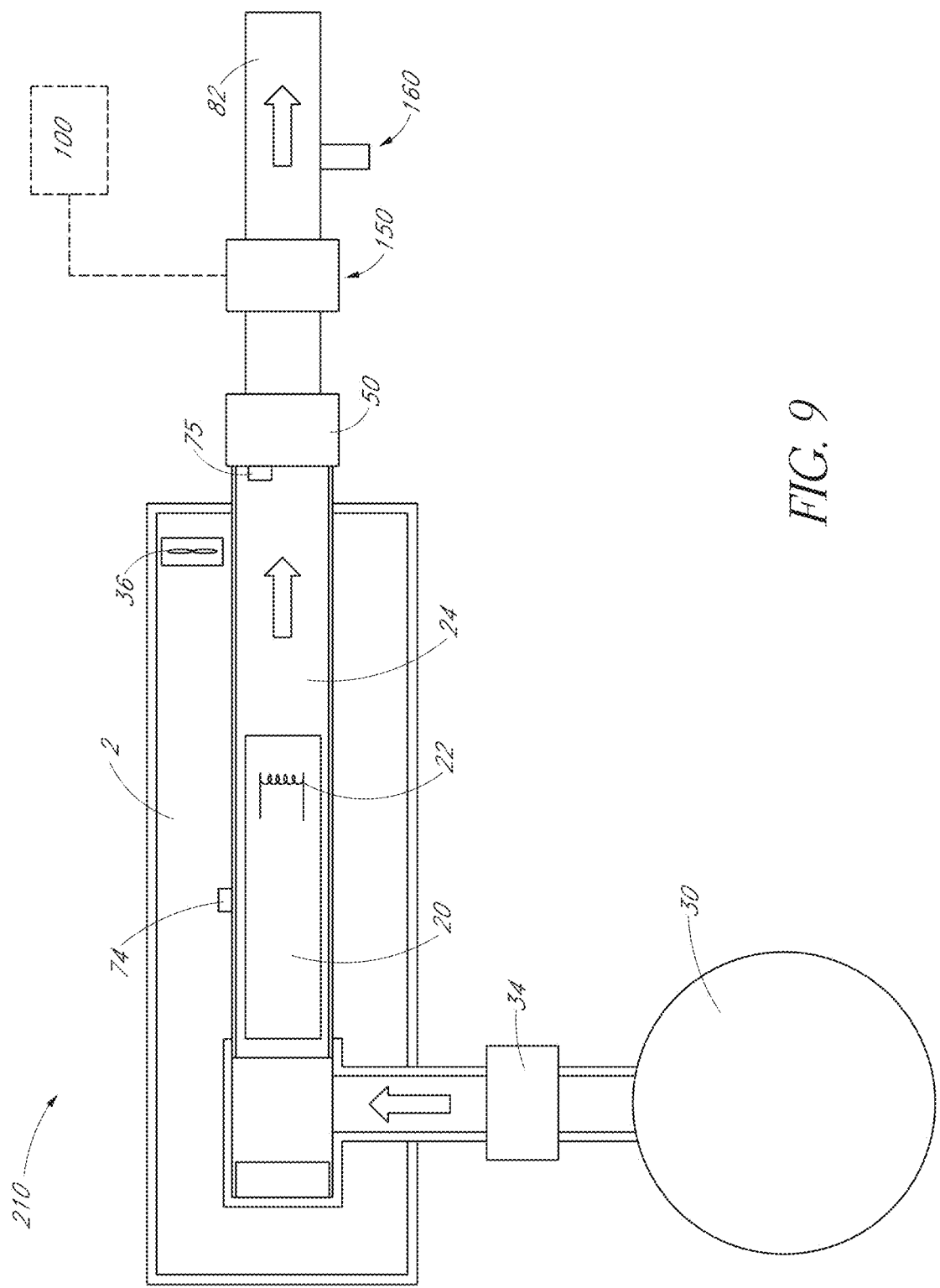
FIG. 9 is a plan schematic view of an example of a non-limiting embodiment of a vaporizer.

FIG. 9 is a plan schematic view of an embodiment of a vaporizer 210. In some non-limiting embodiments, the vaporizer 210 can be substantially similar to vaporizer 10, with the following optional differences. Vaporizer 210 can include a gas analysis system 150 configured to quantitatively and/or qualitatively analyze the gas within, or downstream of bowl 50. Gas analysis system 150 can be integrated into bowl 50 or another portion of vaporizer housing 60 (for example, within cavity 66; for example, FIG. 1B, or other vaporizers described herein), or can be formed and/or positioned downstream of bowl 50 (for example, a separate component from vaporizer 210; for example FIG. 10, or other vaporizers described herein).

Gas analysis system 150 can include one or more sensors such as those known or described herein, to provide open loop (passive) or closed loop (active) control of various parameters of the gas (for example, vaporized gas) flowing within or downstream of bowl 50. The sensors can detect, for example, temperature, pressure, flow rate, etc. In some embodiments, the sensors can detect gas constituents such as CO, NO, NO2, CO, CO2, O2, etc., to provide feedback, for example, on the vaporization process, and the quality of the vaporized material within or downstream of bowl 50. For example, it may be desirable to monitor the amount of CO or other constituents to detect combustion of the vaporizable material, and adjust the heater 20 to improve quality of the vaporized gas. For example, if CO is sensed (indicating combustion is occurring, instead of higher quality vaporization), the heater 20 may be deactivated, or its thermal output otherwise decreased. In some embodiments, CO and vapor density are measured in a closed loop automatic control system, to dynamically optimize (for example, in real time; continuously or intermittently) for higher density vapor production with reduced combustion constituents. In some embodiments, gas analysis system can analyze one or more of these attributes of the vaporized gas to decrease combustion of the vaporizable material while increasing the positive/desirable therapeutic material in the vapor. The sensors can communicate with a control system (either external or internal to housing 60; for example, control system 100), to perform cytometric or other gas analyses, using, for example, spectroscopy, thin layer chromatography, mass spectrometry, vapor density measurement, and the like.

In some embodiments, an optional gas inlet 160 can be implemented, to allow additional gas to enter into the vaporized gas flow path prior to vaporized gas being inhaled by a user. Such additional gas can increase the flow of gas to the user (for example, if the user inhales deeply), while maintaining, or without substantially increasing the gas flow through the heater, which can reduce the accuracy and consistency of the temperature control of the gas through the bowl 50. In this way, optional gas inlet 160 can improve vaporization temperature stability and therefore quality of the vaporized gas exiting bowl 50. Gas inlet 160 is shown attached to the inhalation tube 82 for illustrative purposes, but can be attached to or in fluid communication with any of a number of components positioned downstream of bowl 50 (for example, within the vaporization plenum), such as at or downstream of the outlet of the bowl 50, at or downstream of the outlet of the system 150. Gas inlet 160 can comprise any of a number of different structures that allow free flow, or control the amount of flow into the vaporized gas flow path. For example, gas inlet 160 can comprise a fixed orifice, a flow controller, or a pressure release valve that opens when the pressure or amount of flow within the vaporized gas flow path exceeds a predetermined amount.

Figure 10:
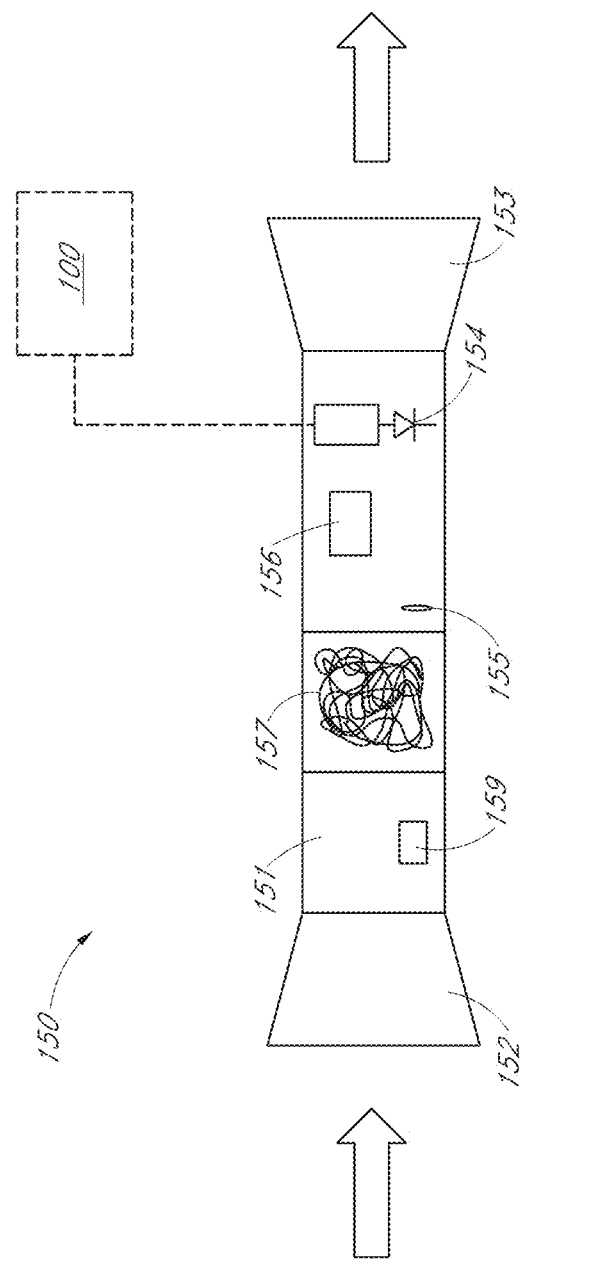
FIG. 10 is a plan schematic view of an example of a non-limiting embodiment of a gas analysis system.

FIG. 10 is a plan schematic view of an embodiment of the gas analysis system 150 shown in FIG. 9 that can be implemented with a vaporizer, such as vaporizer 10 or 210, or others known or described herein, or used independently from a vaporizer, as a portable hand held wand that a user can exhale through. System 150 can include a tube, conduit or other structure 151 suitable to flow gas from an inlet 152 to an outlet 153. Inlet 152 can be in communication with (for example, connected to bowl outlet 59) or integrated into bowl 50, or inhalation tube 82 (for example, FIGS. 1C; 8). Outlet 153 can be in communication directly with a user, or can be connected to a mouthpiece, inhalation tube, or inhalation bag. A transmitter comprising a light source 154, such as a collimated light source (laser), LED, etc., can direct light towards a light guide/diffuser 155, diffracting light across or through a portion of the tube 151, which is viewable through a window 157. The laser may also be scanned by controlling the laser output angle, and/or controlling its reflected light off of a surface (for example vibrating reflective membrane, Micro-Electrical-Mechanical-System (MEMS) reflective array). The illuminated vaporized gas can be viewed by a user, to determine vaporization quality, and to adjust the vaporization process. Optical surface treatments or coatings can also be used in the viewing region to enhance the appearance and effects of the illumination process.

In some embodiments, system 150 can be controlled to provide spatial or selective illumination, such as with a scanned pattern or a raster scan. Such embodiments can provide patterns created by light source 154, to facilitate the analysis of the light pattern, and/or to provide an aesthetic appeal (for example, a laser light show, etc.). Gas analysis system 150 can include a power source, such as those known or described herein, illustrated as a battery 156, and/or a power switch, illustrated as switch 159.

Figure 11:
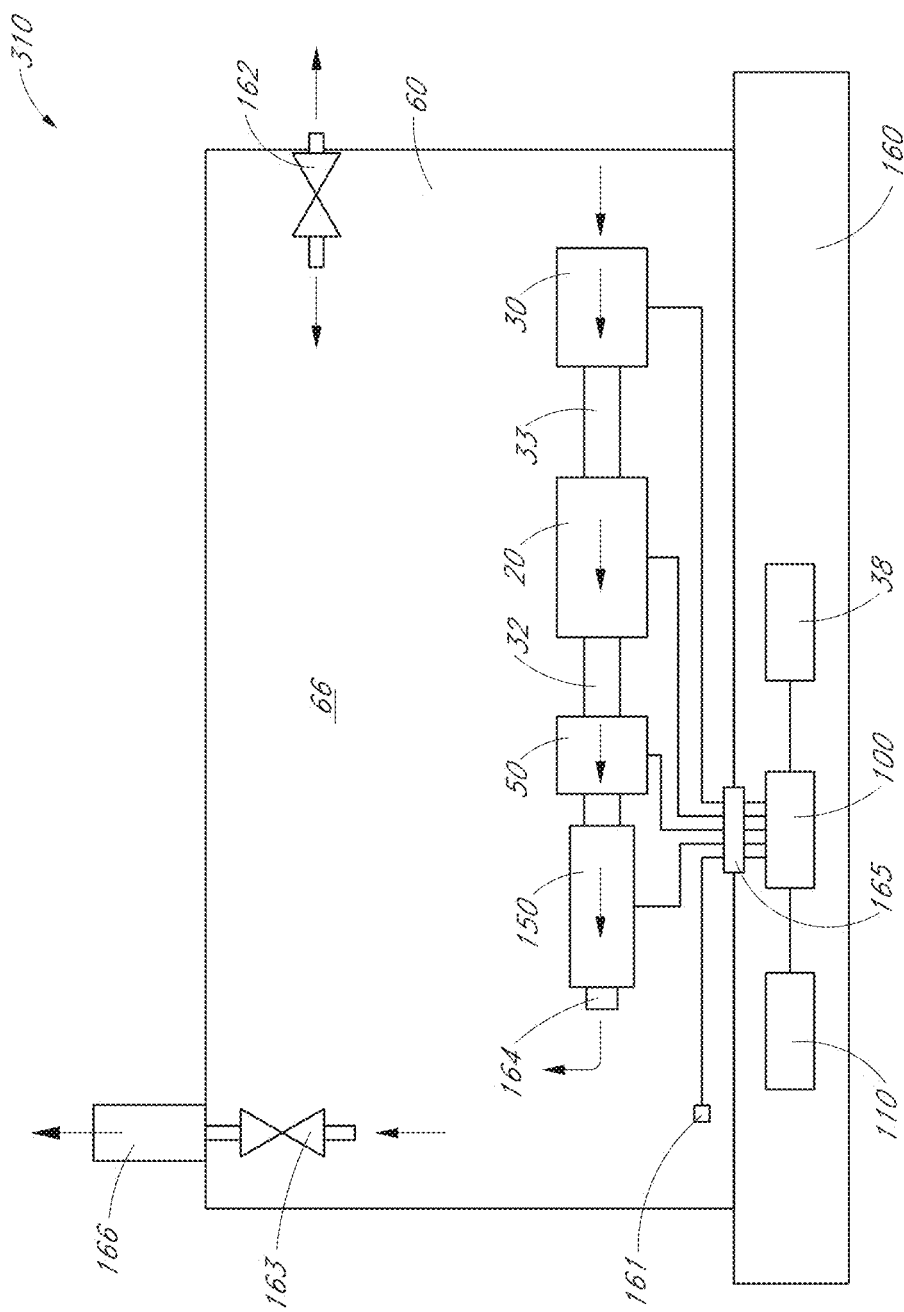
FIG. 11 is a side schematic view of an example of a non-limiting embodiment of a vaporizer.

FIG. 11 is a side schematic view of an embodiment of a vaporizer 310. Vaporizer 310 can be substantially similar to vaporizer 10, with the following non-limiting optional differences. In some embodiments, vaporizer 310 can include an internal outlet 164 that allows gas to exit from the gas flow system (for example, gas flow device 30, heater 20, bowl 50, and, in some embodiments, optional analysis system 150) and into the inner cavity 66 of housing 60. Housing 60 can be substantially air and/or vacuum tight, allowing the gas flow device 30 to maintain a vacuum or pressure within housing 60 ranging from −14.7 psig to 90 psig, for example. Maintaining a vacuum within housing 60 can maintain the freshness, or shelf life, of a therapeutic material stored within vaporizer 310. A release valve 163 can be provided to control gas flow such that a user can receive (through manual or electronic actuation of valve 163) vaporized gas from an outlet 166 of vaporizer 310. In some embodiments, inner cavity 66 can be filled with pressurized, vaporized therapeutic gas, to provide increased volume and flow of therapeutic gas upon release of valve 163, for example, to assist with delivery to a patient with weak lungs.

One or more optional valves 162 can be provided for additional control of gas flow to and from cavity 66. For example, valve 162 can be configured as a release valve (to release vacuum or pressure stored within cavity 66, and/or when the pressure or vacuum exceeds a certain amount). For example, valve 162 can provide a selectable inlet to cavity 66; for example, valve 162 can allow flow to provide an external gas supply to device 30 when device 30 is providing positive pressure gas, and valve 162 can restrict flow to seal cavity 66 and allow device 30 to pump a vacuum within cavity 66. A sensor 164 can be configured to sense vacuum and/or pressure within cavity 66, and in some embodiments, communicate with controller 100 to control various components of vaporizer 310, similar to the other embodiments of sensors and controller 100 described herein.

In some embodiments, housing 60 can be a separate piece mounted onto a vaporizer base 160. In such embodiments, one or more components of vaporizer 310 can be attached to or stored within base 160. For example, one or more of the power source (for example, battery) 38, controller 100, and user interface 110 can be attached to or stored within base 160. In some embodiments, one or more mechanical attachment and/or electrical attachment (for example, electrical quick-connect 165) can be included, to facilitate attachment and detachment of housing 60 to and from base 160.

One or more therapeutic gases can be provided using embodiments of the therapeutic vaporizers described herein and shown in the figures, using various methods. In an embodiment, a therapeutic gas can be formed using the following steps: providing a therapeutic vaporizer that includes a housing 60 and a gas flow device 30, a heater 20, a first therapeutic material support 40 and a second therapeutic material support 57, wherein at least one of the first and second material support 40, 57 are positioned at least partially within the housing 60; forming an aromatic therapeutic gas by flowing a gas with the gas flow device 20 through or proximate to a first therapeutic material that is supported by the first therapeutic material support 40; forming a vaporized therapeutic gas by: flowing a gas through the heater 20 to form a heated gas and flowing the heated gas through or proximate to a second therapeutic material that is supported by the second therapeutic material support 57; wherein flowing the gas through the heater 20 to form a heated gas comprises flowing the gas with the gas flow device 30.

In some embodiments, the housing 60 comprises a first housing portion 62, 64 and a second housing portion 62, 64 configured to movably engage and disengage with respect to each other between a closed and open position; wherein the method further comprises detecting whether the first and the second housing portions 62, 64 are in the open or closed position.

In some embodiments, the method further may include controlling the operation of one or more of the gas flow device 30 and the heater 20 in response to the detecting.

In some embodiments, the method further can include sensing a first temperature proximate to or within the second therapeutic material support 57; and controlling the operation of the heater 20 in response to the sensing.

In some embodiments, the method further may include deactivating the gas flow device 30 during said sensing a first temperature and during said controlling the operation of the heater 20.

In some embodiments, the method further can include sensing a second temperature proximate to or within a portion of the heater 20; and controlling the operation of the heater 20 in response to the sensing the first temperature and sensing the second temperature.

In some embodiments, the method can include, for example, sensing the first temperature and sensing the second temperature occur at substantially the same time.

In some embodiments, the method further can include, for example, activating the gas flow device 30 during the sensing the first temperature, sensing the second temperature, and during said controlling the operation of the heater 20.

In some embodiments, the method further can include, for example, pre-heating the heater 20 prior to forming a vaporized therapeutic gas.

In some embodiments, the controlling the operation of the heater 20 can include, for example, activating and deactivating the heater 20 with a pulse-width modulated signal from a temperature controller 100.

In some embodiments, the forming an aromatic therapeutic gas and forming a vaporized therapeutic gas may occur at approximately the same time.

In some embodiments, the forming an aromatic therapeutic gas and forming a vaporized therapeutic gas can occur at substantially different times.

The following describes additional various embodiments of a vaporizer, or inhalation bags, connectors, bowls, or other features that may be employed for use with a vaporizer.

Figure 14E:
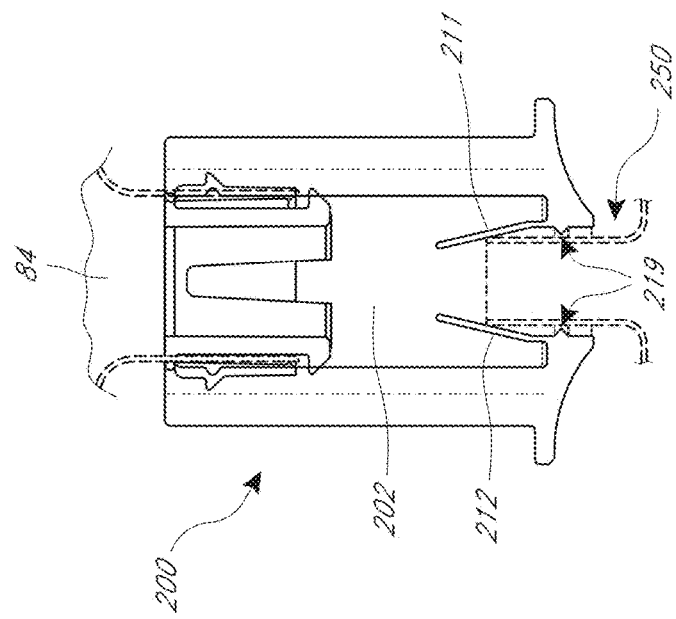
FIG. 14E is a side cross-sectional view of an embodiment of an attachment system with a valve for an inhalation bag, showing the valve in an opened position.
Figure 14D:
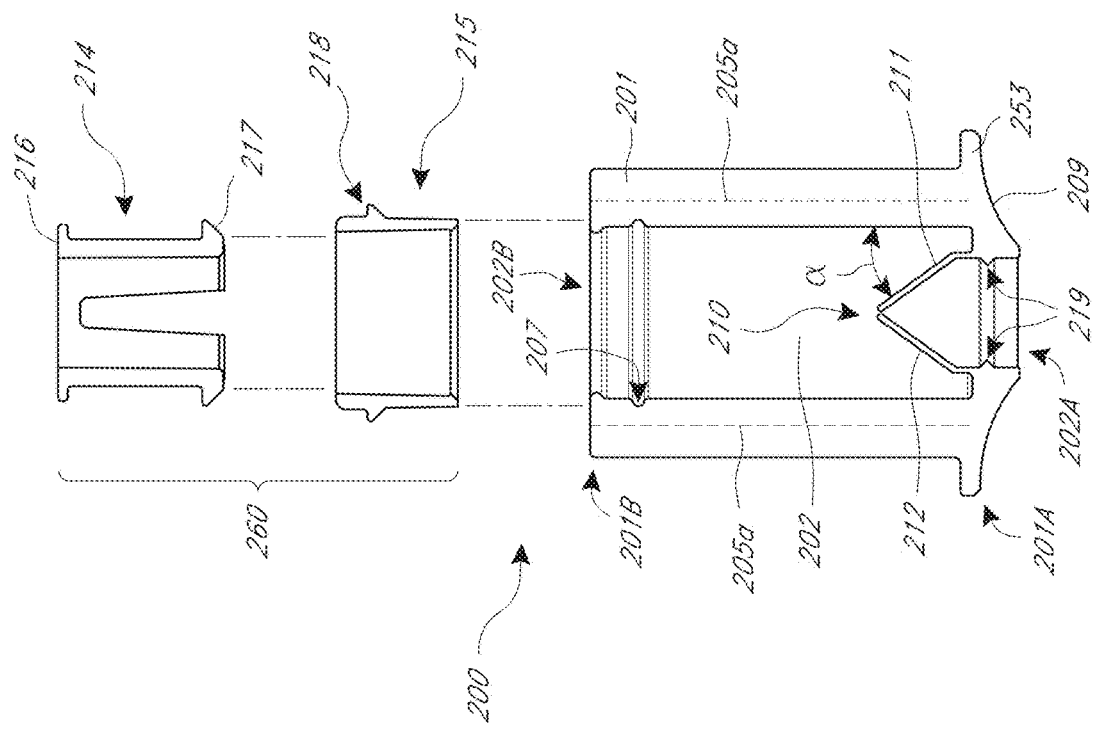
FIG. 14D is a side cross-sectional exploded view of an embodiment of an attachment system with a valve for an inhalation bag, showing the valve in a closed position.

FIG. 14A is a cross-sectional perspective view of an embodiment of an attachment system 200 with a valve 210 for an inhalation bag. FIGS. 14B-14C are bottom cross-sectional views of an embodiment of the attachment system 200, showing the valve 210 in a closed and open position, respectively. FIGS. 14D-14E are side cross-sectional views of an embodiment of the attachment system 200 with valve 210.

Attachment system 200 can be used with bag 84 (FIGS. 7A-7C), or with other inhalation bags. Attachment system 200 can include a body 201 with a lumen 202 allowing flow therethrough. The lumen 202 can extend from a first opening 202A of the body 201, to a second opening 202B of the body 201. The body 201, lumen 202, and openings 202A, 202B can be any suitable configuration to allow flow through system 200. Openings 202A, 202B can be positioned at opposed ends 201A, 201B, respectively, of body 201. For example, lumen 202 can comprise a substantially straight channel, or a curvilinear channel, or can comprise combinations of straight and curved channel portions. Openings 202A and 202B can be aligned along a common axis, or offset, or aligned with different axes at an angle with respect to each other. Openings 202A and 202B can be positioned at opposed ends of the body 201, as shown. Attachment system 200 can be employed within or as part of a bag connector, such as connector 94 (FIGS. 7A-7C), connector 294 (FIGS. 16A-16D), or with other bag connectors. Attachment system 200 can be integrally or separately formed with respect to a bag connector. For example, attachment system 200 can be a permanent or removable insert that can be inserted within a bag connector. Attachment system 200 can attach to a bag through adhesive, welding (for example ultrasonic) or other suitable methods. In some embodiments, attachment system 200 can be configured to be inserted into, or received by, the opening of a bag, with a sleeve, collar or other bag coupling structure positioned to secure the bag between the sleeve and the attachment system 200, such as the embodiments shown in FIGS. 16A-16D. When attachment system 200 is attached to a bag, and also attached to a vaporizer bowl, the bag can fill with vapors. The attachment system 200 can include a magnetic portion (FIG. 14D), threads, clamps, or other suitable structure to attach to the bowl (for example, bowl 50; FIGS. 6A, 6B; bowl 250; FIGS. 14E-16C), as described further herein. System 200 can include ribs 205 extending along at least an outer portion of body 201, for heat transfer, ease of handling and/or to facilitate attachment to a bag. The system 200 (i.e., one or more of its components) may be made of a flexible material with low thermal conductivity, such as a flexible polymer, such as silicone, to facilitate thermal isolation from the vaporizing device.

FIGS. 14A-14E illustrate an embodiment of attachment system 200 that includes valve 210. Valve 210 can be positioned within lumen 202. Valve 210 can function substantially similar to valve 94a described herein (FIG. 7C). Any suitable valve that allows flow of vapor in one direction and prevents substantial flow of vapor in the opposite direction can be used. Valve 210 can be separately formed, or a unitary construction (integrally formed), with respect to body 201. Valve 210 can be any suitable configuration to allow vapors to flow into a bag attached to system 200, when system 200 is attached to a vaporizer. Valve 210 can be any suitable configuration to prevent the vapors from escaping the bag when system 200 and a bag attached thereto are removed from a vaporizer. In some embodiments, valve 210 can include two flaps that form a duck-bill valve. Valve 210 can include only two flaps 211, 212, without additional flaps. In some embodiments, one of flaps 211, 212 can be integrally formed without substantially extending from a sidewall of lumen 202, and without substantial movement, such that the other of flaps 211, 212 extends from the sidewall and moves to open and close the valve.

Valve 210 can comprise a check valve (for example, one-way valve) configured to move between a first open position which allows flow of vapor through the lumen in a first direction 901 (FIG. 14A) extending from the opening 202A to the opening 202B of the body 201, and a second closed position which prevents substantial flow of vapor through the lumen in a second direction 902 from the opening 202B to the first opening 202A of the body 201. For example, valve 210 can be configured to open and allow flow of vapor in the first direction 901, when opening 202A has a pressure greater than the pressure at opening 202B (for example, after exceeding a cracking pressure of the valve). Valve 210 can be configured to close and prevent substantial flow of vapor from opening 202B to 202A, and escaping the bag, when opening 202A has a pressure lower than or equal to the pressure at opening 202B (for example, lower than a cracking pressure of the valve, such as when the vapor source stops supplying vapor to the bag, or when the bag is disconnected from the vapor source). In some embodiments, the cracking pressure of the valve can correspond to the output of vapor from a therapeutic vaporizer, which may be lower than some applications, or approximately 0.5 to 20 psi. In some embodiments, the cracking pressure of the valve can correspond to the output of vapor from a therapeutic vaporizer, which may be lower than some applications, or approximately 1 to 10 psi.

In some embodiments, valve 210 can comprise a selective valve, such as a selective check valve, which allows flow in the first direction 901 and selectively prevents flow in the second direction 902 (FIG. 14A). For example, valve 210 can be configured to selectively open and close in response to extending a protrusion to and from lumen 202, respectively, within opening 202A. When a protrusion is extended into and received by valve 210 (for example, through the first opening 202A and into lumen 201), valve 210 can open and allow flow in both directions 901, 902. For example, as shown in FIG. 14E, when a protrusion 270 is inserted into the valve 210 through the first opening of the body, the valve can move to the first position and allow flow in the second direction. Protrusion 270 can comprise any suitable device to allow insertion into valve 210, such as a tube. In some embodiments, protrusion 270 can comprise a portion of a vaporizer bowl, such as fitting 59a (FIGS. 6A/6B; 15A/15B). Valve 210 can be configured such that when protrusion 270 is removed from valve 210 (for example, from opening 202A), the valve 210 automatically returns to the closed position, for example, without additional external forces. Thus, removing the protrusion can automatically close the valve and prevent flow through the valve in direction 902.

Referring to FIGS. 14B and 14C, valve 210 can also be configured to selectively open and close in response to applying and removing an external force, such as a transverse force, on body 202. For example, when attachment system 200 is removed from a vapor source, and without a protrusion extending into valve 210 or other external forces being applied to valve 210, flow is prevented from the bag in direction 902 (FIG. 14A) as described above. However, valve 210 is configured such that if squeezed, and subject to a force, such as a transverse force as shown by directional arrows 900, flaps 211 and 212 spread apart, opening valve 210 and allowing vapors to travel through valve 210 from the bag. The transverse force can be approximately aligned with the edge of contact between flaps 211 and 212. Valve 210 can be configured such that when an external force is removed from body 202, the valve 210 automatically returns to the closed position, for example, without additional external forces. Thus, removing the force can automatically close the valve and prevent flow through the valve in direction 902.

Flaps 211, 212 can extend within the lumen 202 inwardly from the inner sidewall of the body 201. The distal ends of the flaps 211 and 212 can form a seal to prevent the substantial flow of vapor in the second flow direction 902. Flaps 211, 212 can be oriented at an angle with respect to each other, to form an apex that can move, to allow and disallow contact between the ends of flaps 211, 212. In some embodiment, a portion of the apex can be attached, for example, proximate to the inner sidewall of body 201. As best shown in FIG. 14D, the flaps 211 and 212 of the valve can form an angle $\alpha$ with the inner sidewall of the body 201. A smaller angle $\alpha$ can allow the flaps 211, 212 to more easily open (for example, during insertion of protrusion 270 through opening 202A, as described above), but a larger angle $\alpha$ can allow the use of flaps with shorter length and reduce the overall footprint of the valve. Therefore, the range of the angle $\alpha$ can be selected to balance these opposing factors and affect the functionality of the valve. In addition, the range of the angle $\alpha$ can also depend on the configuration and the material of the valve. If the flaps are too short or the angle $\alpha$ is too large, or if the valve material is too soft or thin, the vapor pressure inside the bag can push open the valve and allow the vapor to flow in the second flow direction 902 and thus defeating the purpose of the valve. If the flaps are positioned too close to the inner wall and the angle $\alpha$ is too small, the valve may not seal when the back pressure of the vapor inside the bag is low. The flaps can be pre-loaded or pre-formed with a bias against each other when in a quiescent state, to keep the valve closed through hysteresis when there is approximately no pressure drop across the flaps (across openings 202A and 202B). In some embodiments, the flaps extend from the inner sidewall of the body in the first direction at a non-orthogonal angle $\alpha$. In some embodiments, the angle $\alpha$ can be in the range of approximately 10 degrees to approximately 80 degrees. In some embodiments, the angle $\alpha$ can be in the range of approximately 20 degrees to approximately 60 degrees. In some embodiments, the angle $\alpha$ can be in the range of approximately 25 degrees to approximately 55 degrees. In some embodiments, the angle $\alpha$ can be in the range of approximately 30 degrees to approximately 50 degrees. In some embodiments, the angle $\alpha$ can be in the range of approximately 30 degrees to approximately 45 degrees. In some embodiments, the angle $\alpha$ can be in the range of approximately 35 degrees to approximately 45 degrees. In some embodiments, the angle $\alpha$ can be in the range of approximately 35 degrees to approximately 40 degrees. In some embodiments, the angle $\alpha$ can be in the range of approximately 37 degrees to approximately 42 degrees. In some embodiments, the angle $\alpha$ can be in the range of approximately 20 degrees to approximately 60 degrees. In some embodiments, the angle $\alpha$ an angle greater than approximately 37 degrees and less than approximately 40 degrees. In some embodiments, the angle $\alpha$ can be approximately 37 degrees. In some embodiments, the angle $\alpha$ can be approximately 38 degrees.

The attachment system 200 and its components can be made of any materials or any configurations suitable for easy use, manufacture, and/or within the context of chemistries and temperatures for vaporization of a therapeutic material. For example, two or more of the components of system 200, such as the valve 210 and the body 201, can comprise a common material. In some embodiments, two or more of the components of system 200, such as the body and/or the valve can comprise silicone materials. The valve 210 and body 201 can be made of any materials with sufficient strength, flexibility, and elastic properties suitable to allow an average adult human user to transversely displace the body and valve to open the distal end of the flaps and move the valve from the second position to the first position, as described above.

In some embodiments, the valve 210 and body 201 can be configured such that the valve 210 can be opened in response to a low transverse force, such as that of a human with a reduced physical capacity. For example, in some embodiments, the body 201 and valve 210 are configured such that the distal ends of the flaps separate and move the valve from the second position to the first position in response to a transverse force of between approximately 0.5 and 10 pounds, and in some embodiments, as low as approximately 0.5 pound. In some embodiments, the body 201 and valve 210 are configured such that the distal ends of the flaps separate and move the valve from the second position to the first position in response to a transverse force of between approximately 1 and 10 pounds. In some embodiments, the body 201 and valve 210 are configured such that the distal ends of the flaps separate and move the valve from the second position to the first position in response to a transverse force of between approximately 1 and 5 pounds. The use of flexible materials (for example, a flexible polymer falling between approximately 15-70 Shore A hardness) can facilitate such lower valve actuation forces. In some embodiments, the valve 210 includes a simple, easy to use structure, without any components (such as a spring), other than flaps 211, 212 extending from body 201, allowing the valve to be opened and closed easily and without additional complexity.

The attachment system 200 can include one or more of a number of different structures to provide additional functionality. For example, body 201 can include a ridge 219 (FIGS. 14D and 14E) extending from an inner wall of body 201 and into lumen 202. Ridge 219 can be near the opening 202A. Ridge 219 can form an inner perimeter (for example, a circular perimeter) extending within lumen 202 from the inner wall of body 201. The ridge can form a ring or other circular shape, or any other suitable shape. The ridge can improve engagement between, and in some embodiments, seal against, body 201 and another component, such as a protrusion extended into lumen 202A. As such, an engagement element protruding from the inner wall of body 201, such as ridge 219, can form a lip seal between body 201 and a protrusion inserted into lumen 202A. The ridge can reduce the amount of heat transferred from another component, such as the protrusion, to the body 201 or the valve 210. Such structure can reduce wear and increase the life expectancy of the attachment system 200. Ridge 219 can have any cross sectional shape that extends into lumen 202A and suitable to engage with a protrusion inserted therein.

The body 201 can include a plurality of spaced ribs 205, as mentioned above, extending at least partially along an outer surface of the body. The ribs can provide ease of handling of body 201 and/or facilitate attachment of system 200 to a bag, and/or cool the ribs by reducing the amount of heat transferred from the body 201 to a user. The ribs 205 can extend partially along the outer portion of the body 201 as shown in FIG. 14A. In some embodiments, ribs 205a can extend fully along the outer portion of the body 201 as shown in FIG. 14D. The ribs can be spaced evenly, or unevenly, around some, or substantially the entirety of a length or outer perimeter of body 201.

The attachment system 200 can include an inhalation bag, such as those bags described elsewhere herein. The bags herein, including that implemented with system 200, can have any capacity suitable to store therapeutic vapor for human inhalation. In some embodiments, the capacity of the bag is at least approximately the average tidal lung volume of an adult human of approximately 0.5 liters. In some embodiments, the capacity of the bag is between approximately 0.9 and 2 times the average tidal lung volume of an adult human. In some embodiments, the capacity of the bag is at least the average vital lung capacity of an adult human (which is approximately 4.6 liters). In some embodiments, the capacity of the bag is at least the average total lung capacity of an adult human. The average total lung capacity of an adult human is the average vital lung capacity (of approximately 4.6 liters) plus the average residual lung capacity that remains in the lungs after each exhale (which is approximately 1.2 liters), for an average total lung capacity of approximately 6 liters. In some embodiments, the volume of the bag falls in a range of approximately ⅓ to 2 times the total lung capacity. For a greater number of users, the bag can be sized with an inner volume of ½ liter to 24 liters.

Components of the attachment system (or other components of the vaporizers described herein) can comprise heat-resistant materials rated to operate reliably within boundaries of temperatures of a vaporization process for vaporizing therapeutic materials. For example, a vaporization process for vaporizing therapeutic materials may operate in temperatures approaching temperatures as low as approximately room temperature ° C. and as high as approximately 300° C. A vaporization process for vaporizing therapeutic materials may operate at a temperature as high as approximately 300° C., or less. In some embodiments, the vaporization process for vaporizing therapeutic materials may operate at a temperature as high as approximately 260° C., or less. Some vaporization processes for vaporizing therapeutic materials may operate in temperatures of at least approximately 260° C. In some embodiments, the vaporization processes for vaporizing therapeutic materials may operate in temperatures of at least approximately 200° C. Some vaporization processes for vaporizing therapeutic materials may operate in temperatures of at least approximately 120° C. Thus any of the components of the vaporizers (and attachment systems, and other components) described herein can comprise materials suitable to operate within these ranges. In some embodiments, one or more components that are in contact with the therapeutic vapor, including the body, coupling, valve and/or bag, can comprise materials that are heat-resistant within one or more of these temperature ranges. For example, at least one of the body, coupling, valve and bag can comprise a material resistant to a temperature of at least approximately 120 C. For example, at least one of the body, coupling, valve and bag can comprise a material resistant to a temperature of at least approximately 200 C. In some embodiments, at least one of the body, coupling, valve and bag can comprise a material resistant to a temperature of approximately 300° C. or less. In some embodiments, at least one of the body, coupling, valve and bag can comprise a material resistant to a temperature of approximately 260° C. or less. In some embodiments, at least one of the body, coupling, valve and bag can comprise a material resistant to a temperature of approximately 250° C. or less. In some embodiments, at least one of the body, coupling, valve and bag can comprise a material resistant to a temperature of approximately 200° C. or less. In some embodiments, at least one of the body, coupling, valve and bag can comprise a material resistant to operating within a temperature range of between approximately 100° C. and 300° C. In some embodiments, at least one of the body, coupling, valve, and bag are made of materials selected from the group consisting of silicone rubber, polyethylene naphthalate (PEN) plastic, polyethylene sulfone (PES) film, polyether imide (PEI) plastic, polysulfone (PSF) plastic, polyphenylene sulfide (PPS) plastic, polyarylate (PAR) plastic, aramide plastic, liquid crystal polymer (LCP) plastic, hemp fiber, and any combinations thereof. In some embodiments, at least one of the body, coupling, valve, and bag are made of silicone rubber. In some embodiments, at least one of the body, coupling, and valve are made of a flexible polymer, such as rubber, and in some embodiments, a high temperature flexible polymer, such as silicone rubber.

In some embodiments, the apparatus 200 can include a magnetic attachment portion 253 to couple the body 201 with an external device, such as an outlet of a therapeutic vaporizer (for example, a bowl). Any of the magnetic attachment portions described herein can be a magnetic material (i.e. a magnetized material, or magnet), or a magnetically attractive material (i.e., a material that can be, but is not necessarily magnetized, and can be attracted to a magnet) configured to engage with a corresponding magnetic attachment portion on another component. Portion 253 can allow for apparatus 200 to easily be attached to and detached from another device, such as a bowl of a therapeutic vaporizer. Such ease of attachment can be beneficial for users with diminished physical capacity. In some embodiments, the magnetic attachment portion 253 can be attached to first end 201A of body 201. The magnetic attachment portion 253 can be attached to body 201 in any suitable way, such as with adhesive (for example, high temperature adhesive, such as epoxy (such as the epoxy sold under the tradename JB Weld) and resin. The magnetic attachment portion 253 can also be applied onto or in conjunction with the body 201, Portion 253 can be integrally formed (for example, molded with) body 201. For example, a high temperature plastic or rubber can be molded around a magnetic material portion 253. Portion 253 can be attached to an exterior portion of body 201, or can be attached within an internal portion of body 201. For example, portion 253 can be partially or completely molded within body 201. For example, portion 253 can be completely molded within body 201 such that portion 253 does not have any direct contact with components external to body 201. The magnetic attachment portion 253 can be made of any suitable magnetic material or magnetically attractive material described elsewhere herein. The magnetic attachment portion 253, and other magnetic attachment portions described herein can be a magnetic or non-magnetic material, with a coating layer made of magnetic material or magnetically attractive material. The magnetic material can be any material suitable to maintain magnetic attraction at higher temperatures, such as within temperatures of vaporization of a therapeutic material. For example, the magnetic material can be ceramic, samarium cobalt, or neodymium. The magnetic material can comprise rare-earth magnetic materials, which will retain a serviceable percentage of their attractiveness when exposed to higher temperatures, such as vaporization temperatures.

FIGS. 14D and 14E show an embodiment of attachment system 200. System 200 can include a bag coupling 260. Bag coupling 260 can attach the body 201, such as the second end 201B, to inhalation bag 84 (FIGS. 1B; 7A-7C; 14E). The bag coupling 260 can be easily removed from the body 201 of the attachment system 200. The bag coupling 260 can also be permanently attached to the body 201 of the attachment system 200. Any suitable coupling mechanism can be used between the bag coupling 260 and the body 201 to prevent gas leakage when the inhalation bag is attached to the body using the bag coupling. The bag coupling, once assembled, can be either inserted inside the lumen of the body 201 as shown in FIG. 14F or extended around the body 201 like a sleeve as shown in FIGS. 16A-16D.

For example, as shown in FIGS. 14D and 14E, the bag coupling 260 can include an inner bag collar 214 and an outer bag collar 215. The inner bag collar 214 can be configured to be inserted into an opening 93 of an inhalation bag 84 (see, for example, FIGS. 7A and 14E). The outer bag collar 215 can be configured to receive the inner bag collar 214, with the inhalation bag 84 positioned between the inner bag collar 214 and outer bag collar 215. The inner bag collar 214 and outer bag collar 215 can be configured to be inserted into and form a seal with an inner surface of a sidewall of the body 201, as shown in FIG. 14E. In some embodiments, at least one, and in some embodiments, both, of the inner bag collar 214 and the outer bag collar 215 can include radially extending engagement elements configured to engage with and improve sealing and/or attachment between coupling 260 and body 201. These engagement elements can comprise flanges, barbs, grooves, or other suitable engagement means. For example, as shown in FIGS. 14D and 14E, the outer bag collar 215 has an external barb 218 fitted to engage with body 201. The inner bag collar 214 includes a barb 217 and a flange 216 extending around its lower and upper ends, respectively, to couple with the outer bag collar 215. In some embodiments, the body 201 can include a corresponding engagement element to actively engage with corresponding engagement elements on collars 214, 215. For example, the body 201 can include a groove, shoulder or other structure, such as groove 207, configured to receive and engage with barb 218. Other types of coupling mechanisms may also be utilized. For example, the inner bag collar may be frictionally held within the outer bag collar, due to the passive tension of the slightly compressed inner bag collar walls exerted against the outer bag collar. The bag coupling can comprise an inner bag collar and an outer bag collar. The inner bag collar can be configured to be inserted into the opening of the inhalation bag, with the outer bag collar configured to receive the inner bag collar. The inhalation bag can be positioned between the inner bag collar and outer bag collar. The inner bag collar and outer bag collar can be configured to be inserted into and form a seal with an inner surface of a sidewall of the body. At least one of the inner bag collar and the outer bag collar can include radially extending engagement elements configured to engage with the inner surface.

When the bag coupling 260 is assembled together with the inhalation bag placed between the two collars 214 and 215, the bag coupling can be inserted into the body 201 as shown in FIG. 14E. Gas or vapor flowing through the body 201 can flow into the inhalation bag 84 without substantial leakage.

The bag coupling 260 can comprise any of the materials described above for the valve and body. Parts of the attachment system that are in contact with the therapeutic vapor, including the body, coupling, valve and bag, can be made of materials resistant to chemicals. In some embodiments, one or more components of the vaporizer or attachments system described herein, such as at least one of the body, coupling, valve and the bag, comprises a material, such as silicon, that is chemically resistant to a vapor formed from a vaporizable therapeutic material, and/or other materials.

In some embodiments, a lower surface of the first end 201A of body 201 can include a concavity 209, to facilitate engagement or sealing with a vaporizer bowl, and/or to conform with and provide comfort to a user of system 200. First end 201A can also include a flange extending therefrom. The lower surface of the first end 201A of body 201 and/or the flange can form a mouthpiece, providing similar function as mouthpiece 82b, described here with respect to inhalation tube 82 (FIG. 8). Thus, the attachment system 200 can comprise a unitary, monolithic construction that forms a valve, body, and mouthpiece, while being configured to receive an inhalation bag, without any additional components, other than a bag coupling to connect a bag to the body 201 of the system 200.

The attachment system described herein provides a user friendly and simply way to affix an inhalation bag to the vaporizer device. The attachment systems described herein may have fewer components, improving ease of assembly with reduced cost of manufacturing. Reduced alignment of components may be needed in the assembly process and the system can stay in place until intentionally dissembled. The valve in the attachment system can be easily opened by applying a reduced squeeze force around the outer opening of the valve or by inserting a protrusion into the valve; and the valve can automatically close once the squeezing force is removed or the protrusion is no longer present in the valve. The use of magnetic attractive components in the attachment system further increases the ease of use and provides additional conveniences to users, particularly to users with dexterity problems.

In addition, the use of heat-resistant material in the attachment system can reduce expansion or contraction of the system during temperature changes. Thus, various parts of the system can remain stable and have a reduced likelihood of loosening in the vaporization temperature values and ranges for therapeutic materials. Moreover, the inhalation bags can be replaced without disposing other components of the attachment system. Various components of the attachment system such as the valve and the coupling can be easily re-assembled with a replacement inhalation bag and have a reduced replacement cost.

Further, the attachment system described herein can be made of soft and elastic materials such as silicone, which can allow for engagement and fit with various sizes of vapor sources, such as various vaporizer bowl outlets. The attachment systems can be stretched to fit with a vapor source that has an opening larger than the opening of the attachment system. The stretched silicone material can seal tightly around the opening of the vapor source and substantially reduce the likelihood of vapor leaking near the attached portion.

Figures 15A, 15B:
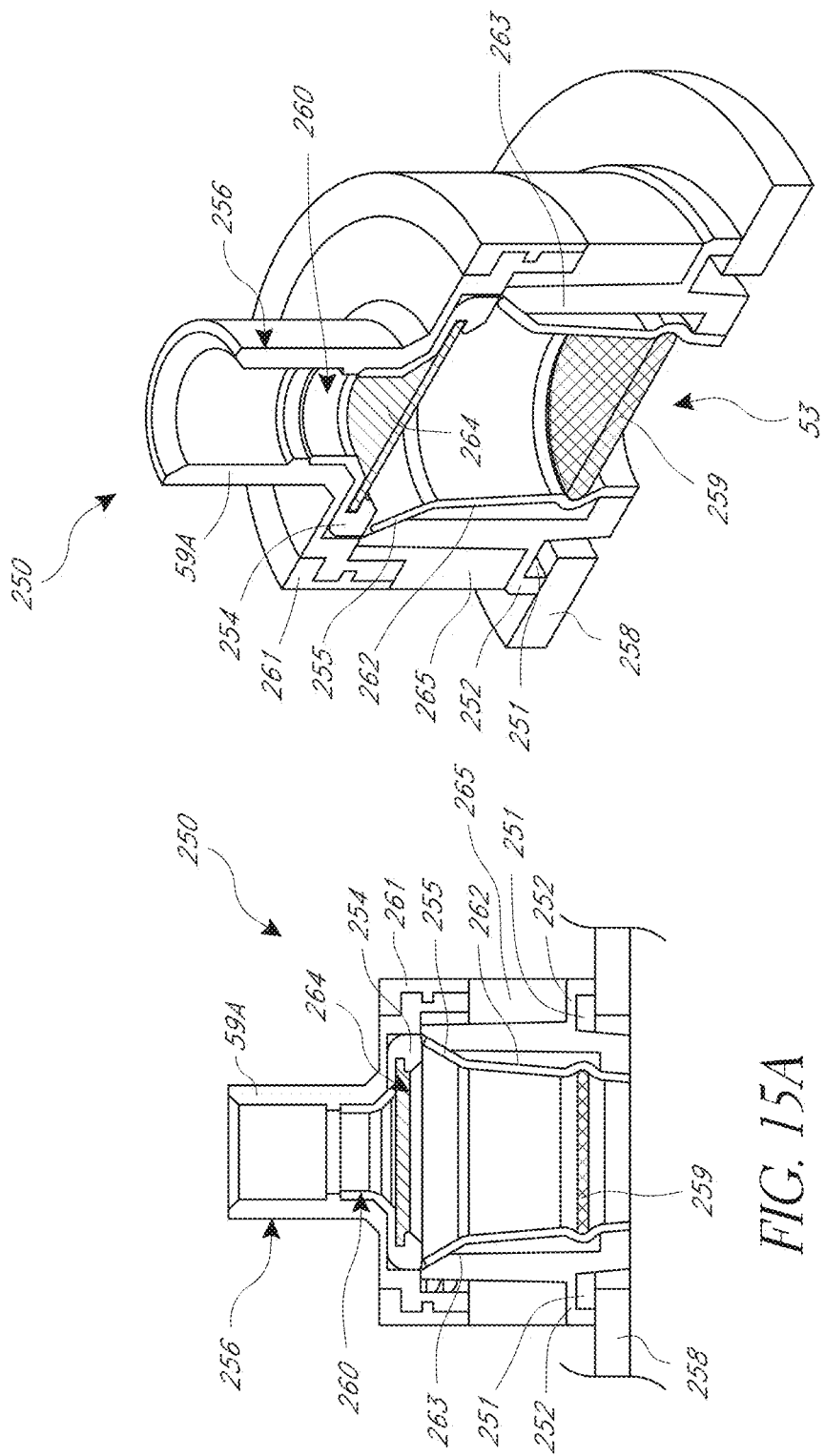
FIGS. 15A-15B are side and perspective cross-sectional views, respectively, of an embodiment of a bowl configured to magnetically attach to a vaporizer.

FIGS. 15A-15D are various views of a bowl 250 configured to magnetically attach to a vaporizer. Bowl 250 can be substantially similar to bowl 50 described elsewhere herein (FIGS. 1B, 1C, 6A, 6B). Bowl 250 can include a first bowl magnetic attachment portion 251 configured to magnetically attach to a corresponding vaporizer magnetic portion 258 of the vaporizer. Magnetic portion 251 can be any portion of bowl 250 suitable to magnetically engage with the vaporizer magnetic portion 258. Magnetic portion 251 can comprise materials and be configured similarly as the magnetic portion 253 of attachment system 200 (FIG. 14A). In the illustrated embodiment, bowl magnetic portion 251 comprises a ring supported on a flange 252 at the lower end of bowl 250. The vaporizer portion 258 can include any portion of a vaporizer suitable to magnetically engage with the bowl portion 251, such as flanges 89, or portions of bowl receptacle 85, as described with respect to vaporizer 10 (for example, FIG. 1C). Referring to FIGS. 15A-15B, the bowl 250 can include a bowl cap 256 with a bowl fitting 59a suitable for attachment to an inhalation tube 82 (for example, FIG. 8) or to inhalation bag 84 (for example, FIGS. 7A, 14E), or bag attachment system 200 (for example, FIGS. 14A-14E; 16A-16D). The bowl cap 256 can include a magnetic portion 254 to magnetically couple the bowl 250 with a corresponding magnetic portion on an inhalation tube, inhalation bag, or bag attachment system. For example, the bowl magnetic portion 254 can magnetically couple bowl 250 (for example, fitting 59a) with a corresponding magnetic portion 253 on bag attachment system 200 (FIG. 14D). Bowl 200 can include a base 263 configured to engage with the cap 256 and form an inner volume for receiving vaporizable therapeutic material. Bowl 200 can include a bowl sleeve 260, generally comprising a metal material, configured to be inserted into the volume formed within base 263 and cap 256. Sleeve 260 can comprise one or more components, such as a bowl sleeve base and bowl sleeve cap. A first bowl screen 259 can be positioned within a lower portion of sleeve 260, to support vaporizable material, and a second bowl screen 264 can be provided as a filter to remove any particles carried in the vapor that are flowing out of the bowl.

The bowl 250 can include one or more handling portions, such as handling portions 261 and 265, configured to surround and provide ease of handling of cap 256 and base 253, respectively. Handling portions 261 and 265 can comprise a thermally insulating material, to reduce the external temperature of the bowl 200, for comfort to a user and to provide a cooling grip to prevent injury at higher bowl/vaporization temperatures. Handling portion 261

Figure 15D:
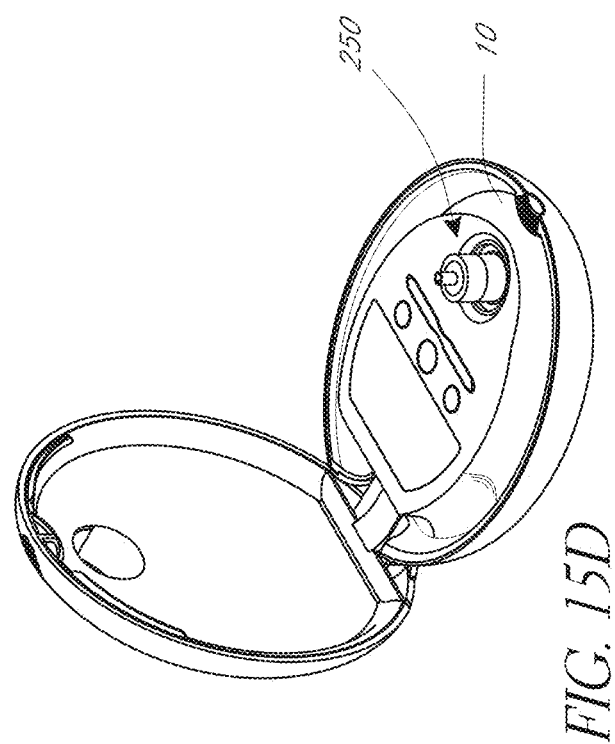
FIGS. 15C-15D are perspective views showing an embodiment of a bowl magnetically decoupled and coupled, respectively, to a portion of a therapeutic vaporizer.
Figure 15C:
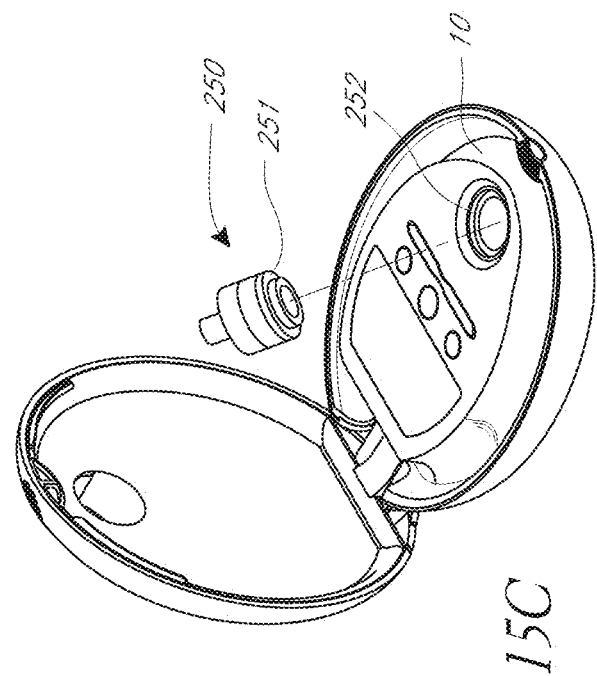

The bowl can also include a magnetic portion 251, positioned, for example, on the lower portion for attaching the bowl to the vaporizer through magnetic attraction. Referring to FIGS. 15C and 15D, when the bowl 250 is moved to be in proximity to the vaporizer 10, the magnetic attraction between magnetic portion 251 of the bowl 250 and the magnetic portion 253 of the vaporizer 10 moves the bowl 250 into position and holds it until the two are separated from each other. The magnetic portions described above can facilitate attachment of the bowl 250 to the vaporizer 10, which can be of benefit to people with dexterity issues or reduced physical capacity, such as Parkinson's disease, or the elderly.

Parts of the bowl 250 that are in contact with the therapeutic vapor, including the bowl housing, bowl screen, bowl sleeve and the bowl cap housing, can be made of heat-resistant materials. In some embodiments, the bowl comprise a materials resistant to (for example, capable of withstanding without significant degradation in performance) a temperature of at least approximately 260° C. In some embodiments, the bowl comprise a material resistant to a temperature of approximately 260° C. or less. In some embodiments, the bowl is made of materials selected from the group consisting of silicone rubber, aluminum oxide ceramic, borosilicate glass, and stainless steel metal In some embodiments, at least a part of the bowl is made of stainless steel. In some embodiments, at least a part of the bowl is made of aluminum oxide ceramic. In some embodiments, at least a part of the bowl is made of borosilicate glass.

Parts of the bowl that are in contact with the therapeutic vapor, including bowl housing, bowl screen, bowl sleeve and the bowl cap housing, can be made of materials resistant to chemicals from vaporized therapeutic materials (for example, capable of contacting such vapors without significant degradation in performance). In some embodiments, the bowl comprises a material chemically resistant to a vapor formed from a vaporizable therapeutic material, such as those described above.

The magnetic portion 251 on the bowl can be made of magnetic material or magnetically attractive materials that are heat resistant. The magnetic portion 251 on the bowl can also be a coating layer made of magnetic material or magnetically attractive material. In some embodiments, the magnetic material or magnetically attractive material can be ferrous materials. Examples of the ferrous materials include but are not limited to iron and steel. In some embodiments, the magnetic material or magnetically attractive material can be rate earth materials with magnetic properties. In some embodiments, the magnetic material or magnetically attractive material can be ceramic, neodymium or samarium cobalt.

As described above, the aforementioned portions 251, 252, 253, and/or 254 of bowl 250, vaporizer 10, or attachment system 200 can comprise a magnet, or a magnetic material, provided each paired combination includes at least one magnet. Any of a number of different magnetic materials can be used, such as magnetic SST. Some embodiments include magnetic materials suitable for higher temperatures, such as ceramic or neodymium. Surface preparation such as powder bake paint or ruggedized polymer coating may be applied to increase durability. The amount of the magnetic attraction force between the magnetic portion 253 of the body and the corresponding magnetic portion 253 on the bowl can be tailored so as to work in cooperation with other parts of the therapeutic vaporizer. For instance, the magnetic force between the bowl and the vaporizer may be greater than that between the attachment force between other accessories, such as between the inhalation tube 82 and the bowl, the attachment system 200 and the bowl, or the mouthpiece 82b and the conduit 82a of the inhalation tube 82 (see also FIG. 8), so that the bowl stays attached to the vaporizer when these other accessories are magnetically decoupled. For example, when the magnetic portion 253 of the body 201 of the attachment systems 200 is connected to the bowl 250 and the magnetic portion of the body is magnetically attracted to the corresponding magnetic portion 254 on the bowl cap, the magnetic force between the magnetic portion 253 of the body and the corresponding portion 254 on the bowl cap can be smaller than the removal force of the bowl magnetic attachment portion 251 and the corresponding vaporizer magnetic portion 252 of the vaporizer. Therefore, when the attachment system is removed from the bowl cap, the bowl 250 can stay in place.

Figure 16A:
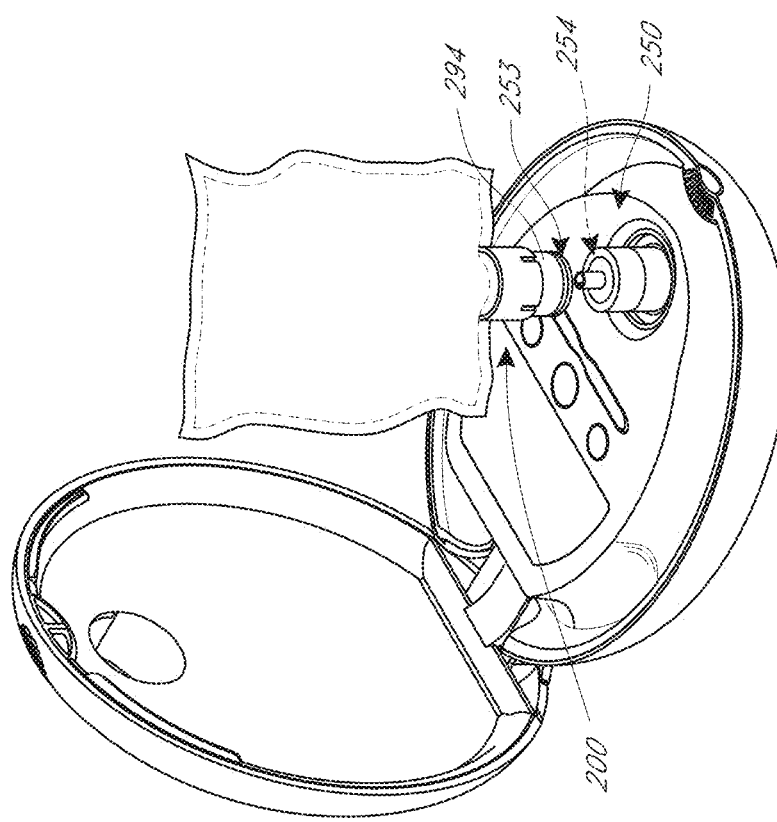
FIGS. 16A-16D are various views of an embodiment of an attachment system for an inhalation bag.
Figure 16B:
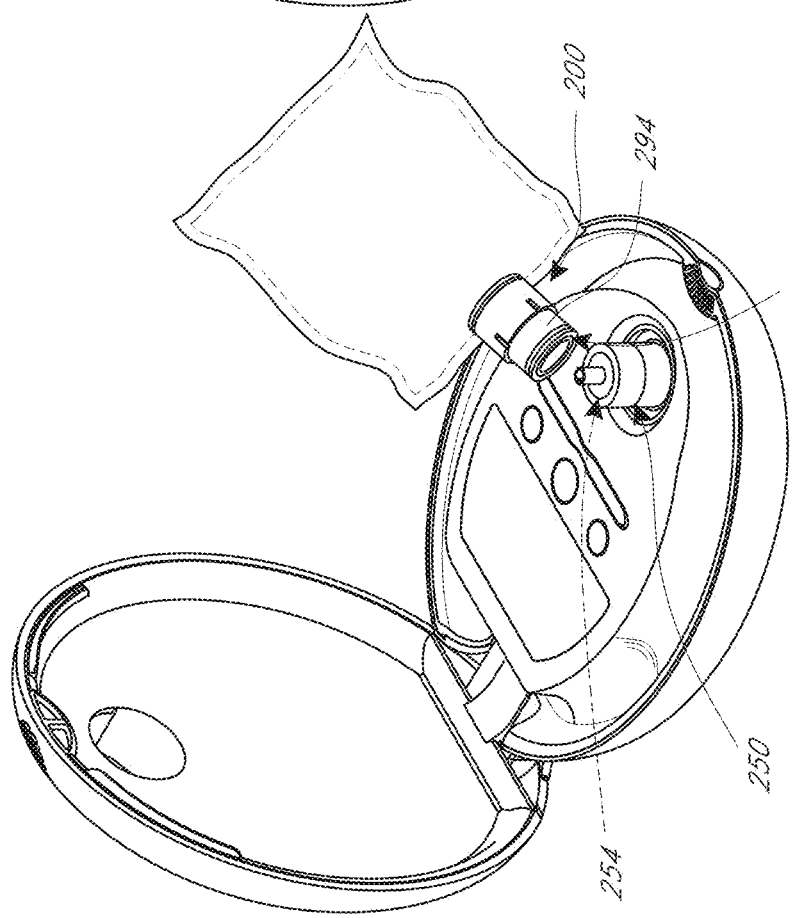
Figure 16D:
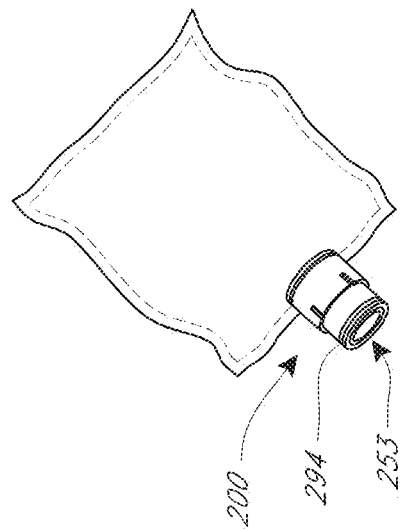
Figure 16C:
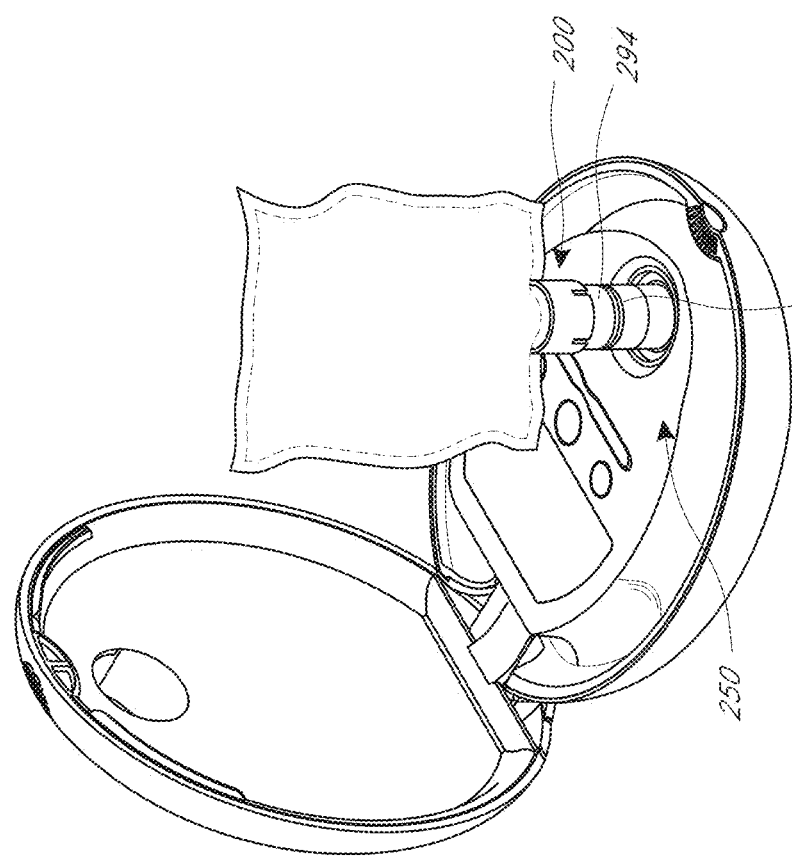

FIGS. 16A-16D are various views of attachment system 200. Attachment system 200 can optionally include the valve 210 (FIGS. 14A-14C). System 200 can include a connector 294 that includes a bag magnetic portion 253 configured to magnetically attach to a corresponding second bowl magnetic portion 254 on bowl 250 (FIGS. 15A-15B). Bag magnetic portion 253 can be any of a number of shapes, such as an annular ring supported within a flange at the lower end of connector 294. In some embodiments, an inner shell 255 within bowl 250 can comprise a material suitable for magnetic engagement with bag magnetic portion 253 and/or vaporizer magnetic portion 252. Referring to FIGS. 16A-16C, when the attachment system 200 is moved to be in proximity to the bowl 250, the magnetic attraction between the portion 254 of bowl 250 and portion 253 of connector 294 moves the system 200 into position and holds it until the two are separated from each other. The magnetic portions described above can facilitate attachment of the bowl 250 to the bag, through the attachment system 200, which can be of benefit to people with dexterity issues, such as Parkinson's disease, or the elderly.

FIGS. 17A-17D are various views of an upper tray 300 for a vaporizer. Upper tray 300 can be employed within vaporizer 10. Additional, unnumbered views of the upper tray 300 are shown in the design patent filed concurrently herewith.

Upper tray 300 can be movable between a closed position, in which it is engaged within upper housing portion 62 of vaporizer 10 (see also FIGS. 1A-1C), and an open position, in which a user can access the top of upper tray 300 to remove or secure accessories. For example, vials containing herbs, a container containing an inhalation bag, or other accessories can be secured on upper tray 300, and hidden from view when upper housing portion 62 is opened. This provides both an aesthetic advantage, and can help secure accessories within vaporizer 10. The upper tray 300 can include one or more clips, clamps, or other suitable engagement mechanisms 310 to secure such accessories on upper tray 300. Upper tray 300 can include a shield 320 to shield, isolate, or seal the interior of tray 300 from the mezzanine 90, and bowl 50 (FIGS. 1B-1C). The tray 300 can be an integral or removable part of the vaporizer 10. The tray 300 can include any of a number of attachment mechanisms to allow attachment to the remainder of vaporizer 10. Tray 300 can be removably attached to vaporizer 10 through one or more latches. Tray 300 can be pivotally attached to vaporizer 10, similar to the attachment described herein with respect to upper housing portion 62. Referring to FIGS. 17A and 17B, in some embodiments, upper tray 300 can include a hinge 330 with a raised protrusion 331 configured to engage and latch upper tray 300 with a corresponding portion of upper housing 62, lower housing 64, mezzanine 90, or another portion of vaporizer 10. Protrusion 331 can be positioned on a movable arm 332 to provide additional bias between protrusion 331 against another component. Referring to FIG. 17D, tray 300 can include a latch 340 configured to attach tray 300 to upper housing 62. It will be understood that some features of tray 300, and other components of vaporizer 10 are for aesthetic purposes, utilitarian purposes, or both.

In some embodiments, a method of using energy pulses to control a halogen bulb in a heating application within a vaporizer can be employed. Halogen bulbs have traditionally been used in lighting applications where they are turned on and left on continuously. Halogen bulbs may pose reduced reliability when not used in this intended manner. However, halogen bulbs possess a faster dynamic response than many other heating systems, and can thus provide improved control of temperature for an application where precise and accurate temperature control is required. In some embodiments, a method of controlling a halogen bulb in a vaporizer uses series and bursts of energy pulses of controlled amplitude, profile, and duration that result in precise temperature control and rapid response. This method may be tailored to improve the reliability and/or life of the halogen bulb.

Figure 18:
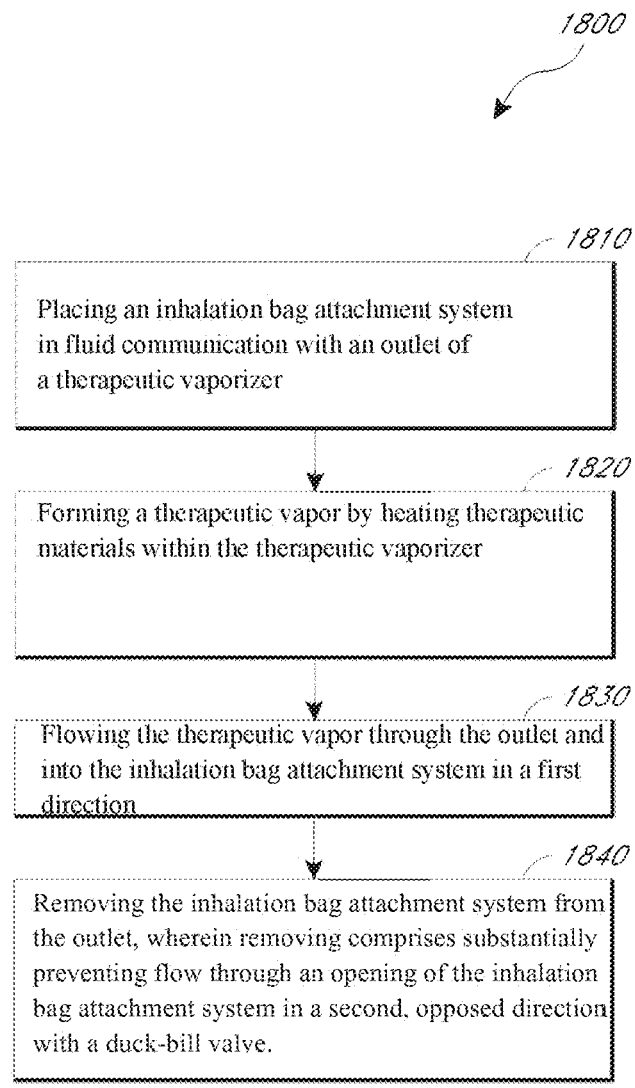
FIG. 18 is a flow diagram illustrating an embodiment of a method of using an inhalation bag attachment system.

FIG. 18 is an example of a flow diagram illustrating a method of using an inhalation bag attachment system for a therapeutic vaporizer. The method 1800 can include placing an inhalation bag attachment system in fluid communication with an outlet of a therapeutic vaporizer at block 1810. At block 1820, the method can include forming a therapeutic vapor by heating therapeutic materials within the therapeutic vaporizer. The method can also include flowing the therapeutic vapor through the outlet into the inhalation bag attachment system in a first direction at block 1830. The method can further include removing the inhalation bag attachment system from the outlet at block 1840. Removing the inhalation bag attachment system can include substantially preventing flow through an opening of the inhalation bag attachment system in a second, opposed direction with a duck-bill valve.

In some embodiments, placing the inhalation bag attachment system in fluid communication with the outlet of the therapeutic vaporizer comprises inserting a protrusion into the valve to open the valve. In some embodiments, removing comprises disengaging the protrusion from the valve to close the valve. In some embodiments, inserting the protrusion comprises engaging the protrusion with a lip seal extending from an inner wall into an inner lumen of the valve.

In some embodiments, the method further comprises applying a transverse force to the valve to open the valve and allow flow through the valve in both the first and second directions; and removing the force from the valve to automatically close the valve to prevent flow through the valve in the second direction.

In some embodiments, placing the inhalation bag attachment system in fluid communication with the outlet of the vaporizer comprises magnetically coupling the opening of the inhalation bag attachment system with the outlet of the vaporizer.

In some embodiments, flowing vapor through the outlet comprises flowing vapor through an outlet of a vaporizer bowl, further comprising magnetically coupling the bowl with the vaporizer.

In some embodiments, flowing the therapeutic vapor through the outlet into the inhalation bag attachment system comprises filling an inhalation bag with a capacity between approximately ⅓ to 2 times the total average lung capacity of an adult human In some embodiments, flowing the therapeutic vapor through the outlet into the inhalation bag attachment system comprises flowing a therapeutic vapor at a temperature of at least approximately 120° C.

In some embodiments, flowing the therapeutic vapor through the outlet into the inhalation bag attachment system comprises flowing a therapeutic vapor at a temperature of approximately 300° C. or less.

In some embodiments, the method of using an inhalation bag attachment system can further include attaching the valve to the opening of the inhalation bag, wherein attaching comprises: engaging an inner bag collar with an outer bag collar, with the bag opening positioned between the two collars to allow fluid communication from the bag opening through the two collars; and engaging the two collars with a body, wherein the valve is positioned within a lumen of the body.

In some embodiments, engaging the two collars with the body comprises inserting the body into the two collars.

In some embodiments, forming a therapeutic vapor comprises controlling the activation and deactivation of a heater of the vaporizer with a pulse-width modulated signal. Embodiments of the vaporizer described herein can allow aromatherapy and vapor therapy to be provided through the same device. In some embodiments, a segregated aromatherapy air-flow path and vaporization hot-air path can be provided within the same vaporizer, with the benefit of independent usage, either simultaneously, or separately (for example, in series).

Some embodiments relate to kits and products comprising one or more of the materials or components described herein. For example, the kits or products can include any of the devices (for example, vaporizers, controllers, heating components, etc., materials that are to be vaporized and/or heated for aroma, etc. Some embodiments relate to kits that can include for example, a bowl or support tray and a material that is to be vaporized or used to produce aroma, for example. In some aspects, any of the devices, components and materials described herein can be expressly excluded from certain embodiments. In other aspects one or more of the devices, components and/or materials described herein can be combined in different combinations, for example, any combination. While the word "therapeutic" is used herein, the application of the devices should not be limited to only strict therapeutic materials, but the methods can apply to any material that is sought to be vaporized or processed to create an aroma, regardless of whether the vapor or aroma strictly are therapeutic in the medical or healthcare sense. For example, the devices can be used to create pleasant aromas and vapors that are aesthetic or for ambience, rather than strictly for a therapeutic medical purpose.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments. In addition, reference to "one embodiment," "another embodiment," etc. is not generally intended to imply that embodiments described herein are separate and distinct, and/or mutually exclusive of one another. Thus, embodiments described herein may contain common elements, features and/or steps.

Those of skill would further appreciate that the various illustrative devices, methods, controllers, user interface or inputs, logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, microchip, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration.

In one or more example embodiments, the functions described may be implemented in hardware, software, or firmware executed on a processor, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While the above description has pointed out novel features of the invention as applied to various embodiments, the skilled person will understand that various omissions, substitutions, and changes in the form and details of the device or process illustrated may be made without departing from the scope of the invention. Therefore, the scope of the invention is defined by the appended claims rather than by the foregoing description. All variations coming within the meaning and range of equivalency of the claims are embraced within their scope.

It will also be understood that although many of the embodiments herein describe the use of various components in combination to form embodiments of a therapeutic many of the components can be manufactured and provided independently without other components. For example, embodiments of the heater, the inhalation bag, the inhalation tube, the bowl, the control system, sensor configuration, the gas analysis system, and any of the many other components described herein, or any combination thereof, can be provided separately, as part of a therapeutic vaporizer, and/or as a kit. Thus, the invention is not to be limited otherwise.

What is claimed is:

1. A therapeutic vaporizer inhalation bag attachment system with an integrated valve, comprising:
   a body comprising a lumen extending between a first opening at a first end of the body and a second opening at a second end of the body;
   a plurality of elongated cooling ribs extending in parallel with the lumen on and along an outer surface of a sidewall of the body to increase surface area;
   a magnetic attachment portion positioned on the first end of the body substantially perpendicular to the lumen;
   a ridge forming a circular perimeter and extending from an inner wall of the first end of the body and into the lumen;
   a bag coupling configured to attach an inhalation bag to the second end of the body; and
   a duck-bill valve positioned within the lumen and configured to move between a first position which allows flow of vapor through the lumen in a first direction extending from the first opening to the second opening, and a second position which prevents substantial flow of vapor through the lumen in a second direction from the second opening to the first opening, the valve comprising two flaps extending within the lumen inwardly from an inner sidewall of the body,
   wherein a distal end of the flaps form a seal to prevent the substantial flow of vapor in the second flow direction,
   wherein the body and valve are configured such that the distal ends of the flaps separate and move the valve from the second position to the first position in response to an inwardly transverse force, and wherein the valve is configured to move to the first position and allow flow in the second direction when a protrusion is extended through the first opening and through the distal end of the flaps and automatically return to the second position when the protrusion is removed from the first opening.

2. The attachment system of claim 1, wherein the flaps extend from the inner sidewall of the body in the first direction at a non-orthogonal angle.

3. The attachment system of claim 2, wherein the angle is in the range of approximately 20 degrees to approximately 60 degrees.

4. The attachment system of claim 1, wherein the body includes a lip seal extending from an inner wall of the body into the lumen, the lip seal configured to engage with the protrusion when the protrusion is extended through the first opening.

5. The attachment system of claim 1, wherein the body and valve comprise a unitary structure and a common material.

6. The attachment system of claim 1, wherein the valve consists essentially of the two flaps.

7. A therapeutic vaporizer comprising; the attachment system of claim 1;
a bowl having a bowl magnetic attachment portion; and
the inhalation bag; wherein the inhalation bag has a capacity between approximately ⅓ to 2 times the total average lung capacity of an adult human.

8. The therapeutic vaporizer of claim 7, wherein a portion of the bowl comprises the protrusion.

9. The attachment system of claim 1, wherein the body and valve are configured such that the distal ends of the flaps separate and move the valve from the second position to the first position in response to an inwardly transverse force of between approximately 0.5 pounds and 10 pounds.

10. The attachment system of claim 1, wherein the attachment system does not include a spring.

11. The attachment system of claim 1, wherein at least one of the body and the valve comprises a material resistant to temperatures in a temperature range of between 100° C. and 300° C.

12. The attachment system of claim 1, wherein at least one of the body and the valve comprises a material resistant to temperatures in a temperature range of at least 120° C.

13. A therapeutic vaporizer inhalation bag attachment system, comprising:
a body consisting of a lumen extending between a first opening at a first end of the body and a second opening at a second end of the body,
a plurality of elongated cooling ribs extending in parallel with the lumen on and along an outer surface of a sidewall of the body to increase surface area;
a mouthpiece and magnetic attachment portion on the first end of the body; a ridge forming a circular perimeter and extending from an inner wall of the first end of the body and into the lumen;
a bag coupling configured to attach an inhalation bag to the second end of the body; and
a duck-bill valve positioned within the lumen and formed from two flaps extending within the lumen inwardly from an inner sidewall of the body,
wherein a distal end of the flaps form a seal to prevent the substantial flow of vapor in the second flow direction,
wherein the body and valve are configured such that the distal ends of the flaps separate and move the valve from the second position to the first position in response to an inwardly transverse force, and
wherein the valve is configured to move to the first position and allow flow in the second direction when a protrusion is extended through the first opening and through the distal end of the flaps and automatically return to the second position when the protrusion is removed from the first opening.

* * * * *